(12) United States Patent
Cho et al.

(10) Patent No.: US 8,895,017 B2
(45) Date of Patent: Nov. 25, 2014

(54) HER-2 PEPTIDES AND VACCINES

(75) Inventors: Helen Kim Cho, San Diego, CA (US); Siradanahalli Chandrasekharalah Guru, San Diego, CA (US); Van To Tsai, San Diego, CA (US); Brian Gregory Pierce, Wayland, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/701,814

(22) PCT Filed: May 23, 2011

(86) PCT No.: PCT/IB2011/052246
§ 371 (c)(1),
(2), (4) Date: Dec. 3, 2012

(87) PCT Pub. No.: WO2011/154863
PCT Pub. Date: Dec. 15, 2011

(65) Prior Publication Data
US 2013/0078270 A1    Mar. 28, 2013

Related U.S. Application Data

(60) Provisional application No. 61/352,318, filed on Jun. 7, 2010.

(51) Int. Cl.
*A61K 39/00* (2006.01)
*C07K 14/71* (2006.01)
*C07K 14/82* (2006.01)

(52) U.S. Cl.
CPC ............ C07K 14/71 (2013.01); A61K 2039/53 (2013.01); A61K 39/0011 (2013.01); C07K 14/82 (2013.01)
USPC .................................................... 424/185.1

(58) Field of Classification Search
None
See application file for complete search history.

(56) References Cited

U.S. PATENT DOCUMENTS

| 5,846,538 | A | 12/1998 | Cheever et al. | |
|---|---|---|---|---|
| 6,015,567 | A | 1/2000 | Hudziak et al. | |
| 7,060,284 | B1 | 6/2006 | Kaumaya et al. | |
| 7,229,623 | B1 * | 6/2007 | Cheever et al. | 424/192.1 |
| 7,282,365 | B2 * | 10/2007 | Monaci et al. | 435/325 |
| 7,348,010 | B2 | 3/2008 | Zielinski et al. | |
| 7,449,559 | B2 * | 11/2008 | Ward et al. | 530/402 |
| 7,763,452 | B2 * | 7/2010 | Eskling et al. | 435/252.3 |
| 2003/0157119 | A1 | 8/2003 | Gaiger et al. | |
| 2004/0052811 | A1 | 3/2004 | Zielinski et al. | |
| 2006/0074038 | A1 | 4/2006 | Lee et al. | |

FOREIGN PATENT DOCUMENTS

| EP | 0 474 727 81 | | 7/1997 |
|---|---|---|---|
| WO | WO 90/14357 A1 | | 11/1990 |
| WO | WO 99/46992 A1 | | 9/1999 |
| WO | WO 01/08636 A2 | | 2/2001 |
| WO | WO 01/21192 A2 | | 3/2001 |
| WO | WO 02/12341 A2 | | 2/2002 |
| WO | WO 03/055439 A2 | | 7/2003 |
| WO | WO 2004/007734 A1 | | 1/2004 |
| WO | WO 2007/095038 | * | 8/2007 |

OTHER PUBLICATIONS

Baxevanis, C., et al., "Immunogenic HER-2/neu Peptides as Tumor Vaccines", Cancer Immunology and Immunotherapy, 2006, 85-95, vol. 55, No. 1.
Disis. M., et al., "Generation of Immunity to the HER-2/neu Oncogenic Protein in Patients with Breast and Ovarian Cancer Using a Peptide-based Vaccine, " Clinical Cancer Research, 1999, 1289-1297, vol. 5., No. 6.
Hsu, W., et al., "Increased Survival in Dogs with Maligant Mammary Tumours Oversexpressing HER-2 Protein and Dectection of a Silent Single Nucleotide Polymorphism in the Canine HER-2 Gene," The Veterinary Journal, 2009, 116-123, vol. 180, No. 1.

* cited by examiner

*Primary Examiner* — Marianne P Allen
(74) *Attorney, Agent, or Firm* — Austin W. Zhang

(57) ABSTRACT

The present invention provides (a) isolated immunogenic HER-2 peptides capable of inducing immune responses against human HER-2 receptor; (b) isolated nucleic acid molecules encoding an isolated immunogenic HER-2 peptide; (c) plasmid constructs comprising a nucleic acid molecule encoding an isolated immunogenic HER-2 peptide; (d) vaccine compositions comprising an isolated immunogenic HER-2 peptide (e) vaccine compositions comprising an isolated nucleic acid molecule encoding an isolated immunogenic HER-2 peptide; and (f) methods of treating or preventing cancer, inhibiting abnormal cell proliferation, or eliciting an immune response against HER-2 protein in a mammal using (1) an isolated immunogenic HER-2 peptide, (2) nucleic acid molecule encoding an isolated immunogenic HER-2 peptide, or (3) a composition comprising an isolated immunogenic HER-2 peptide, or composition comprising a nucleic acid molecule encoding an isolated immunogenic HER-2 peptide.

7 Claims, 2 Drawing Sheets

SEQUENCE LISTING

<160> NUMBER OF SEQ ID NOS: 41

<210> SEQ ID NO 1
<211> LENGTH: 1255
<212> TYPE: PRT
<213> ORGANISM: Homo sapiens

<400> SEQUENCE: 1

```
Met Glu Leu Ala Ala Leu Cys Arg Trp Gly Leu Leu Leu Ala Leu Leu
  1               5                  10                  15

Pro Pro Gly Ala Ala Ser Thr Gln Val Cys Thr Gly Thr Asp Met Lys
             20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
```

```
              340                 345                 350
Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
            690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765
```

```
Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170
```

```
Ser Pro Gly Lys Asn Gly Val Val Lys Asp Val Phe Ala Phe Gly
    1175                1180                1185
Gly Ala Val Glu Asn Pro Glu Tyr Leu Thr Pro Gln Gly Gly Ala
    1190                1195                1200
Ala Pro Gln Pro His Pro Pro Ala Phe Ser Pro Ala Phe Asp
    1205                1210                1215
Asn Leu Tyr Tyr Trp Asp Gln Asp Pro Pro Glu Arg Gly Ala Pro
    1220                1225                1230
Pro Ser Thr Phe Lys Gly Thr Pro Thr Ala Glu Asn Pro Glu Tyr
    1235                1240                1245
Leu Gly Leu Asp Val Pro Val
    1250                1255

<210> SEQ ID NO 2
<211> LENGTH: 3765
<212> TYPE: DNA
<213> ORGANISM: Artificial Sequence
<220> FEATURE:
<223> OTHER INFORMATION: Synthetic Construct

<400> SEQUENCE: 2
```

| | | | | | |
|---|---|---|---|---|---|
| atggagctgg | cggccttgtg | ccgctggggg | ctcctcctcg | ccctcttgcc | ccccggagcc | 60 |
| gcgagcaccc | aagtgtgcac | cggcacagac | atgaagctgc | ggctccctgc | cagtcccgag | 120 |
| acccacctgg | acatgctccg | ccacctctac | cagggctgcc | aggtggtgca | gggaaacctg | 180 |
| gaactcacct | acctgcccac | caatgccagc | ctgtccttcc | tgcaggatat | ccaggaggtg | 240 |
| cagggctacg | tgctcatcgc | tcacaaccaa | gtgaggcagg | tcccactgca | gaggctgcgg | 300 |
| attgtgcgag | gcacccagct | cttcgaggac | aactatgccc | tggccgtgct | agacaatgga | 360 |
| gacccgctga | acaataccac | ccctgtcaca | ggggcctccc | caggaggcct | gcgggagctg | 420 |
| cagcttcgaa | gcctcacaga | gatcttgaaa | ggaggggtct | tgatccagcg | gaaccccccag | 480 |
| ctctgctacc | aggacacgat | tttgtggaag | acatcttcc | acaagaacaa | ccagctggct | 540 |
| ctcacactga | tagacaccaa | ccgctctcgg | gcctgccacc | cctgttctcc | gatgtgtaag | 600 |
| ggctcccgct | gctgggggaga | gagttctgag | gattgtcaga | gcctgacgcg | cactgtctgt | 660 |
| gccggtggct | gtgcccgctg | caaggggcca | ctgcccactg | actgctgcca | tgagcagtgt | 720 |
| gctgccggct | gcacgggccc | caagcactct | gactgcctgg | cctgcctcca | cttcaaccac | 780 |
| agtggcatct | gtgagctgca | ctgcccagcc | ctggtcacct | acaacacaga | cacgtttgag | 840 |
| tccatgccca | atcccgaggg | ccggtataca | ttcggcgcca | gctgtgtgac | tgcctgtccc | 900 |
| tacaactacc | tttctacgga | cgtgggatcc | tgcacccctcg | tctgcccccct | gcacaaccaa | 960 |
| gaggtgacag | cagaggatgg | aacacagcgg | tgtgagaagt | gcagcaagcc | ctgtgcccga | 1020 |
| gtgtgctatg | gtctgggcat | ggagcacttg | cgagaggtga | gggcagttac | cagtgccaat | 1080 |
| atccaggagt | ttgctggctg | caagaagatc | tttgggagcc | tggcatttct | gccggagagc | 1140 |
| tttgatgggg | acccagcctc | caacactgcc | cgctccagc | cagagcagct | ccaagtgttt | 1200 |
| gagactctgg | aagagatcac | aggttaccta | tacatctcag | catggccgga | cagcctgcct | 1260 |
| gacctcagcg | tcttccagaa | cctgcaagta | atccggggac | gaattctgca | caatggcgcc | 1320 |
| tactcgctga | ccctgcaagg | gctgggcatc | agctggctgg | ggctgcgctc | actgagggaa | 1380 |
| ctgggcagtg | gactgccct | catccaccat | aacacccacc | tctgcttcgt | gcacacggtg | 1440 |
| ccctgggacc | agctctttcg | gaacccgcac | caagctctgc | tccacactgc | caaccggcca | 1500 |
| gaggacgagt | gtgtgggcga | gggcctggcc | tgccaccagc | tgtgcgcccg | agggcactgc | 1560 |

```
tggggtccag ggcccaccca gtgtgtcaac tgcagccagt tccttcgggg ccaggagtgc      1620
gtggaggaat gccgagtact gcaggggctc cccaggdagt atgtgaatgc caggcactgt      1680
```

```
tggggtccag ggcccaccca gtgtgtcaac tgcagccagt tccttcgggg ccaggagtgc      1620
gtggaggaat gccgagtact gcaggggctc cccaggdagt atgtgaatgc caggcactgt      1680
ttgccgtgcc accctgagtg tcagcccag aatggctcag tgacctgttt tggaccggag       1740
gctgaccagt gtgtggcctg tgcccactat aaggaccctc ccttctgcgt ggcccgctgc      1800
cccagcggtg tgaaacctga cctctcctac atgcccatct ggaagtttcc agatgaggag      1860
ggcgcatgcc agccttgccc catcaactgc acccactcct gtgtggacct ggatgacaag      1920
ggctgccccg ccgagcagag agccagccct ctgacgtcca tcatctctgc ggtggttggc      1980
attctgctgg tcgtggtctt gggggtggtc tttgggatcc tcatcaagcg acggcagcag      2040
aagatccgga agtacacgat gcggagactg ctgcaggaaa cggagctggt ggagccgctg      2100
acacctagcg gagcgatgcc caaccaggcg cagatgcgga tcctgaaaga gacggagctg      2160
aggaaggtga aggtgcttgg atctggcgct tttggcacag tctacaaggg catctggatc      2220
cctgatgggg agaatgtgaa aattccagtg gccatcaaag tgttgaggga aaacacatcc      2280
cccaaagcca acaaagaaat cttagacgaa gcatacgtga tggctggtgt gggctcccca      2340
tatgtctccc gccttctggg catctgcctg acatccacgg tgcagctggt gacacagctt      2400 atgcctatg gctgcctctt agaccatgtc cgggaaaacc gcggacgcct gggctcccag      2460
gacctgctga actggtgtat gcagattgcc aaggggatga gctacctgga ggatgtgcgg      2520
ctcgtacaca gggacttggc cgctcggaac gtgctggtca gagtcccaa ccatgtcaaa      2580 attacagact cgggctggc tcggctgctg gacattgacg agacagagta ccatgcagat      2640
gggggcaagg tgcccatcaa gtggatggcg ctggagtcca ttctccgccg gcggttcacc      2700
caccagagtg atgtgtggag ttatggtgtg actgtgtggg agctgatgac tttggggcc      2760 aaaccttacg atgggatccc agcccgggag atccctgacc tgctggaaaa gggggagcgg      2820
ctgccccagc cccccatctg caccattgat gtctacatga tcatggtcaa atgttggatg      2880
attgactctg aatgtcggcc aagattccgg gagttggtgt ctgaattctc ccgcatggcc      2940
agggaccccc agcgctttgt ggtcatccag aatgaggact ggggcccagc cagtccctg      3000 gacagcacct tctaccgctc actgctggag gacgatgaca tggggacct ggtggatgct      3060 gaggagtatc tggtacccca gcagggcttc ttctgtccag accctgcccc gggcgctggg      3120
ggcatggtcc accacaggca ccgcagctca tctaccagga gtggcggtgg ggacctgaca      3180
ctagggctgg agccctctga agaggaggcc cccaggtctc cactggcacc ctccgaaggg      3240
gctggctccg atgtatttga tggtgacctg ggaatgggg cagccaaggg gctgcaaagc      3300
ctccccacac atgaccccag ccctctacag cggtacagtg aggaccccac agtacccctg      3360
ccctctgaga ctgatggcta cgttgccccc ctgacctgca gccccagcc tgaatatgtg      3420 aaccagccag atgttcggcc ccagccccct tcgccccgag agggccctct gcctgctgcc      3480
cgacctgctg gtgccactct ggaaaggccc aagactctct cccagggaa gaatgggtc      3540 gtcaaagacg tttttgcctt tgggggtgcc gtggagaacc ccgagtactt gacacccag      3600 ggaggagctg cccctcagcc ccacctcct cctgccttca gcccagcctt cgacaacctc      3660
tattactggg accaggaccc accagagcgg ggggctccac ccagcacctt caaagggaca      3720
cctacggcag agaacccaga gtacctgggt ctggacgtgc cagtg                      3765
```

<210> SEQ ID NO 3
<211> LENGTH: 910
<212> TYPE: PRT

<213> ORGANISM: Artificial Sequence
<220> FEATURE:
<223> OTHER INFORMATION: Synthetic Constructs

<400> SEQUENCE: 3

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Ile Val Arg His
        35                  40                  45

Leu Tyr Gln Gly Cys Gln Val Val Gln Gly Asn Leu Glu Leu Thr Tyr
    50                  55                  60

Val Pro Ala Asn Ala Ser Leu Ser Phe Leu Gln Asp Ile Gln Glu Val
65                  70                  75                  80

Gln Gly Tyr Met Leu Ile Ala His Ser Arg Val Lys His Ile Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Arg Asp Leu Gln Asp Asn Ala Thr Ser
        115                 120                 125

Ala Ala Gly Arg Thr Pro Glu Gly Leu Arg Glu Leu Gln Leu Arg Ser
    130                 135                 140

Leu Thr Glu Ile Leu Lys Gly Gly Val Leu Ile Arg Gly Ser Pro Gln
145                 150                 155                 160

Leu Cys His Gln Asp Met Val Leu Trp Glu Asp Val Leu Arg Lys Asn
                165                 170                 175

Asn Gln Leu Thr Pro Val Asp Met Asp Thr Asn Arg Ser Arg Ala Cys
            180                 185                 190

Pro Pro Cys Ala Pro Ala Cys Arg Asp Asn His Cys Trp Gly Ala Ser
        195                 200                 205

Pro Gly Asp Cys Asn Ser Leu Thr Gly Thr Ile Cys Thr Ser Gly Cys
    210                 215                 220

Ala Arg Cys Lys Gly Arg Gln Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ser Leu Ile
            260                 265                 270

Ile Tyr Asn Thr Asp Thr Phe Glu Ser Met His Asn Pro Glu Gly Arg
        275                 280                 285

Tyr Thr Phe Gly Ala Ser Cys Val Thr Thr Cys Pro Tyr Asn Tyr Leu
    290                 295                 300

Ser Thr Glu Val Gly Ser Cys Thr Leu Val Cys Pro Pro Asn Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Gly
            340                 345                 350

Ala Arg Ala Ile Thr Ser Asp Asn Val Gln Asp Phe Val Gly Cys Lys
        355                 360                 365

Lys Ile Phe Gly Ser Leu Ala Phe Leu Pro Glu Ser Phe Asp Gly Asp
    370                 375                 380

Pro Ser Ser Gly Ile Ala Pro Leu Arg Pro Glu His Leu Arg Val Phe
```

```
            385                 390                 395                 400
Glu Ala Leu Glu Glu Ile Thr Gly Tyr Leu Tyr Ile Ser Ala Trp Pro
                    405                 410                 415

Glu Ser Phe Arg Asn Leu Ser Val Leu Gln Asn Leu Arg Ile Ile Arg
                420                 425                 430

Gly Arg Val Leu His Asp Gly Ala Tyr Ser Leu Ala Leu Gln Gly Leu
            435                 440                 445

Gly Ile Arg Ser Leu Gly Leu Arg Ser Leu Gln Glu Leu Gly Ser Gly
        450                 455                 460

Leu Ala Leu Val His Arg Asn Ala Arg Leu Cys Phe Val Asn Thr Val
465                 470                 475                 480

Pro Trp Ala Gln Leu Phe Arg Asn Pro His Gln Ala Leu Leu His Ser
                485                 490                 495

Gly Asn Pro Ser Glu Asp Glu Cys Gly Leu Lys Asp Phe Val Cys Asn
                500                 505                 510

Ser Leu Cys Ala His Gly His Cys Trp Gly Pro Gly Pro Thr His Cys
            515                 520                 525

Val Asn Cys Ser Gln Phe Leu Pro Gly Gln Glu Cys Val Lys Glu Cys
        530                 535                 540

Arg Val Trp Lys Gly Leu Pro Arg Glu Tyr Val Ser Asp Lys Arg Cys
545                 550                 555                 560

Leu Pro Cys His Ser Glu Cys Gln Pro Gln Asn Ser Thr Glu Thr Cys
                565                 570                 575

Tyr Gly Ser Glu Ala Asp Gln Cys Glu Ala Cys Thr His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Ala Asp Leu Asp Asp Arg
625                 630                 635                 640

Gly Cys Pro Ala Glu Asn Glu Asp Leu Gly Pro Ser Ser Pro Met Asp
                645                 650                 655

Ser Thr Phe Tyr Arg Ser Leu Leu Glu Asp Glu Asp Met Gly Glu Leu
                660                 665                 670

Val Asp Ala Glu Glu Tyr Leu Val Pro Gln Gln Gly Phe Phe Ser Pro
            675                 680                 685

Asp Pro Thr Pro Gly Thr Gly Ser Thr Ala His Arg Arg His Arg Ser
        690                 695                 700

Ser Ser Ala Arg Asn Gly Gly Asp Leu Thr Leu Gly Met Glu Pro
705                 710                 715                 720

Ser Gly Glu Gly Pro Arg Ser Pro Arg Ala Pro Ser Glu Gly Thr
                725                 730                 735

Gly Ser Asp Val Phe Asp Gly Leu Ala Val Gly Val Thr Lys Gly
            740                 745                 750

Leu Gln Ser Leu Ser Pro Gln Asp Leu Ser Pro Leu Gln Arg Tyr Ser
        755                 760                 765

Glu Asp Pro Thr Leu Pro Leu Pro Ser Glu Thr Asp Gly Lys Val Ala
    770                 775                 780

Pro Leu Ser Cys Ser Pro Gln Pro Glu Phe Val Asn Gln Ser Asp Val
785                 790                 795                 800

Gln Pro Lys Ser Pro Leu Thr Pro Glu Gly Pro Ser Pro Ala Arg
                805                 810                 815
```

```
Pro Thr Gly Ala Thr Leu Glu Arg Ala Lys Thr Leu Ser Pro Gly Lys
            820                 825                 830

Asn Gly Val Val Lys Asp Val Phe Thr Phe Gly Ala Val Glu Asn
        835                 840                 845

Pro Glu Phe Leu Ala Pro Arg Glu Gly Thr Ala Ser Pro Pro His Pro
    850                 855                 860

Ser Pro Ala Phe Ser Pro Ala Phe Asp Asn Leu Phe Phe Trp Asp Gln
865                 870                 875                 880

Asn Ser Ser Glu Gln Gly Pro Pro Ser Asn Phe Glu Gly Thr Pro
                885                 890                 895

Thr Ala Glu Asn Pro Glu Phe Leu Gly Leu Asp Val Pro Val
            900                 905                 910
```

<210> SEQ ID NO 4
<211> LENGTH: 2733
<212> TYPE: DNA
<213> ORGANISM: Artificial Sequence
<220> FEATURE:
<223> OTHER INFORMATION: Synthetic Construct

<400> SEQUENCE: 4

```
atggaactgg ccgccctgtg tagatgggga ctgctgctgg ccctgctgcc cctggcgct       60 gcttccacac aggtgtgcac cggcaccgac atgaagctga actgcccgc cagccctgag      120 acccacctgg acatcgtgcg gcacctgtac cagggctgtc aggtggtgca gggcaacctg     180
gaactgacct acgtgccgc caacgccagc ctgagcttcc tgcaggacat ccaggaagtg     240
cagggctaca tgctgatcgc ccacagccgg gtgaagcaca tcccctgca gcggctgaga      300 atcgtgcggg gcacccagct gttcgaggac aactacgccc tggccgtgct ggacaaccgg    360
gacctgcagg ataatgccac ctccgccgct ggcagaacac tgagggcct gcgggagctg     420 cagctgagaa gctgaccga tcctgaag gcggcgtgc tgatcagagg cagcccag         480 ctgtgccatc aggatatggt gctgtgggag gacgtgctgc ggaagaacaa ccagctgacc    540 cccgtgaca tggacaccaa ccggtccaga gcctgccctc cttgcgcccc tgcctgcagg      600
gataaccact gctgggcgc cagcccaggc gattgcaaca gcctgaccgg caccatctgc     660
accagcggct gcgccagatg caagggcaga cagcccaccg actgctgcca tgagcagtgt    720
gccgccggat gtaccggccc aagcacagc gactgcctgg cctgcctgca cttcaaccac    780
agcggcatct gcgagctgca ctgccccagc ctgatcatct acaacaccga ccttcgag     840 agcatgcaca ccccgaggg cagatacacc ttcggcgcca gctgcgtgac cacctgcccc    900
tacaactacc tgagcaccga agtgggcagc tgcacctgg tgtgcccccc aacaaccag     960 gaagtgaccg ccgaggacgg cacccagaga tgcgagaagt gcagcaagcc tgcgccaga    1020 gtgtgttacg gcctgggcat ggaacatctg aggggcgcca gggccatcac cagcgacaac    1080
gtgcaggact cgtgggctg caagaagatt ttcggctccc tggccttcct gcccgagagc    1140
ttcgacggcg accctagcag cggcatcgcc cccctgagac cagagcacct gcgggtgttc    1200
gaggccctgg aagagatcac cggctacctg tacatcagcg cctggccga gtccttccgg    1260 aacctgagcg tgctgcagaa cctgcggatc atccggggca gtgctgca cgatggcgcc     1320 tatagcctcg ctctgcaggg actgggaatc agaagcctgg gcctgcggtc tctgcaggaa    1380
ctgggcagcg actggccct ggtgcaccgg aacgcccggc tgtgcttcgt gaataccgtg    1440
ccctgggccc agctgtttag gaaccccac caggctctgc tgcacagcgg caaccccagc    1500
```

```
gaggacgagt gcggcctgaa ggactttgtg tgcaactccc tgtgcgccca cggacactgt    1560
tggggacctg gacctaccca ctgcgtgaac tgcagccagt ttctgcctgg ccaggaatgc    1620
gtgaaagaat gcagagtgtg aagggcctg cctcgggagt acgtgagcga caagcggtgc    1680
ctgccctgcc acagcgagtg ccagcccag aacagcaccg agacctgcta cggcagcgag    1740
gccgaccagt gtgaggcctg cacccactac aaggaccccc ccttctgcgt ggccagatgc    1800
cctagcggcg tgaagcccga cctgagctac atgcccatct ggaagttccc cgacgaggaa    1860
ggcgcctgcc agccctgccc catcaactgc acccacagct gcgccgacct ggacgataga    1920
ggctgccctg ccgagaacga ggatctgggc ccagcagcc ctatggacag caccttctac    1980
agatccctgc tggaagatga ggacatgggc gaactggtgg acgccgagga ataccctggtg   2040 cctcagcagg gcttcttcag ccccgatcct accctggca ccggcagcac agcccatcgg    2100
cggcacagaa gcagttctgc tagaaatggc ggcggagacc tgaccctggg aatggaacct    2160
agcggcgagg gccctcctag aagccctaga gcaccttccg aagggaccgg ctccgacgtg    2220
ttcgatggcg atctggccgt gggcgtgaca aagggcctgc agtctctctc tccacaggat    2280
ctgtctccac tgcagagata cagcgaggac cccaccctgc ctctgcctag cgagaccgac    2340
ggcaaggtgg cccctctgag ctgtagcccc cagcccgagt cgtgaaacca gagcgacgtg    2400
cagcccaaga gccctctgac ccctgaggga cccctagcc ctgccagacc taccggcgcc    2460 acccctggaaa gagccaagac cctgagcccc ggcaagaacg cgtggtgaa ggacgtgttc    2520 acctttggcg gagccgtgga gaaccctgag ttcctggccc aagagaggg cacagccagc    2580 cctcctcacc ccagcccagc cttcagccct gccttcgaca acctgttctt ctgggaccag    2640
aattctagtg aacagggacc tccacccagc aatttcgagg gcaccccccac cgccgagaat    2700 cccgagtttc tgggcctgga cgtgcccgtg tag                                 2733
```

<210> SEQ ID NO 5
<211> LENGTH: 645
<212> TYPE: PRT
<213> ORGANISM: Artificial Sequence
<220> FEATURE:
<223> OTHER INFORMATION: Synthetic Construct

<400> SEQUENCE: 5

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Ile Val Arg His
        35                  40                  45

Leu Tyr Gln Gly Cys Gln Val Val Gln Gly Asn Leu Glu Leu Thr Tyr
    50                  55                  60

Val Pro Ala Asn Ala Ser Leu Ser Phe Leu Gln Asp Ile Gln Glu Val
65                  70                  75                  80

Gln Gly Tyr Met Leu Ile Ala His Ser Arg Val Lys His Ile Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Arg Asp Leu Gln Asp Asn Ala Thr Ser
        115                 120                 125

Ala Ala Gly Arg Thr Pro Glu Gly Leu Arg Glu Leu Gln Leu Arg Ser
    130                 135                 140
```

```
Leu Thr Glu Ile Leu Lys Gly Gly Val Leu Ile Arg Gly Ser Pro Gln
145                 150                 155                 160

Leu Cys His Gln Asp Met Val Leu Trp Glu Asp Val Leu Arg Lys Asn
                165                 170                 175

Asn Gln Leu Thr Pro Val Asp Met Asp Thr Asn Arg Ser Arg Ala Cys
            180                 185                 190

Pro Pro Cys Ala Pro Ala Cys Arg Asp Asn His Cys Trp Gly Ala Ser
        195                 200                 205

Pro Gly Asp Cys Asn Ser Leu Thr Gly Thr Ile Cys Thr Ser Gly Cys
    210                 215                 220

Ala Arg Cys Lys Gly Arg Gln Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ser Leu Ile
                260                 265                 270

Ile Tyr Asn Thr Asp Thr Phe Glu Ser Met His Asn Pro Glu Gly Arg
            275                 280                 285

Tyr Thr Phe Gly Ala Ser Cys Val Thr Thr Cys Pro Tyr Asn Tyr Leu
        290                 295                 300

Ser Thr Glu Val Gly Ser Cys Thr Leu Val Cys Pro Pro Asn Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Gly
            340                 345                 350

Ala Arg Ala Ile Thr Ser Asp Asn Val Gln Asp Phe Val Gly Cys Lys
        355                 360                 365

Lys Ile Phe Gly Ser Leu Ala Phe Leu Pro Glu Ser Phe Asp Gly Asp
    370                 375                 380

Pro Ser Ser Gly Ile Ala Pro Leu Arg Pro Glu His Leu Arg Val Phe
385                 390                 395                 400

Glu Ala Leu Glu Glu Ile Thr Gly Tyr Leu Tyr Ile Ser Ala Trp Pro
                405                 410                 415

Glu Ser Phe Arg Asn Leu Ser Val Leu Gln Asn Leu Arg Ile Ile Arg
            420                 425                 430

Gly Arg Val Leu His Asp Gly Ala Tyr Ser Leu Ala Leu Gln Gly Leu
        435                 440                 445

Gly Ile Arg Ser Leu Gly Leu Arg Ser Leu Gln Glu Leu Gly Ser Gly
    450                 455                 460

Leu Ala Leu Val His Arg Asn Ala Arg Leu Cys Phe Val Asn Thr Val
465                 470                 475                 480

Pro Trp Ala Gln Leu Phe Arg Asn Pro His Gln Ala Leu Leu His Ser
                485                 490                 495

Gly Asn Pro Ser Glu Asp Glu Cys Gly Leu Lys Asp Phe Val Cys Asn
            500                 505                 510

Ser Leu Cys Ala His Gly His Cys Trp Gly Pro Gly Pro Thr His Cys
        515                 520                 525

Val Asn Cys Ser Gln Phe Leu Pro Gly Gln Glu Cys Val Lys Glu Cys
    530                 535                 540

Arg Val Trp Lys Gly Leu Pro Arg Glu Tyr Val Ser Asp Lys Arg Cys
545                 550                 555                 560

Leu Pro Cys His Ser Glu Cys Gln Pro Gln Asn Ser Thr Glu Thr Cys
```

|  |  |  | 565 |  |  |  | 570 |  |  |  | 575 |  |
|---|---|---|---|---|---|---|---|---|---|---|---|---|
| Tyr | Gly | Ser | Glu | Ala | Asp | Gln | Cys | Glu | Ala | Cys | Thr | His | Tyr | Lys | Asp |
|  |  |  | 580 |  |  |  | 585 |  |  |  | 590 |  |

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
            610                 615                 620

Pro Cys Pro Ile Asn Cys Thr His Ser Cys Ala Asp Leu Asp Asp Arg
625                 630                 635                 640

Gly Cys Pro Ala Glu
            645

<210> SEQ ID NO 6
<211> LENGTH: 1935
<212> TYPE: DNA
<213> ORGANISM: Artificial Sequence
<220> FEATURE:
<223> OTHER INFORMATION: Synthetic Construct

<400> SEQUENCE: 6

```
atggaactgg ccgccctgtg tagatgggga ctgctgctgg ccctgctgcc cctggcgct     60
gcttccacac aggtgtgcac cggcaccgac atgaagctga ctgcccgc cagccctgag    120
acccacctgg acatcgtgcg gcacctgtac cagggctgtc aggtggtgca gggcaacctg    180
gaactgacct acgtgcccgc caacgccagc ctgagcttcc tgcaggacat ccaggaagtg    240
cagggctaca tgctgatcgc ccacagccgg gtgaagcaca tccccctgca gcggctgaga    300
atcgtgcggg gcacccagct gttcgaggac aactacgccc tggccgtgct ggacaaccgg    360
gacctgcagg ataatgccac ctccgccgct ggcagaacac tgagggcct gcgggagctg    420
cagctgagaa gcctgaccga gatcctgaag ggcggcgtgc tgatcagagg cagccccag    480
ctgtgccatc aggatatggt gctgtgggag acgtgctgc ggaagaacaa ccagctgacc    540
cccgtggaca tggacaccaa ccggtccaga gcctgccctc cttgcgcccc tgcctgcagg    600
gataaccact gctggggcgc cagcccaggc gattgcaaca gcctgaccgg caccatctgc    660
accagcggct gcgccagatg caagggcaga cagcccaccg actgctgcca tgagcagtgt    720
gccgccggat gtaccggccc caagcacagc gactgcctgg cctgcctgca cttcaaccac    780
agcggcatct gcgagctgca ctgccccagc ctgatcatct acaacaccga caccttcgag    840
agcatgcaca ccccgaggg cagatacacc ttcggcgcca gctgcgtgac acctgcccc    900
tacaactacc tgagcaccga agtgggcagc tgcaccctgg tgtgcccccc caacaaccag    960
gaagtgaccg ccgaggacgg cacccagaga tgcgagaagt gcagcaagcc ctgcgccaga   1020
gtgtgttacg gcctgggcat ggaacatctg agggcgcca gggccatcac cagcgacaac   1080
gtgcaggact tcgtgggctg caagaagatt ttcggctccc tggccttcct gcccgagagc   1140
ttcgacggcg accctagcag cggcatcgcc ccctgagac cagagcacct gcgggtgttc   1200
gaggccctgg aagagatcac cggctacctg tacatcagcg cctggcccga gtccttccgg   1260
aacctgagcg tgctgcagaa cctgcggatc atcggggca gagtgctgca cgatggcgcc   1320
tatagcctcg ctctgcaggg actgggaatc agaagcctgg gcctgcggtc tctgcaggaa   1380
ctgggcagcg gactggccct ggtgcaccgg aacgcccggc tgtgcttcgt gaataccgtg   1440
ccctgggccc agctgtttag gaaccccac caggctctgc tgcacagcgg caaccccagc   1500
gaggacgagt gcggcctgaa ggactttgtg tgcaactccc tgtgcgccca cggacactgt   1560
```

```
tggggacctg gacctaccca ctgcgtgaac tgcagccagt ttctgcctgg ccaggaatgc      1620
gtgaaagaat gcagagtgtg aagggcctg cctcgggagt acgtgagcga caagcggtgc       1680
ctgccctgcc acagcgagtg ccagcccag aacagcaccg agacctgcta cggcagcgag       1740
gccgaccagt gtgaggcctg cacccactac aaggaccccc ccttctgcgt ggccagatgc      1800
cctagcggcg tgaagcccga cctgagctac atgcccatct ggaagttccc cgacgaggaa      1860
ggcgcctgcc agccctgccc catcaactgc acccacagct cgccgacct ggacgataga       1920 ggctgccctg ccgag                                                        1935
```

<210> SEQ ID NO 7
<211> LENGTH: 265
<212> TYPE: PRT
<213> ORGANISM: Artificial Sequence
<220> FEATURE:
<223> OTHER INFORMATION: Synthetic Construct

<400> SEQUENCE: 7

```
Asn Glu Asp Leu Gly Pro Ser Ser Pro Met Asp Ser Thr Phe Tyr Arg
1               5                   10                  15

Ser Leu Leu Glu Asp Glu Asp Met Gly Glu Leu Val Asp Ala Glu Glu
            20                  25                  30

Tyr Leu Val Pro Gln Gln Gly Phe Phe Ser Pro Asp Pro Thr Pro Gly
        35                  40                  45

Thr Gly Ser Thr Ala His Arg Arg His Arg Ser Ser Ala Arg Asn
    50                  55                  60

Gly Gly Gly Asp Leu Thr Leu Gly Met Glu Pro Ser Gly Glu Gly Pro
65                  70                  75                  80

Pro Arg Ser Pro Arg Ala Pro Ser Glu Gly Thr Gly Ser Asp Val Phe
                85                  90                  95

Asp Gly Asp Leu Ala Val Gly Val Thr Lys Gly Leu Gln Ser Leu Ser
            100                 105                 110

Pro Gln Asp Leu Ser Pro Leu Gln Arg Tyr Ser Glu Asp Pro Thr Leu
        115                 120                 125

Pro Leu Pro Ser Glu Thr Asp Gly Lys Val Ala Pro Leu Ser Cys Ser
    130                 135                 140

Pro Gln Pro Glu Phe Val Asn Gln Ser Asp Val Gln Pro Lys Ser Pro
145                 150                 155                 160

Leu Thr Pro Glu Gly Pro Pro Ser Pro Ala Arg Pro Thr Gly Ala Thr
                165                 170                 175

Leu Glu Arg Ala Lys Thr Leu Ser Pro Gly Lys Asn Gly Val Val Lys
            180                 185                 190

Asp Val Phe Thr Phe Gly Gly Ala Val Glu Asn Pro Glu Phe Leu Ala
        195                 200                 205

Pro Arg Glu Gly Thr Ala Ser Pro Pro His Pro Ser Pro Ala Phe Ser
    210                 215                 220

Pro Ala Phe Asp Asn Leu Phe Pro Trp Asp Gln Asn Ser Ser Glu Gln
225                 230                 235                 240

Gly Pro Pro Pro Ser Asn Phe Glu Gly Thr Pro Thr Ala Glu Asn Pro
                245                 250                 255

Glu Phe Leu Gly Leu Asp Val Pro Val
            260                 265
```

<210> SEQ ID NO 8
<211> LENGTH: 798
<212> TYPE: DNA

<213> ORGANISM: Artificial Sequence
<220> FEATURE:
<223> OTHER INFORMATION: Synthetic Construct

<400> SEQUENCE: 8

```
aacgaggatc tgggcccag cagccctatg acagcacct tctacagatc cctgctggaa    60
gatgaggaca tgggcgaact ggtggacgcc gaggaatacc tggtgcctca gcagggcttc   120
ttcagccccg atcctacccc tggcaccggc agcacagccc atcggcggca cagaagcagt   180
tctgctagaa atggcggcgg agacctgacc ctgggaatgg aacctagcgg cgagggccct   240
cctagaagcc ctagagcacc ttccgaaggg accggctccg acgtgttcga tggcgatctg   300
gccgtgggcg tgacaaaggg cctgcagtct ctctctccac aggatctgtc tccactgcag   360
agatacagcg aggaccccac cctgcctctg cctagcgaga ccgacggcaa ggtggcccct   420
ctgagctgta gccccagcc cgagttcgtg aaccagagcg acgtgcagcc aagagcccct   480
ctgaccctg agggacccc tagccctgcc agacctaccg cgccaccct ggaaagagcc   540
aagaccctga gccccggcaa gaacggcgtg gtgaaggacg tgttcacctt tggcggagcc   600
gtggagaacc tgagttcct ggccccaaga gagggcacag ccagccctcc tcaccccagc   660
ccagccttca gccctgcctt cgacaacctg ttcttctggg accagaattc tagtgaacag   720
ggacctccac ccagcaattt cgagggcacc cccaccgccg agaatcccga gtttctgggc   780
ctggacgtgc ccgtgtag                                                798
```

<210> SEQ ID NO 9
<211> LENGTH: 940
<212> TYPE: PRT
<213> ORGANISM: Artificial Sequence
<220> FEATURE:
<223> OTHER INFORMATION: Synthetic Construct

<400> SEQUENCE: 9

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Ile Val Arg His
        35                  40                  45

Leu Tyr Gln Gly Cys Gln Val Val Gln Gly Asn Leu Glu Leu Thr Tyr
    50                  55                  60

Val Pro Ala Asn Ala Ser Leu Ser Phe Leu Gln Asp Ile Gln Glu Val
65                  70                  75                  80

Gln Gly Tyr Met Leu Ile Ala His Ser Arg Val Lys His Ile Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Arg Asp Leu Gln Asp Asn Ala Thr Ser
        115                 120                 125

Ala Ala Gly Arg Thr Pro Glu Gly Leu Arg Glu Leu Gln Leu Arg Ser
    130                 135                 140

Leu Thr Glu Ile Leu Lys Gly Gly Val Leu Ile Arg Gly Ser Pro Gln
145                 150                 155                 160

Leu Cys His Gln Asp Met Val Leu Trp Glu Asp Val Leu Arg Lys Asn
                165                 170                 175

Asn Gln Leu Thr Pro Val Asp Met Asp Thr Asn Arg Ser Arg Ala Cys
            180                 185                 190
```

```
Pro Pro Cys Ala Pro Ala Cys Arg Asp Asn His Cys Trp Gly Ala Ser
    195                 200                 205
Pro Gly Asp Cys Asn Ser Leu Thr Gly Thr Ile Cys Thr Ser Gly Cys
    210                 215                 220
Ala Arg Cys Lys Gly Arg Gln Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ser Leu Ile
            260                 265                 270
Ile Tyr Asn Thr Asp Thr Phe Glu Ser Met His Asn Pro Glu Gly Arg
        275                 280                 285
Tyr Thr Phe Gly Ala Ser Cys Val Thr Thr Cys Pro Tyr Asn Tyr Leu
    290                 295                 300
Ser Thr Glu Val Gly Ser Cys Thr Leu Val Cys Pro Pro Asn Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Gly
            340                 345                 350
Ala Arg Ala Ile Thr Ser Asp Asn Val Gln Asp Phe Val Gly Cys Lys
        355                 360                 365
Lys Ile Phe Gly Ser Leu Ala Phe Leu Pro Glu Ser Phe Asp Gly Asp
    370                 375                 380
Pro Ser Ser Gly Ile Ala Pro Leu Arg Pro Glu His Leu Arg Val Phe
385                 390                 395                 400
Glu Ala Leu Glu Glu Ile Thr Gly Tyr Leu Tyr Ile Ser Ala Trp Pro
                405                 410                 415
Glu Ser Phe Arg Asn Leu Ser Val Leu Gln Asn Leu Arg Ile Ile Arg
            420                 425                 430
Gly Arg Val Leu His Asp Gly Ala Tyr Ser Leu Ala Leu Gln Gly Leu
        435                 440                 445
Gly Ile Arg Ser Leu Gly Leu Arg Ser Leu Gln Glu Leu Gly Ser Gly
    450                 455                 460
Leu Ala Leu Val His Arg Asn Ala Arg Leu Cys Phe Val Asn Thr Val
465                 470                 475                 480
Pro Trp Ala Gln Leu Phe Arg Asn Pro His Gln Ala Leu Leu His Ser
                485                 490                 495
Gly Asn Pro Ser Glu Asp Glu Cys Gly Leu Lys Asp Phe Val Cys Asn
            500                 505                 510
Ser Leu Cys Ala His Gly His Cys Trp Gly Pro Gly Pro Thr His Cys
        515                 520                 525
Val Asn Cys Ser Gln Phe Leu Pro Gly Gln Glu Cys Val Lys Glu Cys
    530                 535                 540
Arg Val Trp Lys Gly Leu Pro Arg Glu Tyr Val Ser Asp Lys Arg Cys
545                 550                 555                 560
Leu Pro Cys His Ser Glu Cys Gln Pro Gln Asn Ser Thr Glu Thr Cys
                565                 570                 575
Tyr Gly Ser Glu Ala Asp Gln Cys Glu Ala Cys Thr His Tyr Lys Asp
            580                 585                 590
Pro Pro Phe Cys Val Ala Arg Cys Pro Ser Gly Val Lys Pro Asp Leu
        595                 600                 605
```

| Ser | Tyr | Met | Pro | Ile | Trp | Lys | Phe | Pro | Asp | Glu | Glu | Gly | Ala | Cys | Gln |
|     | 610 |     |     |     | 615 |     |     |     |     | 620 |     |     |     |     |     |

| Pro | Cys | Pro | Ile | Asn | Cys | Thr | His | Ser | Cys | Ala | Asp | Leu | Asp | Asp | Arg |
| 625 |     |     |     |     | 630 |     |     |     |     | 635 |     |     |     |     | 640 |

| Gly | Cys | Pro | Ala | Glu | Gln | Arg | Ala | Ser | Pro | Leu | Thr | Ser | Ile | Val | Ser |
|     |     |     |     | 645 |     |     |     |     | 650 |     |     |     |     | 655 |     |

| Ala | Val | Val | Gly | Ile | Leu | Leu | Val | Val | Leu | Gly | Val | Val | Phe | Gly |
|     |     |     | 660 |     |     |     |     | 665 |     |     |     |     | 670 |     |

| Ile | Leu | Ile | Asn | Glu | Asp | Leu | Gly | Pro | Ser | Ser | Pro | Met | Asp | Ser | Thr |
|     |     |     | 675 |     |     |     |     | 680 |     |     |     |     | 685 |     |     |

| Phe | Tyr | Arg | Ser | Leu | Leu | Glu | Asp | Glu | Asp | Met | Gly | Glu | Leu | Val | Asp |
|     | 690 |     |     |     |     | 695 |     |     |     |     | 700 |     |     |     |     |

| Ala | Glu | Glu | Tyr | Leu | Val | Pro | Gln | Gln | Gly | Phe | Phe | Ser | Pro | Asp | Pro |
| 705 |     |     |     |     | 710 |     |     |     |     | 715 |     |     |     |     | 720 |

| Thr | Pro | Gly | Thr | Gly | Ser | Thr | Ala | His | Arg | Arg | His | Arg | Ser | Ser | Ser |
|     |     |     |     | 725 |     |     |     |     | 730 |     |     |     |     | 735 |     |

| Ala | Arg | Asn | Gly | Gly | Gly | Asp | Leu | Thr | Leu | Gly | Met | Glu | Pro | Ser | Gly |
|     |     |     | 740 |     |     |     |     | 745 |     |     |     |     | 750 |     |     |

| Glu | Gly | Pro | Pro | Arg | Ser | Pro | Arg | Ala | Pro | Ser | Glu | Gly | Thr | Gly | Ser |
|     |     | 755 |     |     |     |     | 760 |     |     |     |     | 765 |     |     |     |

| Asp | Val | Phe | Asp | Gly | Asp | Leu | Ala | Val | Gly | Val | Thr | Lys | Gly | Leu | Gln |
| 770 |     |     |     |     | 775 |     |     |     |     | 780 |     |     |     |     |     |

| Ser | Leu | Ser | Pro | Gln | Asp | Leu | Ser | Pro | Leu | Gln | Arg | Tyr | Ser | Glu | Asp |
| 785 |     |     |     |     | 790 |     |     |     |     | 795 |     |     |     |     | 800 |

| Pro | Thr | Leu | Pro | Leu | Pro | Ser | Glu | Thr | Asp | Gly | Lys | Val | Ala | Pro | Leu |
|     |     |     |     | 805 |     |     |     |     | 810 |     |     |     |     | 815 |     |

| Ser | Cys | Ser | Pro | Gln | Pro | Glu | Phe | Val | Asn | Gln | Ser | Asp | Val | Gln | Pro |
|     |     |     | 820 |     |     |     |     | 825 |     |     |     |     | 830 |     |     |

| Lys | Ser | Pro | Leu | Thr | Pro | Glu | Gly | Pro | Pro | Ser | Pro | Ala | Arg | Pro | Thr |
|     |     | 835 |     |     |     |     | 840 |     |     |     |     | 845 |     |     |     |

| Gly | Ala | Thr | Leu | Glu | Arg | Ala | Lys | Thr | Leu | Ser | Pro | Gly | Lys | Asn | Gly |
|     | 850 |     |     |     |     | 855 |     |     |     |     | 860 |     |     |     |     |

| Val | Val | Lys | Asp | Val | Phe | Thr | Phe | Gly | Gly | Ala | Val | Glu | Asn | Pro | Glu |
| 865 |     |     |     |     | 870 |     |     |     |     | 875 |     |     |     |     | 880 |

| Phe | Leu | Ala | Pro | Arg | Glu | Gly | Thr | Ala | Ser | Pro | Pro | His | Pro | Ser | Pro |
|     |     |     |     | 885 |     |     |     |     | 890 |     |     |     |     | 895 |     |

| Ala | Phe | Ser | Pro | Ala | Phe | Asp | Asn | Leu | Phe | Phe | Trp | Asp | Gln | Asn | Ser |
|     |     |     | 900 |     |     |     |     | 905 |     |     |     |     | 910 |     |     |

| Ser | Glu | Gln | Gly | Pro | Pro | Pro | Ser | Asn | Phe | Glu | Gly | Thr | Pro | Thr | Ala |
|     |     | 915 |     |     |     |     | 920 |     |     |     |     | 925 |     |     |     |

| Glu | Asn | Pro | Glu | Phe | Leu | Gly | Leu | Asp | Val | Pro | Val |
|     | 930 |     |     |     |     | 935 |     |     |     | 940 |     |

<210> SEQ ID NO 10
<211> LENGTH: 2820
<212> TYPE: DNA
<213> ORGANISM: Artificial Sequence
<220> FEATURE:
<223> OTHER INFORMATION: Synthetic Construct

<400> SEQUENCE: 10
atggaactgg ccgccctgtg tagatgggga ctgctgctgg ccctgctgcc ccctggcgct    60
gcttccacac aggtgtgcac cggcaccgac atgaagctga actgcccgc cagccctgag   120 acccacctgg acatcgtgcg gcacctgtac cagggctgtc aggtggtgca gggcaacctg   180

-continued

```
gaactgacct acgtgcccgc caacgccagc ctgagcttcc tgcaggacat ccaggaagtg      240
cagggctaca tgctgatcgc ccacagccgg gtgaagcaca tccccctgca gcggctgaga      300
atcgtgcggg gcacccagct gttcgaggac aactacgccc tggccgtgct ggacaaccgg      360
gacctgcagg ataatgccac ctccgccgct ggcagaacac ctgagggcct gcgggagctg      420
cagctgagaa gcctgaccga gatcctgaag ggcggcgtgc tgatcagagg cagcccccag      480
ctgtgccatc aggatatggt gctgtgggag gacgtgctgc ggaagaacaa ccagctgacc      540
cccgtggaca tggacaccaa ccggtccaga gcctgccctc cttgcgcccc tgcctgcagg      600
gataaccact gctggggcgc cagcccaggc gattgcaaca gcctgaccgg caccatctgc      660
accagcggct gcgccagatg caagggcaga cagcccaccg actgctgcca tgagcagtgt      720
gccgccggat gtaccggccc caagcacagc gactgcctgg cctgcctgca cttcaaccac      780
agcggcatct gcgagctgca ctgccccagc ctgatcatct acaacaccga caccttcgag      840
agcatgcaca ccccgaggg cagatacacc ttcggcgcca gctgcgtgac cacctgcccc      900
tacaactacc tgagcaccga agtgggcagc tgcaccctgg tgtgcccccc caacaaccag      960
gaagtgaccg ccgaggacgg cacccagaga tgcgagaagt gcagcaagcc ctgcgccaga     1020
gtgtgttacg gcctgggcat ggaacatctg aggggcgcca gggccatcac cagcgacaac     1080
gtgcaggact cgtgggctg caagaagatt ttcggctccc tggccttcct gcccgagagc     1140
ttcgacggcg accctagcag cggcatcgcc cccctgagac cagagcacct gcgggtgttc     1200
gaggccctgg aagagatcac cggctacctg tacatcagcg cctggcccga gtccttccgg     1260
aacctgagcg tgctgcagaa cctgcggatc atccggggca gagtgctgca cgatggcgcc     1320
tatagcctcg ctctgcaggg actgggaatc agaagcctgg gcctgcggtc tctgcaggaa     1380
ctgggcagcg gactggccct ggtgcaccgg aacgcccggc tgtgcttcgt gaataccgtg     1440
ccctgggccc agctgtttag gaaccccac caggctctgc tgcacagcgg caaccccagc     1500
gaggacgagt gcggcctgaa ggactttgtg tgcaactccc tgtgcgccca cggacactgt     1560
tggggacctg gacctaccca ctgcgtgaac tgcagccagt ttctgcctgg ccaggaatgc     1620
gtgaaagaat gcagagtgtg gaagggcctg cctcgggagt acgtgagcga caagcggtgc     1680 ctgcccctgcc acagcgagtg ccagccccag aacagcaccg agacctgcta cggcagcgag     1740
gccgaccagt gtgaggcctg cacccactac aaggaccccc ccttctgcgt ggccagatgc     1800
cctagcggcg tgaagcccga cctgagctac atgcccatct ggaagttccc cgacgaggaa     1860
ggcgcctgcc agccctgccc catcaactgc acccacagct cgccgacct ggacgataga     1920 ggctgccctg ccgagcagag agccagccct ctgacgtcca tcgtctctgc ggtggttggc     1980
attctgctgg tcgtggtctt gggggtggtc tttgggatcc tcatcaacga ggatctgggc     2040
cccagcagcc ctatggacag caccttctac agatccctgc tggaagatga ggacatgggc     2100
gaactggtgg acgccgagga atacctggtg cctcagcagg gcttcttcag ccccgatcct     2160 accccctggca ccggcagcac agcccatcgg cggcacagaa gcagttctgc tagaaatggc     2220
ggcggagacc tgaccctggg aatggaacct agcggcgagg ccctcctag aagccctaga     2280 gcacttccg aagggaccgg ctccgacgtg ttcgatggcg atctggccgt gggcgtgaca     2340
aagggcctgc agtctctctc tccacaggat ctgtctccac tgcagagata cagcgaggac     2400
ccacccctgc ctctgcctag cgagaccgac ggcaaggtgg cccctctgag ctgtagcccc     2460
cagcccgagt tcgtgaacca gagcgacgtg cagcccaaga gccctctgac ccctgaggga     2520 cccccctagcc ctgccagacc taccggcgcc acccctggaaa gagccaagac cctgagcccc     2580
```

-continued

```
ggcaagaacg gcgtggtgaa ggacgtgttc acctttggcg gagccgtgga gaaccctgag   2640
ttcctggccc caagagaggg cacagccagc cctcctcacc ccagcccagc cttcagccct   2700
gccttcgaca acctgttctt ctgggaccag aattctagtg aacagggacc tccacccagc   2760
aatttcgagg gcaccccac cgccgagaat cccgagtttc tgggcctgga cgtgcccgtg    2820
```

<210> SEQ ID NO 11
<211> LENGTH: 30
<212> TYPE: PRT
<213> ORGANISM: Artificial Sequence
<220> FEATURE:
<223> OTHER INFORMATION: Synthetic Construct

<400> SEQUENCE: 11

```
Gln Arg Ala Ser Pro Leu Thr Ser Ile Val Ser Ala Val Val Gly Ile
1               5                   10                  15

Leu Leu Val Val Val Leu Gly Val Val Phe Gly Ile Leu Ile
            20                  25                  30
```

<210> SEQ ID NO 12
<211> LENGTH: 623
<212> TYPE: PRT
<213> ORGANISM: Artificial Sequence
<220> FEATURE:
<223> OTHER INFORMATION: Synthetic Construct

<400> SEQUENCE: 12

```
Thr Gln Val Cys Thr Gly Thr Asp Met Lys Leu Arg Leu Pro Ala Ser
1               5                   10                  15

Pro Glu Thr His Leu Asp Ile Val Arg His Leu Tyr Gln Gly Cys Gln
            20                  25                  30

Val Val Gln Gly Asn Leu Glu Leu Thr Tyr Val Pro Ala Asn Ala Ser
        35                  40                  45

Leu Ser Phe Leu Gln Asp Ile Gln Glu Val Gln Gly Tyr Met Leu Ile
    50                  55                  60

Ala His Ser Arg Val Lys His Ile Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Arg Asp Leu Gln Asp Asn Ala Thr Ser Ala Ala Gly Arg Thr Pro
            100                 105                 110

Glu Gly Leu Arg Glu Leu Gln Leu Arg Ser Leu Thr Glu Ile Leu Lys
        115                 120                 125

Gly Gly Val Leu Ile Arg Gly Ser Pro Gln Leu Cys His Gln Asp Met
    130                 135                 140

Val Leu Trp Glu Asp Val Leu Arg Lys Asn Asn Gln Leu Thr Pro Val
145                 150                 155                 160

Asp Met Asp Thr Asn Arg Ser Arg Ala Cys Pro Pro Cys Ala Pro Ala
                165                 170                 175

Cys Arg Asp Asn His Cys Trp Gly Ala Ser Pro Gly Asp Cys Asn Ser
            180                 185                 190

Leu Thr Gly Thr Ile Cys Thr Ser Gly Cys Ala Arg Cys Lys Gly Arg
        195                 200                 205

Gln Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240
```

```
Ile Cys Glu Leu His Cys Pro Ser Leu Ile Ile Tyr Asn Thr Asp Thr
            245                 250                 255

Phe Glu Ser Met His Asn Pro Glu Gly Arg Tyr Thr Phe Gly Ala Ser
            260                 265                 270

Cys Val Thr Thr Cys Pro Tyr Asn Tyr Leu Ser Thr Glu Val Gly Ser
            275                 280                 285

Cys Thr Leu Val Cys Pro Pro Asn Asn Gln Glu Val Thr Ala Glu Asp
            290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Gly Ala Arg Ala Ile Thr Ser
            325                 330                 335

Asp Asn Val Gln Asp Phe Val Gly Cys Lys Lys Ile Phe Gly Ser Leu
            340                 345                 350

Ala Phe Leu Pro Glu Ser Phe Asp Gly Asp Pro Ser Ser Gly Ile Ala
            355                 360                 365

Pro Leu Arg Pro Glu His Leu Arg Val Phe Glu Ala Leu Glu Glu Ile
            370                 375                 380

Thr Gly Tyr Leu Tyr Ile Ser Ala Trp Pro Glu Ser Phe Arg Asn Leu
385                 390                 395                 400

Ser Val Leu Gln Asn Leu Arg Ile Ile Arg Gly Arg Val Leu His Asp
            405                 410                 415

Gly Ala Tyr Ser Leu Ala Leu Gln Gly Leu Gly Ile Arg Ser Leu Gly
            420                 425                 430

Leu Arg Ser Leu Gln Glu Leu Gly Ser Gly Leu Ala Leu Val His Arg
            435                 440                 445

Asn Ala Arg Leu Cys Phe Val Asn Thr Val Pro Trp Ala Gln Leu Phe
450                 455                 460

Arg Asn Pro His Gln Ala Leu Leu His Ser Gly Asn Pro Ser Glu Asp
465                 470                 475                 480

Glu Cys Gly Leu Lys Asp Phe Val Cys Asn Ser Leu Cys Ala His Gly
            485                 490                 495

His Cys Trp Gly Pro Gly Pro Thr His Cys Val Asn Cys Ser Gln Phe
            500                 505                 510

Leu Pro Gly Gln Glu Cys Val Lys Glu Cys Arg Val Trp Lys Gly Leu
            515                 520                 525

Pro Arg Glu Tyr Val Ser Asp Lys Arg Cys Leu Pro Cys His Ser Glu
530                 535                 540

Cys Gln Pro Gln Asn Ser Thr Glu Thr Cys Tyr Gly Ser Glu Ala Asp
545                 550                 555                 560

Gln Cys Glu Ala Cys Thr His Tyr Lys Asp Pro Pro Phe Cys Val Ala
            565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
            595                 600                 605

Thr His Ser Cys Ala Asp Leu Asp Asp Arg Gly Cys Pro Ala Glu
            610                 615                 620

<210> SEQ ID NO 13
<211> LENGTH: 1869
<212> TYPE: DNA
<213> ORGANISM: Artificial Sequence
<220> FEATURE:
```

<223> OTHER INFORMATION: Synthetic Construct

<400> SEQUENCE: 13

```
acacaggtgt gcaccggcac cgacatgaag ctgagactgc ccgccagccc tgagacccac    60
ctggacatcg tgcggcacct gtaccagggc tgtcaggtgg tgcagggcaa cctggaactg   120
acctacgtgc ccgccaacgc cagcctgagc ttcctgcagg acatccagga agtgcagggc   180
tacatgctga tcgcccacag ccgggtgaag cacatccccc tgcagcggct gagaatcgtg   240
cggggcaccc agctgttcga ggacaactac gccctggccg tgctggacaa ccgggacctg   300
caggataatg ccacctccgc cgctggcaga cacctgaggg cctgcggga gctgcagctg   360
agaagcctga ccgagatcct gaagggcggc gtgctgatca gaggcagccc ccagctgtgc   420
catcaggata tggtgctgtg ggaggacgtg ctgcggaaga caaccagct gacccccgtg    480
gacatggaca ccaaccggtc cagagcctgc cctccttgcg ccctgcctg cagggataac    540
cactgctggg cgccagccc aggcgattgc aacagcctga ccggcaccat ctgcaccagc    600
ggctgcgcca gatgcaaggg cagacagccc accgactgct gccatgagca gtgtgccgcc   660
ggatgtaccg gccccaagca cagcgactgc ctggcctgcc tgcacttcaa ccacagcggc   720
atctgcgagc tgcactgccc cagcctgatc atctacaaca ccgacacctt cgagagcatg   780
cacaacccg agggcagata caccttcggc gccagctgcg tgaccacctg ccctacaac    840
tacctgagca ccgaagtggg cagctgcacc ctggtgtgcc cccccaacaa ccaggaagtg   900
accgccgagg acggcaccca gagatgcgag aagtgcagca gccctgcgc cagagtgtgt   960
tacgccctgg gcatggaaca tctgaggggc gccagggcca tcaccagcga caacgtgcag  1020
gacttcgtgg gctgcaagaa gattttcggc tccctggcct tcctgcccga gcttcgac   1080
ggcgacccta gcagcggcat cgcccccctg agaccagagc cctgcgggt gttcgaggcc  1140
ctggaagaga tcaccggcta cctgtacatc agcgcctggc ccgagtcctt ccggaacctg  1200
agcgtgctgc agaacctgcg gatcatccgg ggcagagtgc tgcacgatgg cgcctatagc  1260
ctcgctctgc agggactggg aatcagaagc ctgggcctgc ggtctctgca ggaactgggc  1320
agcggactgg ccctggtgca ccggaacgcc cggctgtgct cgtgaatac cgtgccctgg  1380
gcccagctgt ttaggaaccc ccaccaggct ctgctgcaca gcggcaaccc cagcgaggac  1440
gagtgcggcc tgaaggactt tgtgtgcaac tccctgtgcg cccacggaca ctgttgggga  1500
cctggaccta cccactgcgt gaactgcagc cagtttctgc ctggccagga atgcgtgaaa  1560
gaatgcagag tgtggaaggg cctgcctcgg gagtacgtga cgacaagcg gtgcctgccc  1620
tgccacagcg agtgccagcc ccagaacagc accgagacct gctacggcag cgaggccgac  1680
cagtgtgagg cctgcacca ctacaaggac ccccccttct gcgtggccag atgccctagc  1740
ggcgtgaagc ccgacctgag ctacatgccc atctggaagt tccccgacga ggaaggcgcc  1800
tgccagccct gccccatcaa ctgcacccac agctgcgccg acctggacga tagaggctgc  1860
cctgccgag                                                           1869
```

<210> SEQ ID NO 14
<211> LENGTH: 647
<212> TYPE: PRT
<213> ORGANISM: Artificial Sequence
<220> FEATURE:
<223> OTHER INFORMATION: Synthetic Construct

<400> SEQUENCE: 14

Met Ala Ser Glu Leu Ala Ala Leu Cys Arg Trp Gly Leu Leu Leu Ala

-continued

```
1               5                    10                    15
Leu Leu Pro Pro Gly Ala Ala Ser Thr Gln Val Cys Thr Gly Thr Asp
                20                  25                  30
Met Lys Leu Arg Leu Pro Ala Ser Pro Glu Thr His Leu Asp Met Leu
                35                  40                  45
Arg His Leu Tyr Gln Gly Cys Gln Val Val Gln Asn Leu Glu Leu
    50                  55                  60
Thr Tyr Leu Pro Thr Asn Ala Ser Leu Ser Phe Leu Gln Asp Ile Gln
65                  70                  75                  80
Glu Val Gln Gly Tyr Val Leu Ile Ala His Asn Gln Val Arg Gln Val
                85                  90                  95
Pro Leu Gln Arg Leu Arg Ile Val Arg Gly Thr Gln Leu Phe Glu Asp
                100                 105                 110
Asn Tyr Ala Leu Ala Val Leu Asp Asn Gly Asp Pro Leu Asp Ser Val
                115                 120                 125
Ala Pro Ala Ala Gly Ala Thr Pro Gly Gly Leu Gln Glu Leu Gln Leu
                130                 135                 140
Arg Ser Leu Thr Glu Ile Leu Lys Gly Gly Val Leu Ile Arg Arg Ser
145                 150                 155                 160
Pro Gln Leu Cys His Gln Asp Thr Val Leu Trp Glu Asp Val Phe Arg
                165                 170                 175
Lys Asn Asn Gln Leu Ala Leu Val Leu Met Asp Thr Asn Arg Ser Arg
                180                 185                 190
Ala Cys His Pro Cys Ala Pro Met Cys Lys Ala Asn His Cys Trp Gly
                195                 200                 205
Glu Ser Ser Gln Asp Cys Gln Thr Leu Thr Arg Thr Ile Cys Thr Ser
                210                 215                 220
Ala Cys Ala Arg Cys Lys Ala Pro Leu Pro Thr Asp Cys Cys His Glu
225                 230                 235                 240
Gln Cys Ala Ala Gly Cys Thr Gly Pro Lys His Ser Asp Cys Leu Ala
                245                 250                 255
Cys Leu His Phe Asn His Ser Gly Ile Cys Glu Leu His Cys Pro Ala
                260                 265                 270
Leu Val Thr Tyr Asn Thr Asp Thr Phe Glu Ser Met Pro Asn Pro Glu
                275                 280                 285
Gly Arg Tyr Thr Phe Gly Ala Ser Cys Val Thr Ala Cys Pro Tyr Asn
                290                 295                 300
Tyr Leu Ser Thr Asp Val Gly Ser Cys Thr Leu Val Cys Pro Leu His
305                 310                 315                 320
Asn Gln Glu Val Thr Ala Glu Asp Gly Thr Gln Arg Cys Glu Lys Cys
                325                 330                 335
Ser Lys Pro Cys Ala Arg Val Cys Tyr Gly Leu Gly Met Glu His Leu
                340                 345                 350
Arg Glu Ala Arg Ala Ile Thr Ser Ala Asn Val Gln Asp Phe Val Gly
                355                 360                 365
Cys Lys Lys Ile Phe Gly Ser Leu Ala Phe Leu Pro Glu Ser Phe Asp
                370                 375                 380
Gly Asp Pro Ala Ser Gly Thr Ala Pro Leu Gln Pro Glu Gln Leu Gln
385                 390                 395                 400
Val Phe Glu Thr Leu Glu Glu Ile Thr Gly Tyr Leu Tyr Ile Ser Ala
                405                 410                 415
Trp Pro Asp Ser Phe Pro Asn Leu Ser Val Phe Gln Asn Leu Arg Val
                420                 425                 430
```

Ile Arg Gly Arg Ile Leu His Asn Gly Ala Tyr Ser Leu Thr Leu Gln
        435                 440                 445

Gly Leu Gly Ile Ser Trp Leu Gly Leu Arg Ser Leu Gln Glu Leu Gly
        450                 455                 460

Ser Gly Leu Ala Leu Val His Arg Asn Ala Arg Leu Cys Phe Val His
465                 470                 475                 480

Thr Val Pro Trp Asp Gln Leu Phe Arg Asn Pro His Gln Ala Leu Leu
                485                 490                 495

His Ser Gly Asn Arg Pro Glu Glu Asp Cys Val Gly Glu Gly Phe Val
                500                 505                 510

Cys Tyr Ser Leu Cys Ala His Gly His Cys Trp Gly Pro Gly Pro Thr
                515                 520                 525

Gln Cys Val Asn Cys Ser His Phe Leu Arg Gly Gln Glu Cys Val Glu
        530                 535                 540

Glu Cys Arg Val Leu Gln Gly Leu Pro Arg Glu Tyr Val Asn Ala Arg
545                 550                 555                 560

His Cys Leu Pro Cys His Pro Glu Cys Gln Pro Gln Asn Gly Ser Val
                565                 570                 575

Thr Cys Phe Gly Pro Glu Ala Asp Gln Cys Val Ala Cys Ala His Tyr
        580                 585                 590

Lys Asp Pro Pro Phe Cys Val Ala Arg Cys Pro Ser Gly Val Lys Pro
                595                 600                 605

Asp Leu Ser Tyr Met Pro Ile Trp Lys Phe Pro Asp Glu Glu Gly Ala
        610                 615                 620

Cys Gln Pro Cys Pro Ile Asn Cys Thr His Ser Cys Val Asp Leu Asp
625                 630                 635                 640

Asp Lys Gly Cys Pro Ala Glu
                645

<210> SEQ ID NO 15
<211> LENGTH: 1941
<212> TYPE: DNA
<213> ORGANISM: Artificial Sequence
<220> FEATURE:
<223> OTHER INFORMATION: Synthetic Construct

<400> SEQUENCE: 15

| | | | | | |
|---|---|---|---|---|---|
| atggctagcg | agctggccgc | cctgtgtaga | tggggactgc | tgctggctct | gctgcctcct | 60 |
| ggagccgctt | ctacacaggt | ctgcaccggc | accgacatga | agctgagact | gcccgccagc | 120 |
| cccgagacac | acctggacat | gctgcggcac | ctgtaccagg | gctgccaggt | ggtccagggg | 180 |
| aatctggaac | tgacctacct | gcccaccaac | gccagcctga | gcttcctgca | ggacatccag | 240 |
| gaagtgcagg | gctacgtcct | gatcgcccac | aaccaggtcc | gccaggtgcc | cctgcagcgg | 300 |
| ctgagaatcg | tgcggggcac | ccagctgttc | gaggacaact | acgccctggc | cgtgctggac | 360 |
| aacggcgacc | ctctggatag | cgtggcccct | gctgctgggg | ctacacctgg | cggactgcag | 420 |
| gaactgcagc | tgcggagcct | gaccgagatc | ctgaagggcg | gcgtgctgat | caggcggagc | 480 |
| cctcagctgt | gccaccagga | caccgtgctg | tgggaggacg | tgttccggaa | gaacaaccag | 540 |
| ctggcccctcg | tgctgatgga | caccaacaga | agcgggcct | gccacccctg | cgcccccatg | 600 |
| tgcaaggcca | atcactgctg | gggagagagc | agccaggact | gccagaccct | gacccggacc | 660 |
| atctgcacca | cgcctgcgc | cagatgcaag | gcccccctgc | ctaccgactg | ctgccacgaa | 720 |
| cagtgcgccg | ctggctgcac | cggccccaag | cacagcgatt | gcctggcctg | cctgcacttc | 780 |

```
aaccacagcg gcatctgcga gctgcactgc cctgccctgg tgacatacaa caccgacacc    840
ttcgagagca tgcccaaccc cgagggccgg tacaccttcg gcgccagctg tgtgaccgcc    900
tgcccctaca actacctgag caccgacgtg ggcagctgca ccctggtgtg ccccctgcac    960
aaccaggaag tgaccgccga ggacggcacc cagagatgcg agaagtgcag caagccttgc   1020
gccagagtgt gctacggcct gggcatggaa cacctgagag aggccagagc catcaccagc   1080
gccaacgtgc aggacttcgt gggctgcaag aagattttcg gctccctggc cttcctgccc   1140
gagagcttcg acggcgatcc tgcctctggc accgcccctc tgcagcctga gcagctgcag   1200
gtcttcgaga cactggaaga gatcaccggc tacctgtaca tcagcgcctg gcccgacagc   1260
ttccccaacc tgagcgtgtt ccagaacctg agagtgatcc ggggcagaat cctgcacaac   1320
ggcgcctaca gcctgaccct gcagggcctg gaatcagct ggctgggcct gcggagcctg   1380
caggaactgg gatctggcct ggctctggtg accggaacg cccggctgtg cttcgtgcac   1440
accgtgccct gggaccagct gttcagaaac ccccaccagg ctctgctgca gcgcggcaac   1500
cggcccgaag aggattgcgt gggcgagggc ttcgtgtgct actccctgtg cgcccacggc   1560
cactgttggg gacctggccc tacccagtgc gtgaactgca gccacttcct gcggggccaa   1620
gaatgcgtga agagtgccg ggtgctgcag ggactgcccc gggaatacgt gaacgccaga   1680
cactgcctgc cttgccaccc cgagtgccag ccccagaatg gcagcgtgac ctgcttcgga   1740
cccgaggccg atcagtgtgt ggcctgcgcc cactacaagg acccccatt ctgcgtggcc   1800 agatgcccca gcggcgtgaa gcccgacctg agctacatgc ccatctggaa gttccccgac   1860
gaggaaggcg cctgccagcc ttgccccatc aactgcaccc acagctgcgt ggacctggac   1920
gacaagggct gccctgccga g                                             1941
```

<210> SEQ ID NO 16
<211> LENGTH: 44
<212> TYPE: PRT
<213> ORGANISM: Artificial Sequence
<220> FEATURE:
<223> OTHER INFORMATION: Synthetic Construct

<400> SEQUENCE: 16

Gln Arg Ala Ser Pro Leu Thr Ser Ile Ile Ser Ala Val Val Gly Ile
1               5                   10                  15

Leu Leu Val Val Val Leu Gly Val Val Phe Gly Ile Leu Ile Lys Arg
            20                  25                  30

Arg Gln Gln Lys Ile Arg Lys Tyr Thr Met Arg Arg
        35                  40

<210> SEQ ID NO 17
<211> LENGTH: 132
<212> TYPE: DNA
<213> ORGANISM: Artificial Sequence
<220> FEATURE:
<223> OTHER INFORMATION: Synthetic Construct

<400> SEQUENCE: 17

```
cagagagcca gccccctgac cagcatcatc agcgccgtgg tgggaatcct gctggtggtg     60
gtgctgggcg tggtgttcgg catcctgatc aagcggcgg agcagaagat ccggaagtac    120
accatgcggc gg                                                        132
```

<210> SEQ ID NO 18
<211> LENGTH: 912
<212> TYPE: PRT

<213> ORGANISM: Artificial Sequence
<220> FEATURE:
<223> OTHER INFORMATION: Synthetic Constructs

<400> SEQUENCE: 18

```
Met Ala Ser Glu Leu Ala Ala Leu Cys Arg Trp Gly Leu Leu Leu Ala
1               5                   10                  15

Leu Leu Pro Pro Gly Ala Ala Ser Thr Gln Val Cys Thr Gly Thr Asp
            20                  25                  30

Met Lys Leu Arg Leu Pro Ala Ser Pro Glu Thr His Leu Asp Met Leu
        35                  40                  45

Arg His Leu Tyr Gln Gly Cys Gln Val Val Gln Gly Asn Leu Glu Leu
    50                  55                  60

Thr Tyr Leu Pro Thr Asn Ala Ser Leu Ser Phe Leu Gln Asp Ile Gln
65                  70                  75                  80

Glu Val Gln Gly Tyr Val Leu Ile Ala His Asn Gln Val Arg Gln Val
                85                  90                  95

Pro Leu Gln Arg Leu Arg Ile Val Arg Gly Thr Gln Leu Phe Glu Asp
            100                 105                 110

Asn Tyr Ala Leu Ala Val Leu Asp Asn Gly Asp Pro Leu Asp Ser Val
        115                 120                 125

Ala Pro Ala Ala Gly Ala Thr Pro Gly Gly Leu Gln Glu Leu Gln Leu
    130                 135                 140

Arg Ser Leu Thr Glu Ile Leu Lys Gly Gly Val Leu Ile Arg Arg Ser
145                 150                 155                 160

Pro Gln Leu Cys His Gln Asp Thr Val Leu Trp Glu Asp Val Phe Arg
                165                 170                 175

Lys Asn Asn Gln Leu Ala Leu Val Leu Met Asp Thr Asn Arg Ser Arg
            180                 185                 190

Ala Cys His Pro Cys Ala Pro Met Cys Lys Ala Asn His Cys Trp Gly
        195                 200                 205

Glu Ser Ser Gln Asp Cys Gln Thr Leu Thr Arg Thr Ile Cys Thr Ser
    210                 215                 220

Ala Cys Ala Arg Cys Lys Ala Pro Leu Pro Thr Asp Cys Cys His Glu
225                 230                 235                 240

Gln Cys Ala Ala Gly Cys Thr Gly Pro Lys His Ser Asp Cys Leu Ala
                245                 250                 255

Cys Leu His Phe Asn His Ser Gly Ile Cys Glu Leu His Cys Pro Ala
            260                 265                 270

Leu Val Thr Tyr Asn Thr Asp Thr Phe Glu Ser Met Pro Asn Pro Glu
        275                 280                 285

Gly Arg Tyr Thr Phe Gly Ala Ser Cys Val Thr Ala Cys Pro Tyr Asn
    290                 295                 300

Tyr Leu Ser Thr Asp Val Gly Ser Cys Thr Leu Val Cys Pro Leu His
305                 310                 315                 320

Asn Gln Glu Val Thr Ala Glu Asp Gly Thr Gln Arg Cys Glu Lys Cys
                325                 330                 335

Ser Lys Pro Cys Ala Arg Val Cys Tyr Gly Leu Gly Met Glu His Leu
            340                 345                 350

Arg Glu Ala Arg Ala Ile Thr Ser Ala Asn Val Gln Asp Phe Val Gly
        355                 360                 365

Cys Lys Lys Ile Phe Gly Ser Leu Ala Phe Leu Pro Glu Ser Phe Asp
    370                 375                 380

Gly Asp Pro Ala Ser Gly Thr Ala Pro Leu Gln Pro Glu Gln Leu Gln
```

```
            385                 390                 395                 400

Val Phe Glu Thr Leu Glu Glu Ile Thr Gly Tyr Leu Tyr Ile Ser Ala
                    405                 410                 415

Trp Pro Asp Ser Phe Pro Asn Leu Ser Val Phe Gln Asn Leu Arg Val
                420                 425                 430

Ile Arg Gly Arg Ile Leu His Asn Gly Ala Tyr Ser Leu Thr Leu Gln
            435                 440                 445

Gly Leu Gly Ile Ser Trp Leu Gly Leu Arg Ser Leu Gln Glu Leu Gly
        450                 455                 460

Ser Gly Leu Ala Leu Val His Arg Asn Ala Arg Leu Cys Phe Val His
465                 470                 475                 480

Thr Val Pro Trp Asp Gln Leu Phe Arg Asn Pro His Gln Ala Leu Leu
                485                 490                 495

His Ser Gly Asn Arg Pro Glu Glu Asp Cys Val Gly Glu Gly Phe Val
            500                 505                 510

Cys Tyr Ser Leu Cys Ala His Gly His Cys Trp Gly Pro Gly Pro Thr
        515                 520                 525

Gln Cys Val Asn Cys Ser His Phe Leu Arg Gly Gln Glu Cys Val Glu
    530                 535                 540

Glu Cys Arg Val Leu Gln Gly Leu Pro Arg Glu Tyr Val Asn Ala Arg
545                 550                 555                 560

His Cys Leu Pro Cys His Pro Glu Cys Gln Pro Gln Asn Gly Ser Val
                565                 570                 575

Thr Cys Phe Gly Pro Glu Ala Asp Gln Cys Val Ala Cys Ala His Tyr
            580                 585                 590

Lys Asp Pro Pro Phe Cys Val Ala Arg Cys Pro Ser Gly Val Lys Pro
        595                 600                 605

Asp Leu Ser Tyr Met Pro Ile Trp Lys Phe Pro Asp Glu Glu Gly Ala
    610                 615                 620

Cys Gln Pro Cys Pro Ile Asn Cys Thr His Ser Cys Val Asp Leu Asp
625                 630                 635                 640

Asp Lys Gly Cys Pro Ala Glu Asn Glu Asp Leu Gly Pro Ser Ser Pro
                645                 650                 655

Met Asp Ser Thr Phe Tyr Arg Ser Leu Leu Glu Asp Glu Asp Met Gly
            660                 665                 670

Glu Leu Val Asp Ala Glu Glu Tyr Leu Val Pro Gln Gln Gly Phe Phe
        675                 680                 685

Cys Pro Asp Pro Thr Pro Gly Thr Gly Ser Thr Ala His Arg Arg His
    690                 695                 700

Arg Ser Ser Ser Ala Arg Asn Gly Gly Gly Asp Leu Thr Leu Gly Met
705                 710                 715                 720

Glu Pro Ser Gly Glu Gly Pro Pro Arg Ser Pro Arg Ala Pro Ser Glu
                725                 730                 735

Gly Thr Gly Ser Asp Val Phe Asp Gly Asp Leu Ala Val Gly Val Thr
            740                 745                 750

Lys Gly Leu Gln Ser Leu Ser Pro Gln Asp Leu Ser Pro Leu Gln Arg
        755                 760                 765

Tyr Ser Glu Asp Pro Thr Leu Pro Leu Pro Ser Glu Thr Asp Gly Lys
    770                 775                 780

Val Ala Pro Leu Ser Cys Ser Pro Gln Pro Glu Phe Val Asn Gln Ser
785                 790                 795                 800

Asp Val Gln Pro Lys Ser Pro Leu Thr Pro Glu Gly Pro Pro Ser Pro
                805                 810                 815
```

Ala Arg Pro Thr Gly Ala Thr Leu Glu Arg Ala Lys Thr Leu Ser Pro
        820                 825                 830

Gly Lys Asn Gly Val Val Lys Asp Val Phe Thr Phe Gly Ala Val
            835                 840                 845

Glu Asn Pro Glu Phe Leu Ala Pro Arg Glu Gly Thr Ala Ser Pro Pro
        850                 855                 860

His Pro Ser Pro Ala Phe Ser Pro Ala Phe Asp Asn Leu Phe Phe Trp
865                 870                 875                 880

Asp Gln Asn Ser Ser Glu Gln Gly Pro Pro Ser Asn Phe Glu Gly
                885                 890                 895

Thr Pro Thr Ala Glu Asn Pro Glu Phe Leu Gly Leu Asp Val Pro Val
        900                 905                 910

<210> SEQ ID NO 19
<211> LENGTH: 2739
<212> TYPE: DNA
<213> ORGANISM: Artificial Sequence
<220> FEATURE:
<223> OTHER INFORMATION: Synthetic Construct

<400> SEQUENCE: 19

| | |
|---|---|
| atggctagcg agctggccgc cctgtgtaga tggggactgc tgctggctct gctgcctcct | 60 |
| ggagccgctt ctacacaggt ctgcaccggc accgacatga agctgagact gcccgccagc | 120 |
| cccgagacac acctggacat gctgcggcac ctgtaccagg gctgccaggt ggtccagggg | 180 |
| aatctggaac tgacctacct gcccaccaac gccagcctga gcttcctgca ggacatccag | 240 |
| gaagtgcagg gctacgtcct gatcgcccac aaccaggtcc gccaggtgcc cctgcagcgg | 300 |
| ctgagaatcg tgcggggcac ccagctgttc gaggacaact acgccctggc cgtgctggac | 360 |
| aacggcgacc ctctggatag cgtggcccct gctgctgggg ctacacctgg cggactgcag | 420 |
| gaactgcagc tgcggagcct gaccgagatc ctgaagggcg gcgtgctgat caggcggagc | 480 |
| cctcagctgt gccaccagga caccgtgctg tgggaggacg tgttccggaa gaacaaccag | 540 |
| ctggccctcg tgctgatgga caccaacaga agccgggcct gccaccctg cgcccccatg | 600 |
| tgcaaggcca atcactgctg gggagagagc agccaggact gccagaccct gacccggacc | 660 |
| atctgcacca cgcgcctgcg cagatgcaag gccccctgc ctaccgactg ctgccacgaa | 720 |
| cagtgcgccg ctggctgcac cggccccaag cacagcgatt gcctggcctg cctgcacttc | 780 |
| aaccacagcg gcatctgcga gctgcactgc cctgccctgg tgacatacaa caccgacacc | 840 |
| ttcgagagca tgcccaaccc cgagggccgg tacaccttcg cgccagctg tgtgaccgcc | 900 |
| tgccccctaca actacctgag caccgacgtg ggcagctgca cctggtgtg cccctgcac | 960 |
| aaccaggaag tgaccgccga ggacggcacc cagagatgcg agaagtgcag caagccttgc | 1020 |
| gccagagtgt gctacggcct gggcatggaa cacctgagag aggccagagc catcaccagc | 1080 |
| gccaacgtgc aggacttcgt gggctgcaag aagattttcg gctccctggc cttcctgccc | 1140 |
| gagagcttcg acggcgatcc tgcctctggc accgccctc tgcagcctga gcagctgcag | 1200 |
| gtcttcgaga cactggaaga gatcaccggc tacctgtaca tcagcgcctg gcccgacagc | 1260 |
| ttcccccaacc tgagcgtgtt ccagaacctg agagtgatcc ggggcagaat cctgcacaac | 1320 |
| ggcgcctaca gcctgaccct gcagggcctg ggaatcagct ggctgggcct gcggagcctg | 1380 |
| caggaactgg gatctggcct ggctctggtg caccggaacg cccggctgtg cttcgtgcac | 1440 |
| accgtgccct gggaccagct gttcagaaac ccccaccagg ctctgctgca cagcggcaac | 1500 |

```
cggcccgaag aggattgcgt gggcgagggc ttcgtgtgct actccctgtg cgcccacggc    1560
cactgttggg gacctggccc tacccagtgc gtgaactgca gccacttcct gcggggccaa    1620
gaatgcgtgg aagagtgccg ggtgctgcag ggactgcccc gggaatacgt gaacgccaga    1680
cactgcctgc cttgccaccc cgagtgccag ccccagaatg gcagcgtgac ctgcttcgga    1740
cccgaggccg atcagtgtgt ggcctgcgcc cactacaagg accccccatt ctgcgtggcc    1800
agatgcccca gcggcgtgaa gcccgacctg agctacatgc ccatctggaa gttccccgac    1860
gaggaaggcg cctgccagcc ttgccccatc aactgcaccc acagctgcgt ggacctggac    1920
gacaagggct gccctgccga gaacgaggac ctgggcccct ctagcccat ggacagcacc    1980 ttctaccggt ccctgctgga agatgaggac atgggcgagc tggtggacgc cgaggaatac    2040
ctggtgcctc agcagggctt cttctgcccc gaccctaccc tggcaccgg ctctaccgcc    2100 cacagacggc acagaagcag cagcgccaga acggcggag gcgacctgac cctgggaatg    2160
gaacctagcg gcgagggacc tcccagaagc cctagagccc ctagcgaggg caccggcagc    2220
gacgtgttcg atggcgatct ggccgtgggc gtgaccaagg actgcagag cctgagcccc    2280 caggacctgt cccccctgca gagatacagc gaggacccca ccctgcccct gccagcgag    2340 acagatggca aggtggcccc cctgagctgc agccctcagc ccgagttcgt gaaccagagc    2400
gacgtgcagc ccaagtcccc cctgacaccc gagggacctc caagccctgc agacctacc    2460 ggcgccaccc tggaaagagc caagaccctg agccccggca gaacggcgt ggtgaaagac    2520 gtgttcacct tcggaggcgc cgtggaaaac cccgagttcc tggcccccag agagggcaca    2580
gccagccctc acaccccag cccagccttc tcccccgcct tcgacaacct gttcttctgg    2640
gaccagaaca gcagcgagca gggcccaccc ccagcaatt tcgagggcac ccccaccgcc    2700
gagaatcctg agttcctggg cctggacgtg cccgtgtga                          2739

<210> SEQ ID NO 20
<211> LENGTH: 956
<212> TYPE: PRT
<213> ORGANISM: Artificial Sequence
<220> FEATURE:
<223> OTHER INFORMATION: Synthetic Construct

<400> SEQUENCE: 20

Met Ala Ser Glu Leu Ala Ala Leu Cys Arg Trp Gly Leu Leu Leu Ala
1               5                   10                  15

Leu Leu Pro Pro Gly Ala Ala Ser Thr Gln Val Cys Thr Gly Thr Asp
            20                  25                  30

Met Lys Leu Arg Leu Pro Ala Ser Pro Glu Thr His Leu Asp Met Leu
        35                  40                  45

Arg His Leu Tyr Gln Gly Cys Gln Val Val Gln Gly Asn Leu Glu Leu
    50                  55                  60

Thr Tyr Leu Pro Thr Asn Ala Ser Leu Ser Phe Leu Gln Asp Ile Gln
65                  70                  75                  80

Glu Val Gln Gly Tyr Val Leu Ile Ala His Asn Gln Val Arg Gln Val
                85                  90                  95

Pro Leu Gln Arg Leu Arg Ile Val Arg Gly Thr Gln Leu Phe Glu Asp
            100                 105                 110

Asn Tyr Ala Leu Ala Val Leu Asp Asn Gly Asp Pro Leu Asp Ser Val
        115                 120                 125

Ala Pro Ala Ala Gly Ala Thr Pro Gly Gly Leu Gln Glu Leu Gln Leu
    130                 135                 140
```

```
Arg Ser Leu Thr Glu Ile Leu Lys Gly Gly Val Leu Ile Arg Arg Ser
145                 150                 155                 160

Pro Gln Leu Cys His Gln Asp Thr Val Leu Trp Glu Asp Val Phe Arg
            165                 170                 175

Lys Asn Asn Gln Leu Ala Leu Val Leu Met Asp Thr Asn Arg Ser Arg
                180                 185                 190

Ala Cys His Pro Cys Ala Pro Met Cys Lys Ala Asn His Cys Trp Gly
        195                 200                 205

Glu Ser Ser Gln Asp Cys Gln Thr Leu Thr Arg Thr Ile Cys Thr Ser
    210                 215                 220

Ala Cys Ala Arg Cys Lys Ala Pro Leu Pro Thr Asp Cys Cys His Glu
225                 230                 235                 240

Gln Cys Ala Ala Gly Cys Thr Gly Pro Lys His Ser Asp Cys Leu Ala
            245                 250                 255

Cys Leu His Phe Asn His Ser Gly Ile Cys Glu Leu His Cys Pro Ala
                260                 265                 270

Leu Val Thr Tyr Asn Thr Asp Thr Phe Glu Ser Met Pro Asn Pro Glu
        275                 280                 285

Gly Arg Tyr Thr Phe Gly Ala Ser Cys Val Thr Ala Cys Pro Tyr Asn
    290                 295                 300

Tyr Leu Ser Thr Asp Val Gly Ser Cys Thr Leu Val Cys Pro Leu His
305                 310                 315                 320

Asn Gln Glu Val Thr Ala Glu Asp Gly Thr Gln Arg Cys Glu Lys Cys
            325                 330                 335

Ser Lys Pro Cys Ala Arg Val Cys Tyr Gly Leu Gly Met Glu His Leu
        340                 345                 350

Arg Glu Ala Arg Ala Ile Thr Ser Ala Asn Val Gln Asp Phe Val Gly
    355                 360                 365

Cys Lys Lys Ile Phe Gly Ser Leu Ala Phe Leu Pro Glu Ser Phe Asp
370                 375                 380

Gly Asp Pro Ala Ser Gly Thr Ala Pro Leu Gln Pro Glu Gln Leu Gln
385                 390                 395                 400

Val Phe Glu Thr Leu Glu Glu Ile Thr Gly Tyr Leu Tyr Ile Ser Ala
            405                 410                 415

Trp Pro Asp Ser Phe Pro Asn Leu Ser Val Phe Gln Asn Leu Arg Val
        420                 425                 430

Ile Arg Gly Arg Ile Leu His Asn Gly Ala Tyr Ser Leu Thr Leu Gln
    435                 440                 445

Gly Leu Gly Ile Ser Trp Leu Gly Leu Arg Ser Leu Gln Glu Leu Gly
    450                 455                 460

Ser Gly Leu Ala Leu Val His Arg Asn Ala Arg Leu Cys Phe Val His
465                 470                 475                 480

Thr Val Pro Trp Asp Gln Leu Phe Arg Asn Pro His Gln Ala Leu Leu
            485                 490                 495

His Ser Gly Asn Arg Pro Glu Glu Asp Cys Val Gly Glu Gly Phe Val
        500                 505                 510

Cys Tyr Ser Leu Cys Ala His Gly His Cys Trp Gly Pro Gly Pro Thr
    515                 520                 525

Gln Cys Val Asn Cys Ser His Phe Leu Arg Gly Gln Glu Cys Val Glu
    530                 535                 540

Glu Cys Arg Val Leu Gln Gly Leu Pro Arg Glu Tyr Val Asn Ala Arg
545                 550                 555                 560

His Cys Leu Pro Cys His Pro Glu Cys Gln Pro Gln Asn Gly Ser Val
```

```
                         565                 570                 575
            Thr Cys Phe Gly Pro Glu Ala Asp Gln Cys Val Ala Cys Ala His Tyr
                            580                 585                 590
            Lys Asp Pro Pro Phe Cys Val Ala Arg Cys Pro Ser Gly Val Lys Pro
                            595                 600                 605
            Asp Leu Ser Tyr Met Pro Ile Trp Lys Phe Pro Asp Glu Glu Gly Ala
                            610                 615                 620
            Cys Gln Pro Cys Pro Ile Asn Cys Thr His Ser Cys Val Asp Leu Asp
            625                 630                 635                 640
            Asp Lys Gly Cys Pro Ala Glu Gln Arg Ala Ser Pro Leu Thr Ser Ile
                            645                 650                 655
            Ile Ser Ala Val Val Gly Ile Leu Leu Val Val Leu Gly Val Val
                            660                 665                 670
            Phe Gly Ile Leu Ile Lys Arg Arg Gln Gln Lys Ile Arg Lys Tyr Thr
                            675                 680                 685
            Met Arg Arg Asn Glu Asp Leu Gly Pro Ser Ser Pro Met Asp Ser Thr
                            690                 695                 700
            Phe Tyr Arg Ser Leu Leu Glu Asp Glu Asp Met Gly Glu Leu Val Asp
            705                 710                 715                 720
            Ala Glu Glu Tyr Leu Val Pro Gln Gln Gly Phe Phe Cys Pro Asp Pro
                            725                 730                 735
            Thr Pro Gly Thr Gly Ser Thr Ala His Arg Arg His Arg Ser Ser Ser
                            740                 745                 750
            Ala Arg Asn Gly Gly Gly Asp Leu Thr Leu Gly Met Glu Pro Ser Gly
                            755                 760                 765
            Glu Gly Pro Pro Arg Ser Pro Arg Ala Pro Ser Glu Gly Thr Gly Ser
                            770                 775                 780
            Asp Val Phe Asp Gly Asp Leu Ala Val Gly Val Thr Lys Gly Leu Gln
            785                 790                 795                 800
            Ser Leu Ser Pro Gln Asp Leu Ser Pro Leu Gln Arg Tyr Ser Glu Asp
                            805                 810                 815
            Pro Thr Leu Pro Leu Pro Ser Glu Thr Asp Gly Lys Val Ala Pro Leu
                            820                 825                 830
            Ser Cys Ser Pro Gln Pro Glu Phe Val Asn Gln Ser Asp Val Gln Pro
                            835                 840                 845
            Lys Ser Pro Leu Thr Pro Glu Gly Pro Ser Pro Ala Arg Pro Thr
                            850                 855                 860
            Gly Ala Thr Leu Glu Arg Ala Lys Thr Leu Ser Pro Gly Lys Asn Gly
            865                 870                 875                 880
            Val Val Lys Asp Val Phe Thr Phe Gly Gly Ala Val Glu Asn Pro Glu
                            885                 890                 895
            Phe Leu Ala Pro Arg Glu Gly Thr Ala Ser Pro His Pro Ser Pro
                            900                 905                 910
            Ala Phe Ser Pro Ala Phe Asp Asn Leu Phe Phe Trp Asp Gln Asn Ser
                            915                 920                 925
            Ser Glu Gln Gly Pro Pro Pro Ser Asn Phe Glu Gly Thr Pro Thr Ala
                            930                 935                 940
            Glu Asn Pro Glu Phe Leu Gly Leu Asp Val Pro Val
            945                 950                 955

<210> SEQ ID NO 21
<211> LENGTH: 2871
<212> TYPE: DNA
<213> ORGANISM: Artificial Sequence
```

<220> FEATURE:
<223> OTHER INFORMATION: Synthetic Construct

<400> SEQUENCE: 21

```
atggctagcg agctggccgc cctgtgtaga tggggactgc tgctggctct gctgcctcct      60
ggagccgctt ctacacaggt ctgcaccggc accgacatga agctgagact gcccgccagc     120
cccgagacac acctggacat gctgcggcac ctgtaccagg ctgccaggt ggtccagggg      180
aatctggaac tgacctacct gcccaccaac gccagcctga gcttcctgca ggacatccag     240
gaagtgcagg gctacgtcct gatcgcccac aaccaggtcc gccaggtgcc cctgcagcgg     300
ctgagaatcg tgcggggcac ccagctgttc gaggacaact acgccctggc cgtgctggac     360
aacggcgacc ctctggatag cgtggcccct gctgctgggg ctacacctgg cggactgcag     420
gaactgcagc tgcggagcct gaccgagatc ctgaagggcg cgtgctgat caggcggagc      480
cctcagctgt gccaccagga caccgtgctg tgggaggacg tgttccggaa gaacaaccag     540
ctggccctcg tgctgatgga caccaacaga agccgggcct gccaccctg cgcccccatg      600
tgcaaggcca atcactgctg gggagagagc agccaggact gccagaccct gacccggacc     660
atctgcacca gcgcctgcgc cagatgcaag gccccctgc ctaccgactg ctgccacgaa      720
cagtgcgccg ctggctgcac cggccccaag cacagcgatt gcctggcctg cctgcacttc     780
aaccacagcg gcatctgcga gctgcactgc cctgccctgg tgacatacaa caccgacacc     840
ttcgagagca tgcccaaccc cgagggccgg tacaccttcg gcgccagctg tgtgaccgcc     900
tgcccctaca actacctgag caccgacgtg ggcagctgca ccctggtgtg ccccctgcac     960
aaccaggaag tgaccgccga ggacggcacc cagagatgcg agaagtgcag caagccttgc    1020
gccagagtgt gctacggcct gggcatggaa cacctgagag aggccagagc catcaccagc    1080
gccaacgtgc aggacttcgt gggctgcaag aagattttcg gctccctggc cttcctgccc    1140
gagagcttcg acggcgatcc tgcctctggc accgccctc tgcagcctga gcagctgcag    1200
gtcttcgaga cactggaaga gatcaccggc tacctgtaca tcagcgcctg gcccgacagc    1260
ttccccaacc tgagcgtgtt ccagaacctg agagtgatcc ggggcagaat cctgcacaac    1320
ggcgcctaca gcctgaccct gcagggcctg gaatcagct ggctgggcct gcggagcctg    1380
caggaactgg gatctggcct ggctctggtg caccggaacg cccggctgtg cttcgtgcac    1440
accgtgccct gggaccagct gttcagaaac ccccaccagg ctctgctgca cagcggcaac    1500
cggcccgaag aggattgcgt gggcgagggc ttcgtgtgct actccctgtg cgcccacggc    1560
cactgttggg gacctggccc tacccagtgc gtgaactgca gccacttcct gcggggccaa    1620
gaatgcgtgg aagagtgccg ggtgctgcag ggactgcccc gggaatacgt gaacgccaga    1680
cactgcctgc cttgccaccc cgagtgccag cccagaatg gcagcgtgac ctgcttcgga    1740
cccgaggccg atcagtgtgt ggcctgcgcc cactacaagg accccccatt ctgcgtggcc    1800
agatgcccca cgcgcgtgaa gcccgacctg agctacatgc ccatctggaa gttccccgac    1860
gaggaaggcg cctgccagcc ttgccccatc aactgcaccc acagctgcgt ggacctggac    1920
gacaagggct gccctgccga gcagagagcc agcccctga ccagcatcat cagcgccgtg    1980
gtgggaatcc tgctggtggt ggtgctgggc gtggtgttcg gcatcctgat caagcggcgg    2040
cagcagaaga tccggaagta caccatgcgg cggaacgagg acctgggccc ctctagcccc    2100
atggacagca ccttctaccg gtccctgctg gaagatgagg acatgggcga gctggtggac    2160
gccgaggaat acctggtgcc tcagcagggc ttcttctgcc ccgaccctac ccctggcacc    2220
```

-continued

```
ggctctaccg cccacagacg gcacagaagc agcagcgcca gaaacggcgg aggcgacctg    2280
accctgggaa tggaacctag cggcgaggga cctcccagaa gccctagagc ccctagcgag    2340
ggcaccggca gcgacgtgtt cgatggcgat ctggccgtgg gcgtgaccaa gggactgcag    2400
agcctgagcc cccaggacct gtcccccctg cagagataca gcgaggaccc caccctgccc    2460
ctgcccagcg agacagatgg caaggtggcc cccctgagct gcagccctca gcccgagttc    2520
gtgaaccaga gcgacgtgca gcccaagtcc cccctgacac ccgagggacc tccaagccct    2580
gccagaccta ccggcgccac cctggaaaga gccaagaccc tgagcccgg caagaacggc     2640 gtggtgaaag acgtgttcac cttcggaggc gccgtggaaa accccgagtt cctggccccc    2700
agagagggca cagccagccc tccacacccc agcccagcct tctcccccgc cttcgacaac    2760
ctgttcttct gggaccagaa cagcagcgag cagggcccac cccccagcaa tttcgagggc    2820 accccaccg ccgagaatcc tgagttcctg ggcctggacg tgcccgtgtg a              2871
```

<210> SEQ ID NO 22
<211> LENGTH: 265
<212> TYPE: PRT
<213> ORGANISM: Artificial Sequence
<220> FEATURE:
<223> OTHER INFORMATION: Synthetic Construct

<400> SEQUENCE: 22

```
Asn Glu Asp Leu Gly Pro Ser Pro Met Asp Ser Thr Phe Tyr Arg
1               5                   10                  15

Ser Leu Leu Glu Asp Glu Asp Met Gly Glu Leu Val Asp Ala Glu
            20                  25                  30

Tyr Leu Val Pro Gln Gln Gly Phe Phe Cys Pro Asp Pro Thr Pro Gly
        35                  40                  45

Thr Gly Ser Thr Ala His Arg Arg His Arg Ser Ser Ala Arg Asn
    50                  55                  60

Gly Gly Gly Asp Leu Thr Leu Gly Met Glu Pro Ser Gly Glu Gly Pro
65                  70                  75                  80

Pro Arg Ser Pro Arg Ala Pro Ser Glu Gly Thr Gly Ser Asp Val Phe
                85                  90                  95

Asp Gly Asp Leu Ala Val Gly Val Thr Lys Gly Leu Gln Ser Leu Ser
                100                 105                 110

Pro Gln Asp Leu Ser Pro Leu Gln Arg Tyr Ser Glu Asp Pro Thr Leu
            115                 120                 125

Pro Leu Pro Ser Glu Thr Asp Gly Lys Val Ala Pro Leu Ser Cys Ser
        130                 135                 140

Pro Gln Pro Glu Phe Val Asn Gln Ser Asp Val Gln Pro Lys Ser Pro
145                 150                 155                 160

Leu Thr Pro Glu Gly Pro Pro Ser Pro Ala Arg Pro Thr Gly Ala Thr
                165                 170                 175

Leu Glu Arg Ala Lys Thr Leu Ser Pro Gly Lys Asn Gly Val Val Lys
            180                 185                 190

Asp Val Phe Thr Phe Gly Gly Ala Val Glu Asn Pro Glu Phe Leu Ala
        195                 200                 205

Pro Arg Glu Gly Thr Ala Ser Pro His Pro Ser Pro Ala Phe Ser
    210                 215                 220

Pro Ala Phe Asp Asn Leu Phe Phe Trp Asp Gln Asn Ser Ser Glu Gln
225                 230                 235                 240

Gly Pro Pro Pro Ser Asn Phe Glu Gly Thr Thr Ala Glu Asn Pro
                245                 250                 255
```

Glu Phe Leu Gly Leu Asp Val Pro Val
            260                 265

<210> SEQ ID NO 23
<211> LENGTH: 798
<212> TYPE: DNA
<213> ORGANISM: Artificial Sequence
<220> FEATURE:
<223> OTHER INFORMATION: Synthetic Construct

<400> SEQUENCE: 23

```
aacgaggacc tgggcccctc tagccccatg gacagcacct tctaccggtc cctgctggaa      60
gatgaggaca tgggcgagct ggtggacgcc gaggaatacc tggtgcctca gcagggcttc     120
ttctgccccg accctacccc tggcaccggc tctaccgccc acagacggca cagaagcagc     180
agcgccagaa acggcggagg cgacctgacc ctgggaatgg aacctagcgg cgagggacct     240
cccagaagcc ctagagcccc tagcgagggc accggcagcg acgtgttcga tggcgatctg     300
gccgtgggcg tgaccaaggg actgcagagc ctgagccccc aggacctgtc cccctgcag     360
agatacagcg aggaccccac cctgccctg cccagcgaga cagatggcaa ggtggccccc     420
ctgagctgca gccctcagcc cgagttcgtg aaccagagcg acgtgcagcc caagtccccc     480
ctgacacccg agggacctcc aagccctgcc agacctaccg gcgccaccct ggaaagagcc     540
aagaccctga gccccggcaa gaacggcgtg gtgaaagacg tgttcacctt cggaggcgcc     600
gtggaaaacc ccgagttcct ggcccccaga gagggcacag ccagccctcc acaccccagc     660
ccagccttct ccccgccctt cgacaacctg ttcttctggg accagaacag cagcgagcag     720
ggcccacccc ccagcaattt cgagggcacc cccaccgccg agaatcctga gttcctgggc     780
ctggacgtgc ccgtgtga                                                   798
```

<210> SEQ ID NO 24
<211> LENGTH: 90
<212> TYPE: DNA
<213> ORGANISM: Artificial Sequence
<220> FEATURE:
<223> OTHER INFORMATION: Synthetic Construct

<400> SEQUENCE: 24

```
cagagagcca gccccctgac cagcatcatc agcgccgtgg tgggaatcct gctggtggtg      60
gtgctgggcg tggtgttcgg catcctgatc                                      90
```

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Ser Tyr Val Asn Thr Asn Met Gly Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Thr Tyr Val Pro Ala Asn Ala Ser Leu
1               5

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct

<400> SEQUENCE: 27

Asp Met Val Leu Trp Lys Asp Val Phe Arg Lys Asn Asn Gln Leu
1               5                   10                  15

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Thr Tyr Leu Pro Ala Asn Ala Ser Leu
1               5

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Phe Leu Pro Ser Asp Phe Phe Pro Ser Val
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

Ala Leu Cys Arg Trp Gly Leu Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

His Leu Tyr Gln Gly Cys Gln Val Val
1               5

<210> SEQ ID NO 32
<211> LENGTH: 17
<212> TYPE: PRT
<213> ORGANISM: Artificial Sequence
<220> FEATURE:
<223> OTHER INFORMATION: Synthetic Construct

<400> SEQUENCE: 32

Arg Leu Arg Ile Val Arg Gly Thr Gln Leu Phe Glu Asp Asn Tyr Ala

```
1               5               10              15

Leu

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Gln Leu Phe Glu Asp Asn Tyr Ala Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Construct

<400> SEQUENCE: 34

Lys Ile Phe Gly Ser Leu Ala Phe Leu
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

Ile Leu His Asn Gly Ala Tyr Ser Leu
1               5

<210> SEQ ID NO 36
<211> LENGTH: 12
<212> TYPE: PRT
<213> ORGANISM: Artificial Sequence
<220> FEATURE:
<223> OTHER INFORMATION: Synthetic Construct

<400> SEQUENCE: 36

Ala Leu Cys Arg Trp Gly Leu Leu Leu Ala Leu Leu
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct

<400> SEQUENCE: 37

His Leu Tyr Gln Gly Cys Gln Val Val
1               5

<210> SEQ ID NO 38
<211> LENGTH: 17
<212> TYPE: PRT
<213> ORGANISM: Artificial Sequence
<220> FEATURE:
<223> OTHER INFORMATION: Synthetic Construct

<400> SEQUENCE: 38
```

```
Arg Leu Arg Ile Val Arg Gly Thr Gln Leu Phe Glu Asp Asn Tyr Ala
1               5                   10                  15
Leu

<210> SEQ ID NO 39
<211> LENGTH: 18
<212> TYPE: PRT
<213> ORGANISM: Artificial Sequence
<220> FEATURE:
<223> OTHER INFORMATION: Synthetic Construct

<400> SEQUENCE: 39

Thr Gln Arg Cys Glu Lys Cys Ser Lys Pro Cys Ala Arg Val Cys Tyr
1               5                   10                  15
Gly Leu

<210> SEQ ID NO 40
<211> LENGTH: 18
<212> TYPE: PRT
<213> ORGANISM: Artificial Sequence
<220> FEATURE:
<223> OTHER INFORMATION: Synthetic Construct

<400> SEQUENCE: 40

Lys Ile Phe Gly Ser Leu Ala Phe Leu Pro Glu Ser Phe Asp Gly Asp
1               5                   10                  15
Pro Ala

<210> SEQ ID NO 41
<211> LENGTH: 9
<212> TYPE: PRT
<213> ORGANISM: Artificial Sequence
<220> FEATURE:
<223> OTHER INFORMATION: Synthetic Construct

<400> SEQUENCE: 41

Tyr Leu Val Pro Gln Gln Gly Phe Phe
1               5
```

HER-2 PEPTIDES AND VACCINES

CROSS-REFERENCE TO RELATED APPLICATIONS

This application is a national stage of PCT International Application No. PCT/IB2011/052246, filed on May 23, 2011, which claims priority to U.S. provisional Application No. 61/352,318 filed on Jun. 7, 2010, which incorporated herein by reference in its entirety.

REFERENCE TO SEQUENCE LISTING

This application is being filed electronically via EFS-Web and includes an electronically submitted sequence listing in .txt format. The .txt file contains a sequence listing entitled "PC33933ASequenceListingST25.txt" created on Oct. 9, 2013, and having a size of 97.8 KB. The sequence listing contained in this .txt file is part of the specification and is incorporated herein by reference in its entirety.

FIELD OF THE INVENTION

The present invention relates to vaccines useful for treating or preventing cancer, and specifically to vaccines against cancer disease that is associated with HER-2.

BACKGROUND OF THE INVENTION

Tumor antigens are a group of proteins expressed by tumor cells. These antigens are divided into five categories according to their expression profile: (1) antigens specific for the patient, resulting from point mutations related to tumorigenesis, (2) tumor-specific antigens (TSA) expressed in many tumors and a few normal tissues devoid of conventional HLA molecules, (3) differentiation antigens which are expressed either during embryogenesis or in quite specific cell types, (4) antigens over expressed by tumors (such as survivin, gp75, PSA, HER-2, p53, and telomerase) and (5) viral antigens.

Human epidermal growth factor receptor-2 (also known as HER-2, HER-2/neu, c-erbB-2 or p185; hereinafter referred to as HER-2, HER-2 receptor, or HER-2 protein) is a 185 kDa protein that belongs to the epidermal growth factor receptor family. Sequences of human HER-2 and its orthologs are available from the NCBI web site: http://www.ncbi.nlm.nih.gov/, where the sequences are identified with the following RefSeq Identifiers: NP_004439.2 (human), XP_001090319.1 (rhesus), XP_001501155.1 (horse), NP_001003217.1 (dog), NP_001041628.1 (cat), NP_058699.2 (rat), and NP_001003817.1 (mouse). The amino acid sequence of the full length human HER-2 protein is provided in SEQ ID NO: 1. The DNA sequence encoding the amino acid sequence of the full length human HER-2 protein is provided in SEQ ID NO: 2. Human HER-2 protein consists of an extracellular domain (ECD) (amino acids 1-653), a transmembrane domain (TMD)(amino acids 654-675), and an intracellular domain (ICD)(amino acids 676-1255). The ECD includes a signal sequence that consists of amino acids 1-22. The ICD includes a tyrosine kinase domain (amino acids 720-787) and a carboxy terminal (C-terminal) domain (CTD)(amino acids 991-1255).

HER-2 protein has been found to be amplified and over expressed in several types of human adenocarcinomas, especially in tumors of the breast and the ovary. For example, HER-2 was found to be over expressed (3+) in 15-25% and moderately (1+) to highly (2+) expressed in 30-45% of the breast cancer patients. (See Perez E A, et al, HER2 testing in patients with Breast Cancer: Poor correlation between weak positivity by immunohistochemistry and gene amplification by fluorescence in situ hybridization. Mayo Clin. Proc. 2002; 77:148-154.) Therefore, for the purposes of this invention, such cancers are considered to be "cancers associated with HER-2."

Several vaccine strategies targeting tumors that over express HER-2 using peptides, proteins, plasmid DNA, and viral vector approaches have been explored. For example, U.S. Pat. No. 7,348,018 mentions a peptide of the HER-2 ECD domain and its use for eliciting or enhancing an immune response. Published US patent application US2006/074038 refers to a HER-2 expressing plasmid construct encoding a truncated HER-2 gene that lacked the intracellular domain and the use of such a construct as a vaccine. Many of these strategies have seen little or no clinical responses mainly due to use of a single antigen and/or self antigens to induce immune responses that do not break immune tolerance or adequately activate dendritic cells (DCs) and expand cytotoxic T lymphocytes (CTLs).

SUMMARY OF THE INVENTION

In one aspect, the present disclosure provides an isolated immunogenic HER-2 peptide capable of eliciting an immune response against the human HER-2 receptor, which comprises an amino acid sequence derived from the ECD of the human HER-2 protein ("ECD-derived peptide"). In some embodiments, the ECD-derived peptide contains the amino acid sequences of at least four of the conserved T cell epitopes in the ECD domain of human HER-2 receptor and shares from 70% to 95% identity with the ECD domain of human HER-2 receptor. In another aspect, the present disclosure provides an isolated immunogenic HER-2 peptide capable of eliciting an immune response against human HER-2 receptor, which comprises an ECD-derived peptide linked to a CTD-derived peptide, wherein the ECD-derived peptide contains the amino acid sequences of at least four of the conserved T cell epitopes in the ECD domain of human HER-2 receptor and shares from 70% to 95% identity with the ECD domain of human HER-2 receptor, and wherein the CTD-derived peptide contains the amino acid sequence of the conserved T cell epitope in the CTD domain of human HER-2 protein and shares from 70% to 95% identity with the amino acid sequence of the CTD domain of the human HER-2 protein.

In another aspect, the present disclosure provides an isolated immunogenic HER-2 peptide capable of eliciting an immune response against human HER-2 receptor, which comprises an ECD-derived peptide, a CTD-derived peptide, and a TMD-derived peptide, wherein the carboxy terminus of the ECD-derived peptide is joined to the amino terminus of the TMD-derived peptide and the carboxy terminus of the TMD-derived peptide is joined to the amino terminus of the CTD-derived peptide. Preferably, the ECD-derived peptide, TMD-derived peptide, and CTD-derived peptide are each joined together by a peptide bond to form a fusion protein.

In another aspect, the present disclosure provides an isolated nucleic acid molecule comprising a nucleotide sequence that encodes an isolated immunogenic HER-2 peptide provided by the present disclosure.

In another aspect, the present disclosure provides a composition, which comprises an isolated immunogenic HER-2 peptide or an isolated nucleic acid molecule, provided by the present disclosure, and a pharmaceutically acceptable excipient. In some embodiments, composition is a vaccine composition.

In yet another aspect, the present disclosure provides a method of inhibiting abnormal cell proliferation, eliciting an immune response against HER-2 protein, or treating or preventing cancer in a mammal, comprising administering to the mammal an effective amount of a vaccine composition provided by the present disclosure.

DETAILED DESCRIPTION OF THE INVENTION

A. Definitions of Terms

Figure 1:
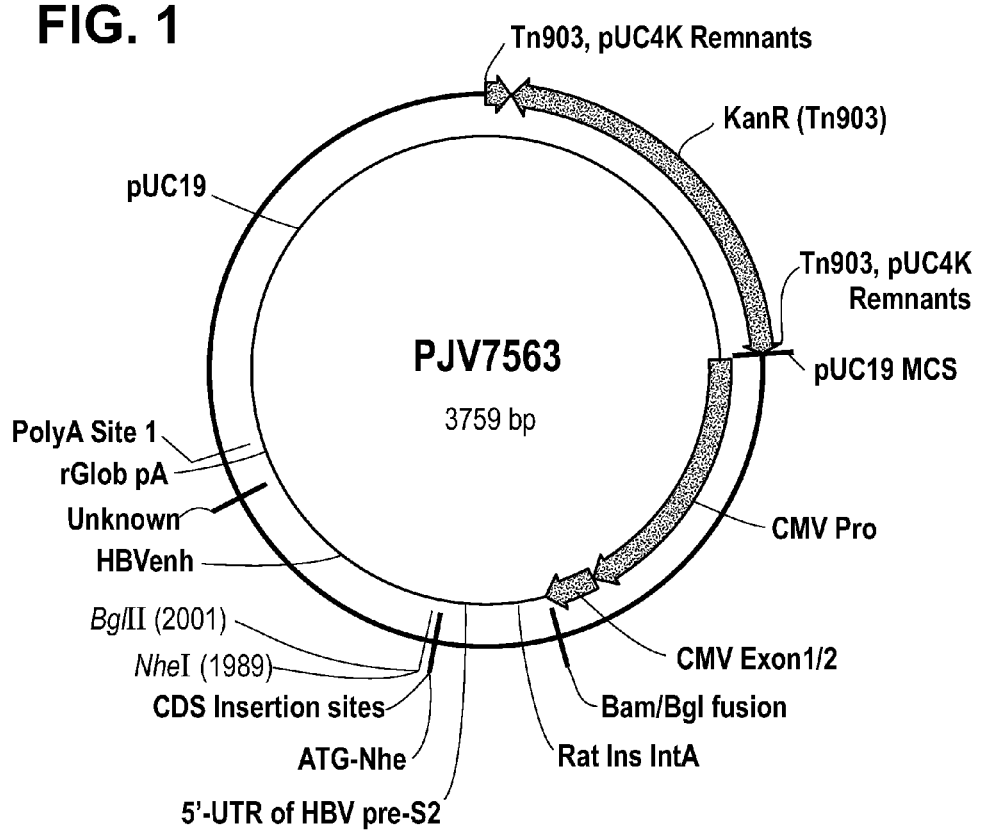
FIG. 1 represents a vector map of a plasmid for cloning RaDHER2. RaDHER2 and control genes (human and rat HER2) were cloned into PJV7563 at NheI (5') and BglII (3') sites.

The term "adjuvant" refers to a substance that is capable of enhancing, accelerating, or prolonging an immune response when given with a vaccine antigen.

The term "antigen" refers to a substance that is capable of inducing a specific humoral and/or cell-mediated immune response. An antigen generally contains at least one epitope. Examples of antigens include molecules which contain a peptide, polysaccharide, nucleic acid sequence, and/or lipid.

The term "immunogenic HER2 peptide" refers to a peptide that, when administered with an appropriate carrier and/or adjuvant, is capable of eliciting an immune response against human HER-2 protein or against cells expressing human HER-2 protein.

The term "conserved T cell epitope" refers to one of the following amino acid sequences of the human HER-2 protein as set forth in SEQ ID NO. 1: amino acids 5-16 (ALCRWGLLLALL) (SEQ ID NO: 36) (HLA-A2/HLA-A24), amino acids 48-56 (HLYQGCQVV) (SEQ ID NO: 37) (HLA-A2), amino acids 98-114 (RLRIVRGTQLFEDNYAL) (SEQ ID NO: 38) (HLA-DR/HLA-A2), amino acids 328-345 (TQRCEKCSKPCARVCYGL) (SEQ ID NO: 39) (HLA-DR), amino acids 369-386 (KIFGSLAFLPESFDGDPA) (SEQ ID NO: 40) (HLA-A2, -A3, -A26/HLA-DR), and amino acids 1023-1031 (YLVPQQGFF) (SEQ ID NO: 41) (HLA-A2).

The term "CTD-derived peptide" refers to a peptide that comprises the amino acid sequence of the conserved T cell epitope (i.e., amino acids 1023-1031 of SEQ ID No.: 1) on the CTD of the human HER-2 protein and is at least 70% identical to the amino acid sequence of the CTD of the human HER-2 protein.

The term "ECD-derived peptide" refers to a peptide that comprises the amino acid sequences of at least four of the conserved T cell epitopes of the ECD of the human HER-2 and shares from 70% to 95% identity with the amino acid sequence of the ECD of the human HER-2 protein.

The term "effective amount" refers to an amount delivered to the subject that is sufficient to cause a desired effect in the subject.

The term "eliciting an immune response" means stimulating, initiating, or inducing an immune response, and/or improving, amplifying, enhancing, increasing or prolonging a pre-existing immune response.

The term "functional variant" of an immunogenic HER-2 peptide refers to a peptide that is at least 70% identical to the amino acid sequence of that immunogenic HER-2 peptide and is capable of inducing substantially the same immune response as that immunogenic HER-2 peptide.

The term "immune response" refers to any response to an antigen by the immune system of a vertebrate animal in vivo, or by one or more components of the immune system of a vertebrate animal in vitro. Exemplary immune responses include, but are not limited to, local and systemic cellular as well as humoral immunity, such as cytotoxic T lymphocytes (CTL) responses, including antigen-specific induction of $CD8^+$ CTLs, helper T-cell responses including T-cell proliferative responses and cytokine release, and B-cell responses including antibody response.

The term "pharmaceutically acceptable excipient" refers to a substance, other than the active ingredient or adjuvant, that is compatible with the active ingredient and does not cause significant untoward effect in subjects to whom it is administered.

The term "polypeptide," "peptide," and "protein," are used interchangeably herein, and refer to a polymeric form of amino acids of any length, which can include coded and non-coded amino acids, chemically or biochemically modified or derivatized amino acids, and polypeptides having modified peptide backbones.

The term "ortholog" refers to genes in different species that are similar to each other and originated from a common ancestor.

The term "preventing" or "prevent" refers to a) keeping a disorder from occurring or b) delaying the onset of a disorder or onset of a symptoms of a disorder.

The term "TMD-derived peptide" refers to a peptide that is at least 50% identical to the amino acid sequence of the transmembrane domain (TMD) of human HER-2 protein. A TMD-derived peptide may have amino acid sequence only from the CTD of human HER-2; it may also contain amino acid sequence from the cytoplasmic terminal domain (CTD) of human HER-2.

The term "treating," "treatment," or "treat" refers to abrogating a disorder, reducing the severity of a disorder, or reducing the severity or occurrence frequency of a symptom of a disorder.

B. Immunogenic HER-2 Peptides

In some aspects, the present disclosure provides isolated immunogenic HER-2 peptides capable of eliciting an immune response against human HER-2 protein or against cells expressing human HER-2 protein. The peptides comprise the amino acid sequences of at least four of the conserved T cell epitopes of human HER-2 protein and share from 70% to 95% identity with the amino acid sequence of human HER-2 protein. In some embodiments, the peptides comprise the amino acid sequences of at least five of the conserved T cell epitopes of human HER-2 and share from 70% to 95% identity, from 75% to 85% identity, or from 85% to 95% identity, with the amino acid sequence of human HER-2 protein.

An immunogenic HER2 peptide of the invention may be derived by conserving some or all of the conserved T cell epitopes of the human HER-2 protein while substituting certain amino acids in the remaining regions of the human HER-2 protein with amino acids found in one or more orthologs of human HER-2 protein at corresponding positions. Examples of orthologs of human HER-2 include the HER-2 protein of rhesus monkey (XP_001090319.1), horse (XP_001501155.1), dog (NP_001003217.1), cat (NP_001041628.1), rat (NP_058699.2), mouse (NP_001003817.1), chimp (XR_025186.1), cow (XR_083057.1), and hamster (D16295.1). Substitutions of amino acids of human HER2 protein with amino acids from one or more of the orthologs may be conservative substitutions or non-conservative substitutions, or both, and may be selected based on a number of factors known in the art, including the divergence needed to be achieved, MHC binding, the presence of ortholog amino acids at the site of substitution, surface exposure, and maintaining the 3-D structure of the protein for optimal processing and presentation.

The capability of an isolated immunogenic HER-2 peptide to elicit an immune response can be measured in in vitro assays or in vivo assays. In one particular embodiment, the immune response is a T cell response measured in an in vitro assay. In vitro assays or tests for determining the capability of a peptide or DNA construct to elicit immune responses are known in the art. One example of such in vitro assays that may be used to determine the capability of an isolated polypeptide of the invention to elicit immune response is to measure the capability of the antigen to stimulate T cell response as described in U.S. Pat. No. 7,387,882, the disclosure of which is incorporated in this application. The assay method comprises the steps of: (1) contacting antigen presenting cells in culture with an antigen thereby the antigen can be taken up and processed by the antigen presenting cells, producing one or more processed antigens; (2) contacting the antigen presenting cells with T cells under conditions sufficient for the T cells to respond to one or more of the processed antigens; (3) determining whether the T cells respond to one or more of the processed antigens. The T cells used may be $CD8^+$ T cells or $CD4^+$ T cells. T cell response may be determined by measuring the release of one of more of cytokines, such as interferon-gamma and interleukin-2, lysis of the antigen presenting cells (tumor cells), and production of antibodies by B cells. One specific exemplary assay is described in Example 3 provided in the present application.

In one aspect, the immunogenic HER-2 peptide provided by this disclosure comprises an ECD-derived peptide. In some embodiments, the amino acid sequence of the ECD-derived peptide comprises the amino acid sequences of at least four, preferably at least five, of the conserved T cell epitopes of the ECD of the human HER-2 protein and shares from 70% to 85% identity with the amino acid sequence of the ECD of human HER-2 protein. In other embodiments, the amino acid sequence of the ECD-derived peptide comprises the amino acid sequences of at least four, preferably at least five of the conserved T cell epitopes of the ECD of the human HER-2 protein and shares from 85% to 95% identity with the amino acid sequence of the ECD of human HER-2 protein.

In some particular embodiments, the ECD-derived peptide comprises the amino acid sequences of the five conserved T cell epitopes of the ECD of the human HER-2 and includes, in positions outside of the conserved T cell epitopes in the ECD domain of the human HER-2, from 50 to 130 amino acids that are found in one or more of the human HER-2 orthologs in corresponding positions and are different from the amino acids found in the ECD domain of human HER-2.

In some further embodiments, the ECD-derived peptide comprises the amino acid sequences of five conserved T cell epitopes of the ECD of the human HER-2 and includes, in positions outside of the conserved T cell epitopes in the ECD of the human HER-2, from 120 to 130 amino acids that are found in one or more of the human HER-2 orthologs in corresponding positions and are different from the amino acids found in the ECD of human HER-2.

In still some further embodiments, the ECD-derived peptide comprises the amino acid sequences of five conserved T cell epitopes of the ECD of the human HER-2 and includes, in positions outside of the conserved T cell epitopes in the ECD of the human HER-2, from 50 to 70 amino acid that are found in one or more of the human HER-2 orthologs in corresponding positions and are different from the amino acids found in the ECD of human HER-2.

In a particular embodiment, the amino acid sequence of the ECD-derived peptide comprises amino acids 23-645 of SEQ ID NO.: 5 or amino acids 25-647 of SEQ ID NO: 14.

In still another particular embodiment, the amino acid sequence of the ECD-derived peptide is at least 80%, at least 85%, at least 90%, at least 95%, or at least 99% identical to amino acids 23-645 of SEQ ID NO. 5, or is at least 80%, at least 85%, at least 90%, at least 95%, or at least 99% identical to amino acids 25-647 of SEQ ID NO: 14.

In still another particular embodiment, the present invention provides an isolated peptide that comprises an amino acid sequence encoded by the nucleic acid sequence of SEQ ID NO: 6 or encoded by the nucleic acid sequence of SEQ ID NO:15.

In another aspect, the present invention provides an isolated immunogenic HER-2 peptide that comprises an ECD-derived peptide and a CTD-derived peptide, wherein the C-terminal end of the ECD-derived peptide is joined to the N-terminal end of the CTD-derived peptide. In some embodiments, the ECD-derived peptide is joined to the N-terminal end of the CTD-derived peptide by a peptide bond to form a fusion peptide. The ECD-derived peptide is as described herein. In some embodiments, the amino acid sequence of the ECD-derived peptide comprises amino acids 23-645 SEQ ID NO: 5 or amino acids 25-647 of SEQ ID NO: 14

A CTD-derived peptide may be obtained by conserving the conserved T cell epitope (i.e., amino acids 1023-1031 of SEQ ID No.: 1) in the CTD of the human HER-2 protein while substituting certain amino acids in the remaining regions of the CTD of the human HER-2 protein with amino acids found in one or more orthologs of human HER-2 protein in corresponding positions. In one embodiment, the CTD-derived peptide shares from 70% to 95% identity with the amino acid sequence of CTD of the human HER-2. In another embodiment, the CTD-derived peptide contains from 15 to 70 amino acids that are found in corresponding positions in the CTD domain of one or more orthologs of the human HER-2 and are different from the amino acids in the CTD of human HER-2 protein. In a particular embodiment, the CTD-derived peptide has an amino acid sequence of SEQ ID NO: 7. In another particular embodiment, the CTD-derived peptide has an amino acid sequence of SEQ ID NO: 22.

In other particular embodiments, the CTD-derived peptide is at least 80%, at least 85%, at least 90%, at least 95%, or at least 99% identical to the amino acid sequence of SEQ ID NO. 7, or is at least 80%, at least 85%, at least 90%, at least 95%, or at least 99% identical to the amino acid sequence of SEQ ID NO: 22.

In a particular embodiment, the isolated immunogenic HER-2 peptide has an amino acid sequence that is at least 80%, at least 85%, at least 90%, at least 95%, or at least 99% identical to amino acids 23-910 of SEQ ID NO: 3, or is at least 80%, at least 85%, at least 90%, at least 95%, or at least 99% identical to amino acids 25-912 of SEQ ID NO: 18.

In a specific embodiment, the isolated immunogenic HER-2 peptide comprises amino acids 23-910 of SEQ ID NO: 3. In another specific embodiment, the isolated immunogenic HER-2 peptide comprises amino acids 25-912 of SEQ ID NO: 18. In another specific embodiment, the isolated immunogenic HER-2 peptide consists of amino acids 23-910 of SEQ ID NO.: 3, or amino acids 25-912 of SEQ ID NO: 18.

In still another particular embodiment, the isolated immunogenic HER-2 peptide has an amino acid sequence that is encoded by a nucleic acid sequence of SEQ ID NO: 4 or 19.

In another aspect, the invention provides an isolated immunogenic HER-2 peptide comprising an ECD-derived peptide, a CTD-derived peptide, and a TMD-derived peptide, wherein the carboxy terminus of the ECD-derived peptide is joined to the amino terminus of the TMD-derived peptide and the carboxy terminus of the TMD-derived peptide is joined to the amino terminus of the CTD-derived peptide. Preferably, the ECD-derived peptide, TMD-derived peptide, and CTD-derived peptide are each joined together by a peptide bond to form a fusion protein, In some embodiments, the TMD-derived peptide has an amino acid sequence of SEQ ID NO: 11 or SEQ ID NO: 16.

In one specific embodiment, the present disclosure provides an isolated immunogenic HER-2 peptide comprising amino acids 23-940 of SEQ ID NO: 9; In another specific embodiment, the present disclosure provides an isolated immunogenic HER-2 peptide comprising amino acids 25-956 of SEQ ID NO: 20.

The present disclosure also provides functional variants of the immunogenic HER-2 peptides described herein. In some embodiments, the functional variants are at least 80%, at least 85%, at least 90%, at least 95%, or at least 99% identical to the amino acid sequence of any of the specific immunogenic HER-2 peptides provided herein. Functional variants can be obtained by deleting, inserting, or substituting one or more amino acids in a given immunogenic HER-2 peptide. An example for the production of such variants is the conservative substitution of individual amino acids of the polypeptides, that is, by substituting one amino acid by another having similar properties.

In some particular embodiments, the present disclosure provides a functional variant that is at least 80%, at least 85%, at least 90%, at least 95%, or at least 99% identical to the amino acid sequence of a peptide selected from the group consisting of:

1) a peptide comprising amino acids 23-910 of SEQ ID NO: 3;
2) a peptide comprising amino acids 23-645 of SEQ ID NO: 5;
3) a peptide comprising amino acids 23-940 of SEQ ID NO: 9;
4) a peptide comprising amino acids 25-647 of SEQ ID NO: 14;
4) a peptide comprising amino acids 25-912 of SEQ ID NO: 18; and
6) a peptide comprising amino acids 25-956 of SEQ ID NO: 20.

The isolated immunogenic HER-2 peptides provided by the present invention can be prepared by any suitable method known in the art, such as recombinant technologies.

C. Nucleic Acid Molecules

In other aspects, the present invention provides an isolated nucleic acid molecule that comprises a nucleotide sequence encoding an immunogenic HER-2 peptide, or a functional variant thereof, provided by the present disclosure.

In some embodiments, the nucleotide sequence encodes an ECD-derived peptide provided by the present disclosure. In one embodiment, ECD-derived peptide comprises the amino acid sequences of at least five conserved T cell epitopes of the ECD domain of the human HER-2 protein and shares from 70% to 95% identity, from 75% to 85% identity, or from 85% to 95% identity, with the ECD of the human HER-2 protein.

In another embodiment, the nucleotide sequence encodes an ECD-derived peptide that includes, in positions outside of the epitopes in the ECD of the human HER-2 protein, from 120 to 130 amino acids that are found in one or more of the human HER-2 orthologs and are different from the amino acids found in the ECD of human HER-2 protein.

In still another embodiment, the nucleotide sequence encodes an ECD-derived peptide that includes, in positions outside of the epitopes in the ECD of the human HER-2 protein, from 50 to 130 amino acids that are found in one or more of the human HER-2 orthologs and are different from the amino acids found in the ECD of human HER-2 protein.

In yet another embodiment, the nucleotide sequence encodes an ECD-derived peptide that is joined to a CTD-derived peptide, wherein the CTD-derived peptide comprises the amino acid sequence of the T cell epitope in the CTD domain of the human HER-2 protein and further comprises from 15 to 70 amino acids that are found in one or more of the human HER-2 orthologs and are different from the amino acids found in the CTD of the human HER-2 protein.

In a specific embodiment, the nucleotide sequence encodes an amino acid sequence selected from the group consisting of:
a) amino acids 23-910 of SEQ ID NO: 3;
b) amino acids 23-645 of SEQ ID NO: 5,
c) amino acids 23-940 of SEQ ID NO: 9;
d) amino acids 1-623 of SEQ ID NO: 12;
e) amino acids 25-647 of SEQ ID NO: 14;
f) amino acids 25-912 of SEQ ID NO: 18; and
g) amino acids 25-956 of SEQ ID NO: 20.

In another specific embodiment, the nucleotide sequence encodes an amino acid sequence that is at least 80%, at least 85%, at least 90%, at least 95%, or at least 99% identical to the amino acid sequence selected from the group consisting of:
(a) amino acids 23-910 of SEQ ID NO: 3;
(b) amino acids 23-645 of SEQ ID NO: 5,
(c) amino acids 23-940 of SEQ ID NO: 9;
(d) amino acids 1-623 of SEQ ID NO: 12;
(e) amino acids 25-647 of SEQ ID NO: 14;
(f) amino acids 25-912 of SEQ ID NO: 18; and
(g) amino acids 25-956 of SEQ ID NO: 20.

In some further embodiments, the isolated nucleic acid molecule described herein above further comprises a nucleotide sequence that encodes the amino acids of the signal sequence of human HER-2 protein. The amino acid sequence of the signal sequence corresponds to amino acids 1-22 of SEQ ID NOs: 1, 3, 5, or 9. Codons encoding additional amino acids may be inserted into the nucleotide sequence in order to facilitate the expression of the protein. For example, codons encoding alanine and serine may be inserted into the nucleotide sequence at the positions between amino acid positions 1 and 2 of the signal sequence. One example of such a modified signal sequence is an amino acid sequence that corresponds to amino acids 1-24 of SEQ ID NO: 14, 18, and 20.

In another specific embodiment, the present invention provides a nucleic acid molecule that comprises the nucleotide sequence of SEQ IDS NO.: 4, 6, 10, 13, 15, 19, or 21. According to another aspect of the invention, there is provided a plasmid construct capable of expressing an immunogenic HER-2 peptide, which comprises a nucleic acid molecule provided by the invention inserted into an expression vector. Useful vectors include, but not limited to, biodegradable microcapsules, immunostimulating complexes (ISCOMs) or liposomes, and genetically engineered attenuated live vectors such as viruses or bacteria. Examples of suitable attenuated live bacterial vectors include *Salmonella typhimurium, Salmonella typhi, Shigella, Bacillus, Lactobacillus*, Bacille Calmette-Guerin (BCG), *Escherichia coli, Vibrio cholerae, Campylobacter, Listeria monocytogenes*, or any other suitable bacterial vector, as is known in the art. Methods of transforming live bacterial vectors with an exogenous DNA construct are well described in the art. See, for example, Joseph Sambrook and David W. Russell, Molecular Cloning, A Laboratory Manual, 3rd Ed., Cold Spring Harbor Laboratory Press, Cold Spring Harbor, N.Y. (2001). Examples of suitable viral vectors include bacteriophages, herpes virus, adenovirus, polio virus, vaccinia virus, and avipox. Methods of transforming viral vector with an exogenous DNA construct are also well described in the art. Individual expression vectors capable of expressing the genetic material can be produced using standard recombinant techniques. General cloning methods are described in, e.g., Maniatis et al., 1985 Molecular Cloning: A Laboratory Manual or DNA Cloning, Vol. I and II (D. N. Glover, ed., 1985).

D. Compositions Comprising an Immunogenic HER-2 Peptide (Peptide Compositions)

In another aspect of the present disclosure, there is provided a composition which comprises an isolated immunogenic HER-2 peptide provided by the present disclosure. The peptide compositions are useful for eliciting an immune response against HER-2 protein in a mammal, such as a human. In some embodiments, the composition is a peptide vaccine composition useful for immunization of a mammal for inhibiting abnormal cell proliferation, for providing protection against the development of cancer (used as a prophylactic), or for treatment of disorders (used as a therapeutic) associated with the HER-2 over expression, such as cancer.

In one embodiment, the peptide composition comprises an isolated immunogenic HER-2 peptide selected from the group consisting of:

(a) an ECD-derived peptide that comprises the amino acid sequence of at least four, at least five, or at least six conserved T cell epitopes of the ECD domain of the human HER-2 and shares from 70% to 95% identity, from 75% to 85% identity, or from 85% to 95% identity, with the ECD of human HER-2 protein;

(b) an ECD-derived peptide that includes, in positions outside of the conserved T cell epitopes in the ECD of the human HER-2, from 50 to 130 amino acids that are found in one or more of the human HER-2 orthologs and are different from the amino acids found in the ECD of human HER-2;

(c) an ECD-derived peptide that includes, in positions outside of the conserved T cell epitopes in the ECD of the human HER-2, from 120 to 130 amino acids that are found in one or more of the human HER-2 orthologs and are different from the amino acids found in the ECD of human HER-2;

(d) an ECD-derived peptide that includes, in positions outside of the conserved T cell epitopes in the ECD of the human HER-2, from 50 to 70 amino acids that are found in one or more of the human HER-2 orthologs and are different from the amino acids found in the ECD of human HER-2;

(e) a peptide comprising an ECD-derived peptide provided by the disclosure and a CTD-derived peptide provided by the disclosure, wherein the C-terminal end of the ECD-derived peptide is joined by a peptide bond to the N-terminal end of the CTD-derived peptide;

(f) a peptide comprising amino acids 23-645 of SEQ ID NO: 5;

(g) a peptide comprising amino acids 23-910 of SEQ ID NO: 3;

(h) a peptide comprising an ECD-derived peptide provided by the disclosure, a CTD-derived peptide provided by the disclosure, and an amino acid sequence of SEQ ID NO: 11, wherein the carboxy terminus of the ECD-derived peptide is joined to the amino terminus of the amino acid sequence of SEQ ID NO: 11 and the carboxy terminus of the amino acid sequence of SEQ ID NO: 11 is joined to the amino terminus of the CTD-derived peptide;

(i) a peptide comprising amino acids 23-940 of SEQ ID NO: 9.

(j) a peptide comprising an amino acids 25-647 of SEQ ID NO: 14;

(k) a peptide comprising an amino acids 25-912 of SEQ ID NO: 18; and (l) a peptide comprising an amino acids 25-956 of SEQ ID NO: 20.

In another aspect, the peptide composition further comprises one or more other tumor-associated antigens (TAAs). Examples of other TAA include Survivin, WT1, MUC1, CEA, NY-ESO-1, MAGE, MART-1 and other antigens disclosed in the article "The prioritization of cancer antigens: a national cancer institute pilot project for the acceleration of translational research" (Cheever M A, Clin Cancer Res. 15(17), 5323, 2009).

The peptide composition may further comprise a pharmaceutically acceptable excipient. Examples of suitable excipients include biocompatible oils, such as rape seed oil, sunflower oil, peanut oil, cotton seed oil, jojoba oil, squalan or squalene, physiological saline solution, preservatives and osmotic pressure controlling agents, carrier gases, pH-controlling agents, organic solvents, hydrophobic agents, enzyme inhibitors, water absorbing polymers, surfactants, absorption promoters, pH modifiers, and anti-oxidative agents.

In some embodiments, the peptide composition is a vaccine composition. The immunogenic HER-2 peptide in a composition, particularly a vaccine composition, of the invention may be linked to, conjugated to, or otherwise incorporated into a carrier for administration to a patient for systemic immunization. The term "carrier" refers to a substance or structure that an immunogen can be attached to or otherwise associated with for delivery of the immunogen to the recipient (e.g., patient). The carrier itself may be immunogenic. Examples of carriers include immunogenic peptides, immune CpG islands, limpet hemocyanin (KLH), tetanus toxoid (TT), cholera toxin subunit B (CTB), bacteria or bacterial ghosts, liposome, chitosome, virosomes, microspheres, dendritic cells, or their like. The immunogenic peptide can be conjugated to the carrier in a single or multiple ways in different combinations as mono-, di-, tri or oligomers. Such conjugations are known in the art, see for example: Th. H. Turpen, S. J. Reinl, Y. Charoenvit, S. L. Hoffmann, V. Fallarme in Bio/Technology, 1995, Vol. 13, pages 53 to 57, by examples of the conjugation of epitopes to macromolecular carriers, or by Wagner et al, 2005 J. Immunol. 174:976-982.

The vaccine composition may be used in conjunction with one or more adjuvants. The adjuvants may be formulated separately from the vaccine composition, or they may be part of the same vaccine composition formulation. Thus, in one embodiment, the vaccine composition further comprises one or more adjuvants. Suitable adjuvants include those suitable for use in mammals, preferably in humans. Examples of known suitable adjuvants include, but are not limited to, aluminum salts (such as alum, aluminum phosphate, aluminum hydroxide), CpG-containing nucleic acids (where the cytosine is unmethylated), QS21 (saponin adjuvant), MPL (Monophosphoryl Lipid A), 3DMPL (3-O-deacylated MPL), extracts from Aquilla, ISCOMS (see, e.g., Sjölander et al., *J. Leukocyte Biol.* 64:713 (1998); PCT Publication Nos. WO 90/03184, WO 96/11711, WO 00/48630, WO 98/36772, WO 00/41720, WO 06/134423 and WO 07/026190), LT/CT mutants, poly(D,L-lactide-co-glycolide) (PLG) microparticles, Quil A, interleukins, Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. Further exemplary adjuvants include, but are not limited to: (1) oil-in-water emulsion formulations (with or without other specific immunostimulating agents such as muramyl peptides (see below) or bacterial cell wall components), such as for example (a) MF59™ (PCT Publication No. WO 90/14837; Chapter 10 in *Vaccine design: the subunit and adjuvant approach*, eds. Powell & Newman, Plenum Press 1995), containing 5% Squalene, 0.5% Tween 80 (polyoxyethylene sorbitan mono-oleate), and 0.5% Span 85 (sorbitan trioleate) (optionally containing muramyl tripeptide covalently linked to dipalmitoyl phosphatidylethanolamine (MTP-PE)) formulated into submicron particles using a microfluidizer, (b) SAF, containing 10% Squalene, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia), may be used or particles generated therefrom such as ISCOMs (immunostimulating complexes), which ISCOMS may be devoid of additional detergent e.g. PCT Publication No. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (PCT Publication No. WO 99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL), optionally in the substantial absence of alum when used with pneumococcal saccharides (e.g. GB-2220221, EP-A-0689454, WO 00/56358); (6) combinations of 3dMPL with, for example, QS21 and/or oil-in-water emulsions (e.g. EP-A-0835318, EP-A-0735898, EP-A-0761231); (7) oligonucleotides comprising CpG motifs, i.e. containing at least one CG dinucleotide, where the cytosine is unmethylated (e.g., Krieg, *Vaccine* (2000) 19:618-622; Krieg, *Curr Opin Mol Ther* (2001) 3:15-24; WO 98/40100, WO 98/55495, WO 98/37919 and WO 98/52581); (8) a polyoxyethylene ether or a polyoxyethylene ester (e.g. WO 99/52549); (9) a polyoxyethylene sorbitan ester surfactant in combination with an octoxynol (e.g., WO 01/21207) or a polyoxyethylene alkyl ether or ester surfactant in combination with at least one additional non-ionic surfactant such as an octoxynol (e.g., WO 01/21152); (10) a saponin and an immunostimulatory oligonucleotide (e.g. a CpG oligonucleotide) (e.g., WO 00/62800); (11) an immunostimulant and a particle of metal salt (e.g. WO 00/23105); (12) a saponin and an oil-in-water emulsion (e.g. WO 99/11241); (13) a saponin (e.g. QS21)+3dMPL+IM2 (optionally+a sterol)(e.g. WO 98/57659); (14) other substances that act as immunostimulating agents to enhance the efficacy of the composition, such as Muramyl peptides including N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), (15) ligands for toll-like receptors (TLR), natural or synthesized (e.g. Kanzler et al., *Nature Med.* 13:1552-1559 (2007)), including TLR3 ligands such as polyI:C and similar compounds such as Hiltonol and Ampligen.

The peptide vaccine compositions can be prepared by methods known to one skilled in the art. Typically, such compositions may be prepared as injectables, either as liquid solutions, suspensions, or emulsions. The immunogenic peptide can also be encapsulated in liposomes. For suppositories, traditional binders and carriers may include, for example, polyalkylene glycols or triglycerides; such suppositories may be formed from mixtures containing the active ingredient in the range of 0.5 to 10 percent, preferably 1 to 2 percent. Oral formulations may include such normally employed excipients as, for example, pharmaceutical grades of mannitol, lactose, starch magnesium stearate, sodium saccharine, cellulose, magnesium carbonate, and the like. These compositions may take the form of solutions, suspensions, tablets, pills, capsules, sustained release formulations or powders and contain 10 percent to 95 percent of effective ingredient, preferably 25 to 70 percent.

The peptide vaccine compositions provide by the present invention may be administered by any suitable route, such as by injection, either subcutaneously or intramuscularly. It can also be administered in other manner compatible with the dosage formulation, and in such amount as will be prophylactically and/or therapeutically effective.

The peptide vaccine compositions can be administered in a single dose schedule, or in a multiple dose schedule. A multiple dose schedule is one in which a primary course of vaccination can include 1 or more separate doses, followed by other doses given at subsequent time intervals required to maintain and or reinforce the immune response, for example, at 1 to 4 months for a second dose, and if needed, a subsequent dose(s) after several months. Periodic boosters at intervals of 1 to 5 years, usually 3 years, are desirable to maintain the desired levels of protective immunity.

E. Compositions Comprising a Nucleic Acid Molecule (DNA Compositions)

The present invention also provides a composition comprising an isolated nucleic acid molecule provided by the present disclosure. The DNA compositions are useful for eliciting an immune response against HER-2 protein in a mammal including a human. In some embodiments, the DNA compositions are DNA vaccine compositions useful for inhibiting abnormal cell proliferation, providing protection against the development of cancer (used as a prophylactic), or for treatment of cancer (used as a therapeutic) associated with the HER-2 over expression.

In some specific embodiments, the nucleic acid molecule in a DNA composition comprises a nucleotide sequence that encodes an amino acid sequence selected from the group consisting of:

a) amino acids 23-910 of SEQ ID NO: 3;
b) amino acids 23-645 of SEQ ID NO: 5,
c) amino acids 23-940 of SEQ ID NO: 9;

d) amino acids 1-623 of SEQ ID NO: 12;
e) amino acids 25-647 of SEQ ID NO: 14;
f) amino acids 25-912 of SEQ ID NO: 18; and
g) amino acids 25-956 of SEQ ID NO.: 20.

In some further embodiments, the isolated nucleic acid molecule in the DNA composition described herein above further comprises a nucleotide sequence that encodes the amino acids of the signal sequence of human HER-2 protein. The amino acid sequence of the signal sequence corresponds to amino acids 1-22 of SEQ ID NOs: 1, 3, 5, or 9. Codons encoding additional amino acids may be inserted into the nucleotide sequence in order to facilitate the expression of the protein. For example, codons encoding alanine and serine may be inserted into the nucleotide sequence at the positions between amino acid positions 1 and 2 of the signal sequence. One example of such a modified signal sequence is an amino acid sequence that corresponds to amino acids 1-24 of SEQ ID NO: 14, 18, and 20.

In another specific embodiment, the nucleic acid molecule in the DNA composition comprises the nucleotide sequence of SEQ IDS NO: 4, 6, 10, 13, 15, 19, or 21.

In other embodiments, the DNA compositions are DNA vaccine compositions. The DNA compositions, including the DNA vaccine compositions, may further comprise a pharmaceutically acceptable excipient. Suitable pharmaceutically acceptable excipients for DNA compositions, including DNA vaccine compositions, are well known to those skilled in the art and include but are not limited to proteins, sugars, etc. Such excipients may be aqueous or non aqueous solutions, suspensions, and emulsions. Examples of non-aqueous excipients include propylene glycol, polyethylene glycol, vegetable oils such as olive oil, and injectable organic esters such as ethyl oleate. Examples of aqueous excipient include water, alcoholic/aqueous solutions, emulsions or suspensions, including saline and buffered media. Suitable excipients also include agents that assist in cellular uptake of the polynucleotide molecule. Examples of such agents are (i) chemicals that modify cellular permeability, such as bupivacaine, (ii) liposomes or viral particles for encapsulation of the polynucleotide, or (iii) cationic lipids or silica, gold, or tungsten microparticles which associate themselves with the polynucleotides. Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides. Cationic lipids are also known in the art and are commonly used for gene delivery. Such lipids include Lipofectin® also known as DOTMA (N—[I-(2,3-dioleyloxy)propyls N,N,N-trimethylammonium chloride), DOTAP (1,2-bis(oleyloxy)-3(trimethylammonio)propane), DDAB (dimethyldioctadecyl-ammonium bromide), DOGS (dioctadecylamidologlycyl spermine) and cholesterol derivatives such as DCChoi (3 beta-(N—(N',N'-dimethyl aminomethane)-carbamoyl)cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in WO 90/11092 as an example.

The nucleic acid molecule in the DNA vaccine composition may be a 'naked" nucleic acid molecule, i.e. simply in the form of an isolated DNA. Alternatively, the nucleic acid molecule can be incorporated into a vector. Examples of suitable vectors include those described herein above. The DNA compositions, including the vaccine compositions, can be introduced into tissues of an animal, including human, by a number of methods known in the art. Examples of suitable methods include: (1) injection with hypodermic needle, such as intramuscular (IM), intradermal (ID), intravenous, subcutaneous, and intraperitoneal injection; (2) pneumatic (jet) injection, gene gun injection, topical application (such as ocular and intravaginal application), and liposome-mediated delivery.

One particular method that may be used is gene gun delivery using the Particle Mediated Epidermal Delivery (PMED™) vaccine delivery device marketed by PowderMed. PMED is a needle-free method of administering vaccines to animals or to patients. The PMED system involves the precipitation of DNA onto microscopic gold particles that are then propelled by helium gas into the epidermis. The DNA-coated gold particles are delivered into the antigen-presenting cells (APCs) of the epidermis, and once inside the nuclei of the APCs, the DNA elutes off the gold and becomes transcriptionally active, producing encoded protein. This protein is then presented by the APCs to the lymphocytes to induce a T-cell-mediated immune response. The use of gold or tungsten microparticles used for gene delivery is also known in the art (see for example, WO 91/00359 and WO 93/17706). The microparticle-coated polynucleotide is injected via intradermal or intraepidermal routes using a needleless injection device, such as those described in U.S. Pat. No. 4,945,050, U.S. Pat. No. 5,015,580, and WO 94/24263.

F. Uses of the Compositions

In another aspect, the present disclosure provides a method of eliciting an immune response against HER-2 protein in a mammal, particularly a human, comprising administering to the mammal an effective amount of a peptide composition, or an effective amount of a DNA composition, provided by the present disclosure.

In another aspect, the present disclosure provides a method of treating cancer in a human subject associated with overexpression of HER-2 protein. The method comprises administering to the human subject an effective amount of a peptide composition, or a DNA composition, provided by the present disclosure. Examples of cancers that may be treated with the method include breast cancer, stomach cancer, ovarian cancer, lung cancer, bladder cancer, and prostate cancer.

In another aspect, the present disclosure provides a method of preventing cancer in a human associated with over expression of HER-2 protein. The method comprises administering to a human subject an effective amount of a peptide composition, or a DNA composition, provided by the present disclosure, wherein the human subject is at increased risk of developing a cancer associated with over expression of HER-2 protein. Examples of cancers that may be prevented with the method include breast cancer, stomach cancer, ovarian cancer, lung cancer, bladder cancer, and prostate cancer.

In still another aspect, the present disclosure provides a method of inhibiting abnormal cell proliferation in a human subject, comprising administering to the human subject an effective amount of a peptide composition, or a DNA composition, provided by the present disclosure.

The effective amount of the peptide or DNA in the composition, such as a vaccine composition, to be administered can be readily determined by a person skilled in the art, and will depend a number of factors, such as: (1) the subject to be treated, including the subject's the immune status and health, (2) the specific condition to be treated, (3) the specific active therapeutic agent used, (4) the degree of protection or treatment desired, (5) the administration schedule, and (6) whether any other therapeutic agents are used, and the therapeutic activity of the particular polypeptide. Suitable dosage ranges are of the order of several hundred micrograms effective ingredient per vaccination with a range from about 0.01 to 10 mg/kg/day, preferably in the range from about 0.1 to 1 mg/kg/day.

TABLE 5

Raw Sequence Listing
(Signal sequence underlined)

SEQ ID NO: 1: Amino Acid Sequence of Full Length Human HER-2 Protein

<u>MELAALCRWGLLLALLPPGAAS</u>TQVCTGTDMKLRLPASPETHLDMLRHLYQGCQVVQGNLELTYLPTNASLSFLQDIQ

EVQGYVLIAHNQVRQVPLQRLRIVRGTQLFEDNYALAVLDNGDPLNNTTPVTGASPGGLRELQLRSLTEILKGGVLIQ

RNPQLCYQDTILWKDIFHKNNQLALTLIDTNRSRACHPCSPMCKGSRCWGESSEDCQSLTRTVCAGGCARCKGPLPTD

CCHEQCAAGCTGPKHSDCLACLHFNHSGICELHCPALVTYNTDTFESMPNPEGRYTFGASCVTACPYNYLSTDVGSCT

LVCPLHNQEVTAEDGTQRCEKCSKPCARVCYGLGMEHLREVRAVTSANIQEFAGCKKIFGSLAFLPESFDGDPASNTA

PLQPEQLQVFETLEEITGYLYISAWPDSLPDLSVFQNLQVIRGRILHNGAYSLTLQGLGISWLGLRSLRELGSGLALI

HHNTHLCFVHTVPWDQLFRNPHQALLHTANRPEDECVGEGLACHQLCARGHCWGPGPTQCVNCSQFLRGQECVEECRV

LQGLPREYVNARHCLPCHPECQPQNGSVTCFGPEADQCVACAHYKDPPFCVARCPSGVKPDLSYMPIWKFPDEEGACQ

PCPINCTHSCVDLDDKGCPAEQRASPLTSIISAVVGILLVVVLGVVFGILIKRRQQKIRKYTMRRLLQETELVEPLTP

SGAMPNQAQMRILKETELRKVKVLGSGAFGTVYKGIWIPDGENVKIPVAIKVLRENTSPKANKEILDEAYVMAGVGSP

YVSRLLGICLTSTVQLVTQLMPYGCLLDHVRENRGRLGSQDLLNWCMQTAKGMSYLEDVRLVHRDLAARNVLVKSPNH

VKITDFGLARLLDIDETEYHADGGKVPIKWMALESILRRRFTHQSDVWSYGVTVWELMTFGAKPYDGIPAREIPDLLE

KGERLPQPPICTIDVYMIMVKCWMIDSECRPRFRELVSEFSRMARDPQRFVVIQNEDLGPASPLDSTFYRSLLEDDDM

GDLVDAEEYLVPQQGFFCPDPAPGAGGMVHHRHRSSSTRSGGGDLTLGLEPSEEEAPRSPLAPSEGAGSDVFDGDLGM

GAAKGLQSLPTHDPSPLQRYSEDPTVPLPSETDGYVAPLTCSPQPEYVNQPDVRPQPPSPREGPLPAARPAGATLERP

KTLSPGKNGVVKDVFAFGGAVENPEYLTPQGGAAPQPHPPPAFSPAFDNLYYWDQDPPERGAPPSTFKGTPTAENPEY

LGLDVPV

SEQ ID NO: 2: DNA Sequence Encoding Full Length Human HER-2 Protein of SEQ ID NO: 1

ATGGAGCTGGCGGCCTTGTGCCGCTGGGGGCTCCTCCTCGCCCTCTTGCCCCCCGGAGCCGCGAGCACCCAAGTGTGC

ACCGGCACAGACATGAAGCTGCGGCTCCCTGCCAGTCCCGAGACCCACCTGGACATGCTCCGCCACCTCTACCAGGGC

TGCCAGGTGGTGCAGGGAAACCTGGAACTCACCTACCTGCCCACCAATGCCAGCCTGTCCTTCCTGCAGGATATCCAG

GAGGTGCAGGGCTACGTGCTCATCGCTCACAACCAAGTGAGGCAGGTCCCACTGCAGAGGCTGCGGATTGTGCGAGGC

ACCCAGCTCTTTGAGGACAACTATGCCCTGGCCGTGCTAGACAATGGAGACCCGCTGAACAATACCACCCCTGTCACA

GGGGCCTCCCCAGGAGGCCTGCGGGAGCTGCAGCTTCGAAGCCTCACAGAGATCTTGAAAGGAGGGGTCTTGATCCAG

CGGAACCCCCAGCTCTGCTACCAGGACACGATTTTGTGGAAGGACATCTTCCACAAGAACAACCAGCTGGCTCTCACA

CTGATAGACACCAACCGCTCTCGGGCCTGCCACCCCTGTTCTCCGATGTGTAAGGGCTCCCGCTGCTGGGGAGAGAGT

TCTGAGGATTGTCAGAGCCTGACGCGCACTGTCTGTGCCGGTGGCTGTGCCCGCTGCAAGGGGCCACTGCCCACTGAC

TGCTGCCATGAGCAGTGTGCTGCCGGCTGCACGGGCCCCAAGCACTCTGACTGCCTGGCCTGCCTCCACTTCAACCAC

AGTGGCATCTGTGAGCTGCACTGCCCAGCCCTGGTCACCTACAACACAGACACGTTTGAGTCCATGCCCAATCCCGAG

GGCCGGTATACATTCGGCGCCAGCTGTGTGACTGCCTGTCCCTACAACTACCTTTCTACGGACGTGGGATCCTGCACC

CTCGTCTGCCCCCTGCACAACCAAGAGGTGACAGCAGAGGATGGAACACAGCGGTGTGAGAAGTGCAGCAAGCCCTGT

GCCCGAGTGTGCTATGGTCTGGGCATGGAGCACTTGCGAGAGGTGAGGGCAGTTACCAGTGCCAATATCCAGGAGTTT

GCTGGCTGCAAGAAGATCTTTGGGAGCCTGGCATTTCTGCCGGAGAGCTTTGATGGGGACCCAGCCTCCAACACTGCC

CCGCTCCAGCCAGAGCAGCTCCAAGTGTTTGAGACTCTGGAAGAGATCACAGGTTACCTATACATCTCAGCATGGCCG

GACAGCCTGCCTGACCTCAGCGTCTTCCAGAACCTGCAAGTAATCCGGGGACGAATTCTGCACAATGGCGCCTACTCG

CTGACCCTGCAAGGGCTGGGCATCAGCTGGCTGGGGCTGCGCTCACTGAGGGAACTGGGCAGTGGACTGGCCCTCATC

CACCATAACACCCACCTCTGCTTCGTGCACACGGTGCCCTGGGACCAGCTCTTTCGGAACCCGCACCAAGCTCTGCTC

TABLE 5-continued

Raw Sequence Listing
(Signal sequence underlined)

CACACTGCCAACCGGCCAGAGGACGAGTGTGTGGGCGAGGGCCTGGCCTGCCACCAGCTGTGCGCCCGAGGGCACTGC

TGGGGTCCAGGGCCCACCCAGTGTGTCAACTGCAGCCAGTTCCTTCGGGGCCAGGAGTGCGTGGAGGAATGCCGAGTA

CTGCAGGGGCTCCCCAGGGAGTATGTGAATGCCAGGCACTGTTTGCCGTGCCACCCTGAGTGTCAGCCCCAGAATGGC

TCAGTGACCTGTTTTGGACCGGAGGCTGACCAGTGTGTGGCCTGTGCCCACTATAAGGACCCTCCCTTCTGCGTGGCC

CGCTGCCCCAGCGGTGTGAAACCTGACCTCTCCTACATGCCCATCTGGAAGTTTCCAGATGAGGAGGGCGCATGCCAG

CCTTGCCCCATCAACTGCACCCACTCCTGTGTGGACCTGGATGACAAGGGCTGCCCCGCCGAGCAGAGAGCCAGCCCT

CTGACGTCCATCATCTCTGCGGTGGTTGGCATTCTGCTGGTCGTGGTCTTGGGGGTGGTCTTTGGGATCCTCATCAAG

CGACGGCAGCAGAAGATCCGGAAGTACACGATGCGGAGACTGCTGCAGGAAACGGAGCTGGTGGAGCCGCTGACACCT

AGCGGAGCGATGCCCAACCAGGCGCAGATGCGGATCCTGAAAGAGACGGAGCTGAGGAAGGTGAAGGTGCTTGGATCT

GGCGCTTTTGGCACAGTCTACAAGGGCATCTGGATCCCTGATGGGGAGAATGTGAAAATTCCAGTGGCCATCAAAGTG

TTGAGGGAAAACACATCCCCAAAGCCAACAAAGAAATCTTAGACGAAGCATACGTGATGGCTGGTGTGGGCTCCCCA

TATGTCTCCCGCCTTCTGGGCATCTGCCTGACATCCACGGTGCAGCTGGTGACACAGCTTATGCCCTATGGCTGCCTC

TTAGACCATGTCCGGGAAAACCGCGGACGCCTGGGCTCCCAGGACCTGCTGAACTGGTGTATGCAGATTGCCAAGGGG

ATGAGCTACCTGGAGGATGTGCGGCTCGTACACAGGGACTTGGCCGCTCGGAACGTGCTGGTCAAGAGTCCCAACCAT

GTCAAAATTACAGACTTCGGGCTGGCTCGGCTGCTGGACATTGACGAGACAGAGTACCATGCAGATGGGGGCAAGGTG

CCCATCAAGTGGATGGCGCTGGAGTCCATTCTCCGCCGGCGGTTCACCCACCAGAGTGATGTGTGGAGTTATGGTGTG

ACTGTGTGGGAGCTGATGACTTTTGGGGCCAAACCTTACGATGGGATCCCAGCCCGGGAGATCCCTGACCTGCTGGAA

AAGGGGGAGCGGCTGCCCCAGCCCCCCATCTGCACCATTGATGTCTACATGATCATGGTCAAATGTTGGATGATTGAC

TCTGAATGTCGGCCAAGATTCCGGGAGTTGGTGTCTGAATTCTCCCGCATGGCCAGGGACCCCCAGCGCTTTGTGGTC

ATCCAGAATGAGGACTTGGGCCCAGCCAGTCCCTTGGACAGCACCTTCTACCGCTCACTGCTGGAGGACGATGACATG

GGGGACCTGGTGGATGCTGAGGAGTATCTGGTACCCCAGCAGGGCTTCTTCTGTCCAGACCCTGCCCCGGGCGCTGGG

GGCATGGTCCACCACAGGCACCGCAGCTCATCTACCAGGAGTGGCGGTGGGGACCTGACACTAGGGCTGGAGCCCTCT

GAAGAGGAGGCCCCCAGGTCTCCACTGGCACCCTCCGAAGGGGCTGGCTCCGATGTATTTGATGGTGACCTGGGAATG

GGGGCAGCCAAGGGGCTGCAAAGCCTCCCCACACATGACCCCAGCCCTCTACAGCGGTACAGTGAGGACCCCACAGTA

CCCCTGCCCTCTGAGACTGATGGCTACGTTGCCCCCCTGACCTGCAGCCCCAGCCTGAATATGTGAACCAGCCAGAT

GTTCGGCCCCAGCCCCCTTCGCCCCGAGAGGGCCCTCTGCCTGCTGCCCGACCTGCTGGTGCCACTCTGGAAAGGCCC

AAGACTCTCTCCCCAGGGAAGAATGGGGTCGTCAAAGACGTTTTTGCCTTTGGGGGTGCCGTGGAGAACCCCGAGTAC

TTGACACCCCAGGGAGGAGCTGCCCCTCAGCCCCACCCTCCTCCTGCCTTCAGCCCAGCCTTCGACAACCTCTATTAC

TGGGACCAGGACCCACCAGAGCGGGGGCTCCACCCAGCACCTTCAAAGGGACACCTACGGCAGAGAACCCAGAGTAC

CTGGGTCTGGACGTGCCAGTG

SEQ ID No: 3: Amino Acid Sequence of RaDHER2-1 Peptide

<u>MELAALCRWGLLLALLPPGAAS</u>TQVCTGTDMKLRLPASPETHLDIVRHLYQGCQVVQGNLELTYVPANASLSFLQDIQ

EVQGYMLIAHSRVKHIPLQRLRIVRGTQLFEDNYALAVLDNRDLQDNATSAAGRTPEGLRELQLRSLTEILKGGVLIR

GSPQLCHQDMVLWEDVLRKNNQLTPVDMDTNRSRACPPCAPACRDNHCWGASPGDCNSLTGTICTSGCARCKGRQPTD

CCHEQCAAGCTGPKHSDCLACLHFNHSGICELHCPSLIIYNTDTFESMHNPEGRYTFGASCVTTCPYNYLSTEVGSCT

LVCPPNNQEVTAEDGTQRCEKCSKPCARVCYGLGMEHLRGARAITSDNVQDFVGCKKIFGSLAFLPESFDGDPSSGIA

PLRPEHLRVFEALEEITGYLYISAWPESFRNLSVLQNLRIIRGRVLHDGAYSLALQGLGIRSLGLRSLQELGSGLALV

HRNARLCFVNTVPWAQLFRNPHQALLHSGNPSEDECGLKDFVCNSLCAHGHCWGPGPTHCVNCSQFLPGQECVKECRV

TABLE 5-continued

Raw Sequence Listing
(Signal sequence underlined)

WKGLPREYVSDKRCLPCHSECQPQNSTETCYGSEADQCEACTHYKDPPFCVARCPSGVKPDLSYMPIWKFPDEEGACQ

PCPINCTHSCADLDDRGCPAENEDLGPSSPMDSTFYRSLLEDEDMGELVDAEEYLVPQQGFFSPDPTPGTGSTAHRRH

RSSSARNGGGDLTLGMEPSGEGPPRSPRAPSEGTGSDVFDGDLAVGVTKGLQSLSPQDLSPLQRYSEDPTLPLPSETD

GKVAPLSCSPQPEFVNQSDVQPKSPLTPEGPPSPARPTGATLERAKTLSPGKNGVVKDVFTFGGAVENPEFLAPREGT

ASPPHPSPAFSPAFDNLFFWDQNSSEQGPPPSNFEGTPTAENPEFLGLDVPV.

SEQ ID NO: 4: DNA Sequence Encoding the RaDHER2-1 Peptide
of SEQ ID No: 3

ATGGAACTGGCCGCCCTGTGTAGATGGGGACTGCTGCTGGCCCTGCTGCCCCTGGCGCTGCTTCCACACAGGTGTGC

ACCGGCACCGACATGAAGCTGAGACTGCCCGCCAGCCCTGAGACCCACCTGGACATCGTGCGGCACCTGTACCAGGGC

TGTCAGGTGGTGCAGGGCAACCTGGAACTGACCTACGTGCCCGCCAACGCCAGCCTGAGCTTCCTGCAGGACATCCAG

GAAGTGCAGGGCTACATGCTGATCGCCCACAGCCGGGTGAAGCACATCCCCCTGCAGCGGCTGAGAATCGTGCGGGC

ACCCAGCTGTTCGAGGACAACTACGCCCTGGCCGTGCTGGACAACCGGGACCTGCAGGATAATGCCACCTCCGCCGCT

GGCAGAACACCTGAGGGCCTGCGGGAGCTGCAGCTGAGAAGCCTGACCGAGATCCTGAAGGGCGGCGTGCTGATCAGA

GGCAGCCCCCAGCTGTGCCATCAGGATATGGTGCTGTGGGAGGACGTGCTGCGGAAGAACAACCAGCTGACCCCCGTG

GACATGGACACCAACCGGTCCAGAGCCTGCCCTCCTTGCGCCCCTGCCTGCAGGGATAACCACTGCTGGGGCGCCAGC

CCAGGCGATTGCAACAGCCTGACCGGCACCATCTGCACCAGCGGCTGCGCCAGATGCAAGGGCAGACAGCCCACCGAC

TGCTGCCATGAGCAGTGTGCCGCCGGATGTACCGGCCCCAAGCACAGCGACTGCCTGGCCTGCCTGCACTTCAACCAC

AGCGGCATCTGCGAGCTGCACTGCCCCAGCCTGATCATCTACAACACCGACACCTTCGAGAGCATGCACAACCCCGAG

GGCAGATACACCTTCGGCGCCAGCTGCGTGACCACCTGCCCCTACAACTACCTGAGCACCGAAGTGGGCAGCTGCACC

CTGGTGTGCCCCCCCAACAACCAGGAAGTGACCGCCGAGGACGGCACCCAGAGATGCGAGAAGTGCAGCAAGCCCTGC

GCCAGAGTGTGTTACGGCCTGGGCATGGAACATCTGAGGGGCGCCAGGGCCATCACCAGCGACAACGTGCAGGACTTC

GTGGGCTGCAAGAAGATTTTCGGCTCCCTGGCCTTCCTGCCCGAGAGCTTCGACGGCGACCCTAGCAGCGGCATCGCC

CCCCTGAGACCAGAGCACCTGCGGGTGTTCGAGGCCCTGGAAGAGATCACCGGCTACCTGTACATCAGCGCCTGGCCC

GAGTCCTTCCGGAACCTGAGCGTGCTGCAGAACCTGCGGATCATCCGGGGCAGAGTGCTGCACGATGGCGCCTATAGC

CTCGCTCTGCAGGGACTGGGAATCAGAAGCCTGGGCCTGCGGTCTCTGCAGGAACTGGGCAGCGGACTGGCCCTGGTG

CACCGGAACGCCCGGCTGTGCTTCGTGAATACCGTGCCCTGGGCCCAGCTGTTTAGGAACCCCCACCAGGCTCTGCTG

CACAGCGGCAACCCCAGCGAGGACGAGTGCGGCCTGAAGGACTTTGTGTGCAACTCCCTGTGCGCCCACGGACACTGT

TGGGGACCTGGACCTACCCACTGCGTGAACTGCAGCCAGTTTCTGCCTGGCCAGGAATGCGTGAAAGAATGCAGAGTG

TGGAAGGGCCTGCCTCGGGAGTACGTGAGCGACAAGCGGTGCCTGCCCTGCCACAGCGAGTGCCAGCCCCAGAACAGC

ACCGAGACCTGCTACGGCAGCGAGGCCGACCAGTGTGAGGCCTGCACCCACTACAAGGACCCCCCCTTCTGCGTGGCC

AGATGCCCTAGCGGCGTGAAGCCCGACCTGAGCTACATGCCCATCTGGAAGTTCCCCGACGAGGAAGGCGCCTGCCAG

CCCTGCCCCATCAACTGCACCCACAGCTGCGCCGACCTGGACGATAGAGGCTGCCCTGCCGAGAACGAGGATCTGGGC

CCCAGCAGCCCTATGGACAGCACCTTCTACAGATCCCTGCTGGAAGATGAGGACATGGGCGAACTGGTGGACGCCGAG

GAATACCTGGTGCCTCAGCAGGGCTTCTTCAGCCCCGATCCTACCCCTGGCACCGGCAGCACAGCCCATCGGCGGCAC

AGAAGCAGTTCTGCTAGAAATGGCGGCGGAGACCTGACCCTGGGAATGGAACCTAGCGGCGAGGGCCCTCCTAGAAGC

CCTAGAGCACCTTCCGAAGGGACCGGCTCCGACGTGTTCGATGGCGATCTGGCCGTGGGCGTGACAAAGGGCCTGCAG

TCTCTCTCTCCACAGGATCTGTCTCCACTGCAGAGATACAGCGAGGACCCCACCCTGCCTCTGCCTAGCGAGACCGAC

GGCAAGGTGGCCCCTCTGAGCTGTAGCCCCCAGCCCGAGTTCGTGAACCAGAGCGACGTGCAGCCCAAGAGCCCTCTG

ACCCCTGAGGGACCCCCTAGCCCTGCCAGACCTACCGGCGCCACCCTGGAAAGAGCCAAGACCCTGAGCCCCGGCAAG

TABLE 5-continued

Raw Sequence Listing
(Signal sequence underlined)

AACGGCGTGGTGAAGGACGTGTTCACCTTTGGCGGAGCCGTGGAGAACCCTGAGTTCCTGGCCCCAAGAGAGGGCACA

GCCAGCCCTCCTCACCCCAGCCCAGCCTTCAGCCCTGCCTTCGACAACCTGTTCTTCTGGGACCAGAATTCTAGTGAA

CAGGGACCTCCACCCAGCAATTTCGAGGGCACCCCCACCGCCGAGAATCCCGAGTTTCTGGGCCTGGACGTGCCCGTG

TAG

SEQ ID NO: 5: Amino Acid Sequence of ECD-derived Peptide 1(ECD1)

<u>MELAALCRWGLLLALLPPGAAS</u>TQVCTGTDMKLRLPASPETHLDIVRHLYQGCQVVQGNLELTYVPANASLSFLQDIQ

EVQGYMLIAHSRVKHIPLQRLRIVRGTQLFEDNYALAVLDNRDLQDNATSAAGRTPEGLRELQLRSLTEILKGGVLIR

GSPQLCHQDMVLWEDVLRKNNQLTPVDMDTNRSRACPPCAPACRDNHCWGASPGDCNSLTGTICTSGCARCKGRQPTD

CCHEQCAAGCTGPKHSDCLACLHFNHSGICELHCPSLIIYNTDTFESMHNPEGRYTFGASCVTTCPYNYLSTEVGSCT

LVCPPNNQEVTAEDGTQRCEKCSKPCARVCYGLGMEHLRGARAITSDNVQDFVGCKKIFGSLAFLPESFDGDPSSGIA

PLRPEHLRVFEALEEITGYLYISAWPESFRNLSVLQNLRIIRGRVLHDGAYSLALQGLGIRSLGLRSLQELGSGLALV

HRNARLCFVNTVPWAQLFRNPHQALLHSGNPSEDECGLKDFVCNSLCAHGHCWGPGPTHCVNCSQFLPGQECVKECRV

WKGLPREYVSDKRCLPCHSECQPQNSTETCYGSEADQCEACTHYKDPPFCVARCPSGVKPDLSYMPIWKFPDEEGACQ

PCPINCTHSCADLDDRGCPAE

SEQ ID NO: 6: DNA Sequence Encoding the Amino Acid sequence of
ECD1 (SEQ ID NO: 5)

ATGGAACTGGCCGCCCTGTGTAGATGGGGACTGCTGCTGGCCCTGCTGCCCCCTGGCGCTGCTTCCACACAGGTGTGC

ACCGGCACCGACATGAAGCTGAGACTGCCCGCCAGCCCTGAGACCCACCTGGACATCGTGCGGCACCTGTACCAGGGC

TGTCAGGTGGTGCAGGGCAACCTGGAACTGACCTACGTGCCCGCCAACGCCAGCCTGAGCTTCCTGCAGGACATCCAG

GAAGTGCAGGGCTACATGCTGATCGCCCACAGCCGGGTGAAGCACATCCCCCTGCAGCGGCTGAGAATCGTGCGGGGC

ACCCAGCTGTTCGAGGACAACTACGCCCTGGCCGTGCTGGACAACCGGGACCTGCAGGATAATGCCACCTCCGCCGCT

GGCAGAACACCTGAGGGCCTGCGGGAGCTGCAGCTGAGAAGCCTGACCGAGATCCTGAAGGGCGGCGTGCTGATCAGA

GGCAGCCCCAGCTGTGCCATCAGGATATGGTGCTGTGGAGGACGTGCTGCGGAAGAACAACCAGCTGACCCCCGTG

GACATGGACACCAACCGGTCCAGAGCCTGCCCTCCTTGCGCCCCTGCCTGCAGGGATAACCACTGCTGGGGCGCCAGC

CCAGGCGATTGCAACAGCCTGACCGGCACCATCTGCACCAGCGGCTGCGCCAGATGCAAGGGCAGACAGCCCACCGAC

TGCTGCCATGAGCAGTGTGCCGCCGGATGTACCGGCCCCAAGCACAGCGACTGCCTGGCCTGCCTGCACTTCAACCAC

AGCGGCATCTGCGAGCTGCACTGCCCCAGCCTGATCATCTACAACACCGACACCTTCGAGAGCATGCACAACCCCGAG

GGCAGATACACCTTCGGCGCCAGCTGCGTGACCACCTGCCCCTACAACTACCTGAGCACCGAAGTGGGCAGCTGCACC

CTGGTGTGCCCCCCCAACAACCAGGAAGTGACCGCCGAGGACGGCACCCAGAGATGCGAGAAGTGCAGCAAGCCCTGC

GCCAGAGTGTGTTACGCCTGGGCATGGAACATCTGAGGGGCGCCAGGGCCATCACCAGCGACAACGTGCAGGACTTC

GTGGGCTGCAAGAAGATTTTCGGCTCCCTGGCCTTCCTGCCCGAGAGCTTCGACGGCGACCCTAGCAGCGGCATCGCC

CCCCTGAGACCAGAGCACCTGCGGGTGTTCGAGGCCCTGGAAGAGATCACCGGCTACCTGTACATCAGCGCCTGGCCC

GAGTCCTTCCGGAACCTGAGCGTGCTGCAGAACCTGCGGATCATCCGGGGCAGAGTGCTGCACGATGGCGCCTATAGC

CTCGCTCTGCAGGGACTGGGAATCAGAAGCCTGGGCCTGCGGTCTCTGCAGGAACTGGGCAGCGGACTGGCCCTGGTG

CACCGGAACGCCCGGCTGTGCTTCGTGAATACCGTGCCCTGGGCCCAGCTGTTTAGGAACCCCCACCAGGCTCTGCTG

CACAGCGGCAACCCCAGCGAGGACGAGTGCGGCCTGAAGGACTTTGTGTGCAACTCCCTGTGCGCCCACGGACACTGT

TGGGGACCTGGACCTACCCACTGCGTGAACTGCAGCCAGTTTCTGCCTGGCCAGGAATGCGTGAAAGAATGCAGAGTG

TGGAAGGGCCTGCCTCGGGAGTACGTGAGCGACAAGCGGTGCCTGCCCTGCCACAGCGAGTGCCAGCCCCAGAACAGC

ACCGAGACCTGCTACGGCAGCGAGGCCGACCAGTGTGAGGCCTGCACCCACTACAAGGACCCCCCCTTCTGCGTGGCC

TABLE 5-continued

Raw Sequence Listing
(Signal sequence underlined)

AGATGCCCTAGCGGCGTGAAGCCCGACCTGAGCTACATGCCCATCTGGAAGTTCCCCGACGAGGAAGGCGCCTGCCAG

CCCTGCCCCATCAACTGCACCCACAGCTGCGCCGACCTGGACGATAGAGGCTGCCCTGCCGAG

SEQ ID NO: 7: Amino Acid Sequence of CTD-derived Peptide 1 (CTD1)

NEDLGPSSPMDSTFYRSLLEDEDMGELVDAEEYLVPQQGFFSPDPTPGTGSTAHRRHRSSSARNGGGDLTLGMEPSGE

GPPRSPRAPSEGTGSDVFDGDLAVGVTKGLQSLSPQDLSPLQRYSEDPTLPLPSETDGKVAPLSCSPQPEFVNQSDVQ

PKSPLTPEGPPSPARPTGATLERAKTLSPGKNGVVKDVFTFGGAVENPEFLAPREGTASPPHPSPAFSPAFDNLFFWD

QNSSEQGPPPSNFEGTPTAENPEFLGLDVPV

SEQ ID NO: 8: DNA Sequence Encoding the Amino Acid Sequence of
CTD-derived Peptide 1 (CTD1) of SEQ ID NO: 7

AACGAGGATCTGGGCCCCAGCAGCCCTATGGACAGCACCTTCTACAGATCCCTGCTGGAAGATGAGGACATGGGCGAA

CTGGTGGACGCCGAGGAATACCTGGTGCCTCAGCAGGGCTTCTTCAGCCCCGATCCTACCCCTGGCACCGGCAGCACA

GCCCATCGGCGGCACAGAAGCAGTTCTGCTAGAAATGGCGGCGGAGACCTGACCCTGGGAATGGAACCTAGCGGCGAG

GGCCCTCCTAGAAGCCCTAGAGCACCTTCCGAAGGGACCGGCTCCGACGTGTTCGATGGCGATCTGGCCGTGGGCGTG

ACAAAGGGCCTGCAGTCTCTCTCTCCACAGGATCTGTCTCCACTGCAGAGATACAGCGAGGACCCCACCCTGCCTCTG

CCTAGCGAGACCGACGGCAAGGTGGCCCCTCTGAGCTGTAGCCCCCAGCCCGAGTTCGTGAACCAGAGCGACGTGCAG

CCCAAGAGCCCTCTGACCCCTGAGGGACCCCCTAGCCCTGCCAGACCTACCGGCGCCACCCTGGAAAGAGCCAAGACC

CTGAGCCCCGGCAAGAACGGCGTGGTGAAGGACGTGTTCACCTTTGGCGGAGCCGTGGAGAACCCTGAGTTCCTGGCC

CCAAGAGAGGGCACAGCCAGCCCTCCTCACCCCAGCCCAGCCTTCAGCCCTGCCTTCGACAACCTGTTCTTCTGGGAC

CAGAATTCTAGTGAACAGGGACCTCCACCCAGCAATTTCGAGGGCACCCCCACCGCCGAGAATCCCGAGTTTCTGGGC

CTGGACGTGCCCGTGTAG

SEQ ID NO: 9. Amino Acid Sequence of a Peptide Composed of ECD1,
TMD1, and CTD1

<u>MELAALCRWGLLLALLPPGAAST</u>QVCTGTDMKLRLPASPETHLDIVRHLYQGCQVVQGNLELTYVPANASLSFLQDIQ

EVQGYMLIAHSRVKHIPLQRLRIVRGTQLFEDNYALAVLDNRDLQDNATSAAGRTPEGLRELQLRSLTEILKGGVLIR

GSPQLCHQDMVLWEDVLRKNNQLTPVDMDTNRSRACPPCAPACRDNHCWGASPGDCNSLTGTICTSGCARCKGRQPTD

CCHEQCAAGCTGPKHSDCLACLHFNHSGICELHCPSLIIYNTDTFESMHNPEGRYTFGASCVTTCPYNYLSTEVGSCT

LVCPPNNQEVTAEDGTQRCEKCSKPCARVCYGLGMEHLRGARAITSDNVQDFVGCKKIFGSLAFLPESFDGDPSSGIA

PLRPEHLRVFEALEEITGYLYISAWPESFRNLSVLQNLRIIRGRVLHDGAYSLALQGLGIRSLGLRSLQELGSGLALV

HRNARLCFVNTVPWAQLFRNPHQALLHSGNPSEDECGLKDFVCNSLCAHGHCWGPGPTHCVNCSQFLPGQECVKECRV

WKGLPREYVSDKRCLPCHSECQPQNSTETCYGSEADQCEACTHYKDPPFCVARCPSGVKPDLSYMPIWKFPDEEGACQ

PCPINCTHSCADLDDRGCPAEQRASPLTSIVSAVVGILLVVVLGVVFGILINEDLGPSSPMDSTFYRSLLEDEDMGEL

VDAEEYLVPQQGFFSPDPTPGTGSTAHRRHRSSSARNGGGDLTLGMEPSGEGPPRSPRAPSEGTGSDVFDGDLAVGVT

KGLQSLSPQDLSPLQRYSEDPTLPLPSETDGKVAPLSCSPQPEFVNQSDVQPKSPLTPEGPPSPARPTGATLERAKTL

SPGKNGVVKDVFTFGGAVENPEFLAPREGTASPPHPSPAFSPAFDNLFFWDQNSSEQGPPPSNFEGTPTAENPEFLGL

DVPV

SEQ ID NO: 10: DNA Sequence Encoding the Amino Acid Sequence of
SEQ ID NO: 9

ATGGAACTGGCCGCCCTGTGTAGATGGGGACTGCTGCTGGCCCTGCTGCCCCTGGCGCTGCTTCCACACAGGTGTGC

ACCGGCACCGACATGAAGCTGAGACTGCCCGCCAGCCCTGAGACCCACCTGGACATCGTGCGGCACCTGTACCAGGGC

TGTCAGGTGGTGCAGGGCAACCTGGAACTGACCTACGTGCCCGCCAACGCCAGCCTGAGCTTCCTGCAGGACATCCAG

TABLE 5-continued

Raw Sequence Listing
(Signal sequence underlined)

GAAGTGCAGGGCTACATGCTGATCGCCCACAGCCGGGTGAAGCACATCCCCCTGCAGCGGCTGAGAATCGTGCGGGGC
ACCCAGCTGTTCGAGGACAACTACGCCCTGGCCGTGCTGGACAACCGGGACCTGCAGGATAATGCCACCTCCGCCGCT
GGCAGAACACCTGAGGGCCTGCGGGAGCTGCAGCTGAGAAGCCTGACCGAGATCCTGAAGGGCGGCGTGCTGATCAGA
GGCAGCCCCCAGCTGTGCCATCAGGATATGGTGCTGTGGGAGGACGTGCTGCGGAAGAACAACCAGCTGACCCCCGTG
GACATGGACACCAACCGGTCCAGAGCCTGCCCTCCTTGCGCCCCTGCCTGCAGGGATAACCACTGCTGGGGCGCCAGC
CCAGGCGATTGCAACAGCCTGACCGGCACCATCTGCACCAGCGGCTGCGCCAGATGCAAGGGCAGACAGCCCACCGAC
TGCTGCCATGAGCAGTGTGCCGCCGGATGTACCGGCCCCAAGCACAGCGACTGCCTGGCCTGCCTGCACTTCAACCAC
AGCGGCATCTGCGAGCTGCACTGCCCCAGCCTGATCATCTACAACACCGACACCTTCGAGAGCATGCACAACCCCGAG
GGCAGATACACCTTCGGCGCCAGCTGCGTGACCACCTGCCCCTACAACTACCTGAGCACCGAAGTGGGCAGCTGCACC
CTGGTGTGCCCCCCCAACAACCAGGAAGTGACCGCCGAGGACGGCACCCAGAGATGCGAGAAGTGCAGCAAGCCCTGC
GCCAGAGTGTGTTACGCCTGGGCATGGAACATCTGAGGGGCGCCAGGGCCATCACCAGCGACAACGTGCAGGACTTC
GTGGGCTGCAAGAAGATTTTCGGCTCCCTGGCCTTCCTGCCCGAGAGCTTCGACGGCGACCCTAGCAGCGGCATCGCC
CCCCTGAGACCAGAGCACCTGCGGGTGTTCGAGGCCCTGGAAGAGATCACCGGCTACCTGTACATCAGCGCCTGGCCC
GAGTCCTTCCGGAACCTGAGCGTGCTGCAGAACCTGCGGATCATCCGGGGCAGAGTGCTGCACGATGGCGCCTATAGC
CTCGCTCTGCAGGGACTGGGAATCAGAAGCCTGGGCCTGCGGTCTCTGCAGGAACTGGGCAGCGGACTGGCCCTGGTG
CACCGGAACGCCCGGCTGTGCTTCGTGAATACCGTGCCCTGGGCCCAGCTGTTTAGGAACCCCCACCAGGCTCTGCTG
CACAGCGGCAACCCCAGCGAGGACGAGTGCGGCCTGAAGGACTTTGTGTGCAACTCCCTGTGCGCCCACGGACACTGT
TGGGGACCTGGACCTACCCACTGCGTGAACTGCAGCCAGTTTCTGCCTGGCCAGGAATGCGTGAAAGAATGCAGAGTG
TGGAAGGGCCTGCCTCGGGAGTACGTGAGCGACAAGCGGTGCCTGCCCTGCCACAGCGAGTGCCAGCCCCAGAACAGC
ACCGAGACCTGCTACGGCAGCGAGGCCGACCAGTGTGAGGCCTGCACCCACTACAAGGACCCCCCCTTCTGCGTGGCC
AGATGCCCTAGCGGCGTGAAGCCCGACCTGAGCTACATGCCCATCTGGAAGTTCCCCGACGAGGAAGGCGCCTGCCAG
CCCTGCCCCATCAACTGCACCCACAGCTGCGCCGACCTGGACGATAGAGGCTGCCCTGCCGAGCAGAGAGCCAGCCCT
CTGACGTCCATCGTCTCTGCGGTGGTTGGCATTCTGCTGGTCGTGGTCTTGGGGGTGGTCTTTGGGATCCTCATCAAC
GAGGATCTGGGCCCCAGCAGCCCTATGGACAGCACCTTCTACAGATCCCTGCTGGAAGATGAGGACATGGGCGAACTG
GTGGACGCCGAGGAATACCTGGTGCCTCAGCAGGGCTTCTTCAGCCCCGATCCTACCCCTGGCACCGGCAGCACAGCC
CATCGGCGGCACAGAAGCAGTTCTGCTAGAAATGGCGGCGGAGACCTGACCCTGGGAATGGAACCTAGCGGCGAGGGC
CCTCCTAGAAGCCCTAGAGCACCTTCCGAAGGGACCGGCTCCGACGTGTTCGATGGCGATCTGGCCGTGGGCGTGACA
AAGGGCCTGCAGTCTCTCTCTCCACAGGATCTGTCTCCACTGCAGAGATACAGCGAGGACCCCACCCTGCCTCTGCCT
AGCGAGACCGACGGCAAGGTGGCCCCTCTGAGCTGTAGCCCCAGCCCGAGTTCGTGAACCAGAGCGACGTGCAGCCC
AAGAGCCCTCTGACCCCTGAGGGACCCCCTAGCCCTGCCAGACCTACCGGCGCCACCCTGGAAAGAGCCAAGACCCTG
AGCCCCGGCAAGAACGGCGTGGTGAAGGACGTGTTCACCTTTGGCGGAGCCGTGGAGAACCCTGAGTTCCTGGCCCCA
AGAGAGGGCACAGCCAGCCCTCCTCACCCCAGCCCAGCCTTCAGCCCTGCCTTCGACAACCTGTTCTTCTGGGACCAG
AATTCTAGTGAACAGGGACCTCCACCCAGCAATTTCGAGGGCACCCCCACCGCCGAGAATCCCGAGTTTCTGGGCCTG
GACGTGCCCGTG

SEQ ID NO: 11. Amino Acid Sequence of TMD-derived Peptide 1 (TMD1)

QRASPLTSIVSAVVGILLVVVLGVVFGILI

TABLE 5-continued

Raw Sequence Listing
(Signal sequence underlined)

SEQ. ID NO: 12: Amino Acid Sequence of ECD-derived Peptide 1
(ECD1) without Signal Sequence

TQVCTGTDMKLRLPASPETHLDIVRHLYQGCQVVQGNLELTYVPANASLSFLQDIQEVQGYMLIAHSRVKHIPLQRLR

IVRGTQLFEDNYALAVLDNRDLQDNATSAAGRTPEGLRELQLRSLTEILKGGVLIRGSPQLCHQDMVLWEDVLRKNNQ

LTPVDMDTNRSRACPPCAPACRDNHCWGASPGDCNSLTGTICTSGCARCKGRQPTDCCHEQCAAGCTGPKHSDCLACL

HFNHSGICELHCPSLIIYNTDTFESMHNPEGRYTFGASCVTTCPYNYLSTEVGSCTLVCPPNNQEVTAEDGTQRCEKC

SKPCARVCYGLGMEHLRGARAITSDNVQDFVGCKKIFGSLAFLPESFDGDPSSGIAPLRPEHLRVFEALEEITGYLYI

SAWPESFRNLSVLQNLRIIRGRVLHDGAYSLALQGLGIRSLGLRSLQELGSGLALVHRNARLCFVNTVPWAQLFRNPH

QALLHSGNPSEDECGLKDFVCNSLCAHGHCWGPGPTHCVNCSQFLPGQECVKECRVWKGLPREYVSDKRCLPCHSECQ

PQNSTETCYGSEADQCEACTHYKDPPFCVARCPSGVKPDLSYMPIWKFPDEEGACQPCPINCTHSCADLDDRGCPAE

SEQ ID NO: 13: DNA Sequence Encoding the Amino Acid Sequence of
ECD-derived Peptide 1 of SEQ ID NO: 12

ACACAGGTGTGCACCGGCACCGACATGAAGCTGAGACTGCCCGCCAGCCCTGAGACCCACCTGGACATCGTGCGGCAC

CTGTACCAGGGCTGTCAGGTGGTGCAGGGCAACCTGGAACTGACCTACGTGCCCGCCAACGCCAGCCTGAGCTTCCTG

CAGGACATCCAGGAAGTGCAGGGCTACATGCTGATCGCCCACAGCCGGGTGAAGCACATCCCCCTGCAGCGGCTGAGA

ATCGTGCGGGGCACCCAGCTGTTCGAGGACAACTACGCCCTGGCCGTGCTGGACAACCGGGACCTGCAGGATAATGCC

ACCTCCGCCGCTGGCAGAACACCTGAGGGCCTGCGGGAGCTGCAGCTGAGAAGCCTGACCGAGATCCTGAAGGGCGGC

GTGCTGATCAGAGGCAGCCCCCAGCTGTGCCATCAGGATATGGTGCTGTGGGAGGACGTGCTGCGGAAGAACAACCAG

CTGACCCCCGTGGACATGGACACCAACCGGTCCAGAGCCTGCCCTCCTTGCGCCCCTGCCTGCAGGGATAACCACTGC

TGGGGCGCCAGCCCAGGCGATTGCAACAGCCTGACCGGCACCATCTGCACCAGCGGCTGCGCCAGATGCAAGGGCAGA

CAGCCCACCGACTGCTGCCATGAGCAGTGTGCCGCCGGATGTACCGGCCCCAAGCACAGCGACTGCCTGGCCTGCCTG

CACTTCAACCACAGCGGCATCTGCGAGCTGCACTGCCCCAGCCTGATCATCTACAACACCGACACCTTCGAGAGCATG

CACAACCCCGAGGGCAGATACACCTTCGGCGCCAGCTGCGTGACCACCTGCCCCTACAACTACCTGAGCACCGAAGTG

GGCAGCTGCACCCTGGTGTGCCCCCCCAACAACCAGGAAGTGACCGCCGAGGACGGCACCCAGAGATGCGAGAAGTGC

AGCAAGCCCTGCGCCAGAGTGTGTTACGGCCTGGGCATGGAACATCTGAGGGGCGCCAGGGCCATCACCAGCGACAAC

GTGCAGGACTTCGTGGGCTGCAAGAAGATTTTCGGCTCCCTGGCCTTCCTGCCCGAGAGCTTCGACGGCGACCCTAGC

AGCGGCATCGCCCCCCTGAGACCAGAGCACCTGCGGGTGTTCGAGGCCCTGGAAGAGATCACCGGCTACCTGTACATC

AGCGCCTGGCCCGAGTCCTTCCGGAACCTGAGCGTGCTGCAGAACCTGCGGATCATCCGGGGCAGAGTGCTGCACGAT

GGCGCCTATAGCCTCGCTCTGCAGGGACTGGGAATCAGAAGCCTGGGCCTGCGGTCTCTGCAGGAACTGGGCAGCGGA

CTGGCCCTGGTGCACCGGAACGCCCGGCTGTGCTTCGTGAATACCGTGCCCTGGGCCCAGCTGTTTAGGAACCCCCAC

CAGGCTCTGCTGCACAGCGGCAACCCCAGCGAGGACGAGTGCGGCCTGAAGGACTTTGTGTGCAACTCCCTGTGCGCC

CACGGACACTGTTGGGGACCTGGACCTACCCACTGCGTGAACTGCAGCCAGTTTCTGCCTGGCCAGGAATGCGTGAAA

GAATGCAGAGTGTGGAAGGGCCTGCCTCGGGAGTACGTGAGCGACAAGCGGTGCCTGCCCTGCCACAGCGAGTGCCAG

CCCCAGAACAGCACCGAGACCTGCTACGGCAGCGAGGCCGACCAGTGTGAGGCCTGCACCCACTACAAGGACCCCCCC

TTCTGCGTGGCCAGATGCCCTAGCGGCGTGAAGCCCGACCTGAGCTACATGCCCATCTGGAAGTTCCCCGACGAGGAA

GGCGCCTGCCAGCCCTGCCCCATCAACTGCACCCACAGCTGCGCCGACCTGGACGATAGAGGCTGCCCTGCCGAG

SEQ ID NO: 14: Amino Acid Sequence of ECD-derived Peptide 2 (ECD2)

<u>MASELAALCRWGLLLALLPPGAAS</u>TQVCTGTDMKLRLPASPETHLDMLRHLYQGCQVVQGNLELTYLPTNASLSFLQD

IQEVQGYVLIAHNQVRQVPLQRLRIVRGTQLFEDNYALAVLDNGDPLDSVAPAAGATPGGLQELQLRSLTEILKGGVL

IRRSPQLCHQDTVLWEDVFRKNNQLALVLMDTNRSRACHPCAPMCKANHCWGESSQDCQTLTRTICTSACARCKAPLP

TABLE 5-continued

Raw Sequence Listing
(Signal sequence underlined)

TDCCHEQCAAGCTGPKHSDCLACLHFNHSGICELHCPALVTYNTDTFESMPNPEGRYTFGASCVTACPYNYLSTDVGS

CTLVCPLHNQEVTAEDGTQRCEKCSKPCARVCYGLGMEHLREARAITSANVQDFVGCKKIFGSLAFLPESFDGDPASG

TAPLQPEQLQVFETLEEITGYLYISAWPDSFPNLSVFQNLRVIRGRILHNGAYSLTLQGLGISWLGLRSLQELGSGLA

LVHRNARLCFVHTVPWDQLFRNPHQALLHSGNRPEEDCVGEGFVCYSLCAHGHCWGPGPTQCVNCSHFLRGQECVEEC

RVLQGLPREYVNARHCLPCHPECQPQNGSVTCFGPEADQCVACAHYKDPPFCVARCPSGVKPDLSYMPIWKFPDEEGA

CQPCPINCTHSCVDLDDKGCPAE

SEQ ID NO: 15: DNA Sequence Encoding the Amino Acid Sequence of
ECD-derived Peptide 2 (ECD2) of SEQ ID NO: 14

ATGGCTAGCGAGCTGGCCGCCCTGTGTAGATGGGGACTGCTGCTGGCTCTGCTGCCTCCTGGAGCCGCTTCTACACAG

GTCTGCACCGGCACCGACATGAAGCTGAGACTGCCCGCCAGCCCCGAGACACACCTGGACATGCTGCGGCACCTGTAC

CAGGGCTGCCAGGTGGTCCAGGGGAATCTGGAACTGACCTACCTGCCCACCAACGCCAGCCTGAGCTTCCTGCAGGAC

ATCCAGGAAGTGCAGGGCTACGTCCTGATCGCCCACAACCAGGTCCGCCAGGTGCCCCTGCAGCGGCTGAGAATCGTG

CGGGGCACCCAGCTGTTCGAGGACAACTACGCCCTGGCCGTGCTGGACAACGGCGACCCTCTGGATAGCGTGGCCCCT

GCTGCTGGGGCTACACCTGGCGGACTGCAGGAACTGCAGCTGCGGAGCCTGACCGAGATCCTGAAGGGCGGCGTGCTG

ATCAGGCGGAGCCCTCAGCTGTGCCACCAGGACACCGTGCTGTGGGAGGACGTGTTCCGGAAGAACAACCAGCTGGCC

CTCGTGCTGATGGACACCAACAGAAGCCGGGCCTGCCACCCCTGCGCCCCCATGTGCAAGGCCAATCACTGCTGGGGA

GAGAGCAGCCAGGACTGCCAGACCCTGACCCGGACCATCTGCACCAGCGCCTGCGCCAGATGCAAGGCCCCCCTGCCT

ACCGACTGCTGCCACGAACAGTGCGCCGCTGGCTGCACCGGCCCCAAGCACAGCGATTGCCTGGCCTGCCTGCACTTC

AACCACAGCGGCATCTGCGAGCTGCACTGCCCCTGCCCTGGTGACATACAACACCGACACCTTCGAGAGCATGCCCAAC

CCCGAGGGCCGGTACACCTTCGGCGCCAGCTGTGTGACCGCCTGCCCCTACAACTACCTGAGCACCGACGTGGGCAGC

TGCACCCTGGTGTGCCCCCTGCACAACCAGGAAGTGACCGCCGAGGACGGCACCCAGAGATGCGAGAAGTGCAGCAAG

CCTTGCGCCAGAGTGTGCTACGGCCTGGGCATGGAACACCTGAGAGAGGCCAGAGCCATCACCAGCGCCAACGTGCAG

GACTTCGTGGGCTGCAAGAAGATTTTCGGCTCCCTGGCCTTCCTGCCCGAGAGCTTCGACGGCGATCCTGCCTCTGGC

ACCGCCCCTCTGCAGCCTGAGCAGCTGCAGGTCTTCGAGACACTGGAAGAGATCACCGGCTACCTGTACATCAGCGCC

TGGCCCGACAGCTTCCCCAACCTGAGCGTGTTCCAGAACCTGAGAGTGATCCGGGGCAGAATCCTGCACAACGGCGCC

TACAGCCTGACCCTGCAGGGCCTGGGAATCAGCTGGCTGGGCCTGCGGAGCCTGCAGGAACTGGGATCTGGCCTGGCT

CTGGTGCACCGGAACGCCCGGCTGTGCTTCGTGCACACCGTGCCCTGGGACCAGCTGTTCAGAAACCCCCACCAGGCT

CTGCTGCACAGCGGCAACCGGCCCGAAGAGGATTGCGTGGGCGAGGGCTTCGTGTGCTACTCCCTGTGCGCCCACGGC

CACTGTTGGGGACCTGGCCCTACCCAGTGCGTGAACTGCAGCCACTTCCTGCGGGGCCAAGAATGCGTGGAAGAGTGC

CGGGTGCTGCAGGGACTGCCCCGGGAATACGTGAACGCCAGACACTGCCTGCCTTGCCACCCCGAGTGCCAGCCCCAG

AATGGCAGCGTGACCTGCTTCGGACCCGAGGCCGATCAGTGTGTGGCCTGCGCCCACTACAAGGACCCCCCATTCTGC

GTGGCCAGATGCCCCAGCGGCGTGAAGCCCGACCTGAGCTACATGCCCATCTGGAAGTTCCCCGACGAGGAAGGCGCC

TGCCAGCCTTGCCCCATCAACTGCACCCACAGCTGCGTGGACCTGGACGACAAGGGCTGCCCTGCCGAG

SEQ ID NO: 16: Amino Acid Sequence of TMD-derived Peptide 2 (TMD2)

QRASPLTSIISAVVGILLVVVLGVVFGILIKRRQQKIRKYTMRR

SEQ ID NO: 17: DNA Sequence Encoding Amino Acid Sequence of TMD-
derived Peptide 2 (TMD2) of SEQ ID NO: 16

CAGAGAGCCAGCCCCCTGACCAGCATCATCAGCGCCGTGGTGGGAATCCTGCTGGTGGTGGTGCTGGGCGTGGTGTTC

GGCATCCTGATCAAGCGGCGGCAGCAGAAGATCCGGAAGTACACCATGCGGCGG

TABLE 5-continued

Raw Sequence Listing
(Signal sequence underlined)

SEQ ID NO: 18: Amino Acid Sequence of a Peptide Composed of ECD2 and CTD2

<u>MASELAALCRWGLLLALLPPGAAS</u>TQVCTGTDMKLRLPASPETHLDMLRHLYQGCQVVQGNLELTYLPTNASLSFLQD
IQEVQGYVLIAHNQVRQVPLQRLRIVRGTQLFEDNYALAVLDNGDPLDSVAPAAGATPGGLQELQLRSLTEILKGGVL
IRRSPQLCHQDTVLWEDVFRKNNQLALVLMDTNRSRACHPCAPMCKANHCWGESSQDCQTLTRTICTSACARCKAPLP
TDCCHEQCAAGCTGPKHSDCLACLHFNHSGICELHCPALVTYNTDTFESMPNPEGRYTFGASCVTACPYNYLSTDVGS
CTLVCPLHNQEVTAEDGTQRCEKCSKPCARVCYGLGMEHLREARAITSANVQDFVGCKKIFGSLAFLPESFDGDPASG
TAPLQPEQLQVFETLEEITGYLYISAWPDSFPNLSVFQNLRVIRGRILHNGAYSLTLQGLGISWLGLRSLQELGSGLA
LVHRNARLCFVHTVPWDQLFRNPHQALLHSGNRPEEDCVGEGFVCYSLCAHGHCWGPGPTQCVNCSHFLRGQECVEEC
RVLQGLPREYVNARHCLPCHPECQPQNGSVTCFGPEADQCVACAHYKDPPFCVARCPSGVKPDLSYMPIWKFPDEEGA
CQPCPINCTHSCVDLDDKGCPAENEDLGPSSPMDSTFYRSLLEDEDMGELVDAEEYLVPQQGFFCPDPTPGTGSTAHR
RHRSSSARNGGGDLTLGMEPSGEGPPRSPRAPSEGTGSDVFDGDLAVGVTKGLQSLSPQDLSPLQRYSEDPTLPLPSE
TDGKVAPLSCSPQPEFVNQSDVQPKSPLTPEGPPSPARPTGATLERAKTLSPGKNGVVKDVFTFGGAVENPEFLAPRE
GTASPPHPSPAFSPAFDNLFFWDQNSSEQGPPPSNFEGTPTAENPEFLGLDVPV

SEQ ID NO: 19: DNA Sequence Encoding the Amino Acid Sequence of SEQ ID NO: 18

ATGGCTAGCGAGCTGGCCGCCCTGTGTAGATGGGGACTGCTGCTGGCTCTGCTGCCTCCTGGAGCCGCTTCTACACAG
GTCTGCACCGGCACCGACATGAAGCTGAGACTGCCCGCCAGCCCCGAGACACACCTGGACATGCTGCGGCACCTGTAC
CAGGGCTGCCAGGTGGTCCAGGGGAATCTGGAACTGACCTACCTGCCCACCAACGCCAGCCTGAGCTTCCTGCAGGAC
ATCCAGGAAGTGCAGGGCTACGTCCTGATCGCCCACAACCAGGTCCGCCAGGTGCCCCTGCAGCGGCTGAGAATCGTG
CGGGGCACCCAGCTGTTCGAGGACAACTACGCCCTGGCCGTGCTGGACAACGGCGACCCTCTGGATAGCGTGGCCCCT
GCTGCTGGGGCTACACCTGGCGGACTGCAGGAACTGCAGCTGCGGAGCCTGACCGAGATCCTGAAGGGCGGCGTGCTG
ATCAGGCGGAGCCCTCAGCTGTGCCACCAGGACACCGTGCTGTGGGAGGACGTGTTCCGGAAGAACAACCAGCTGGCC
CTCGTGCTGATGGACACCAACAGAAGCCGGGCCTGCCACCCCTGCGCCCCCATGTGCAAGGCCAATCACTGCTGGGGA
GAGAGCAGCCAGGACTGCCAGACCCTGACCCGGACCATCTGCACCAGCGCCTGCGCCAGATGCAAGGCCCCCCTGCCT
ACCGACTGCTGCCACGAACAGTGCGCCGCTGGCTGCACCGGCCCAAGCACAGCGATTGCCTGGCCTGCCTGCACTTC
AACCACAGCGGCATCTGCGAGCTGCACTGCCCTGCCCTGGTGACATACAACACCGACACCTTCGAGAGCATGCCCAAC
CCCGAGGGCCGGTACACCTTCGGCGCCAGCTGTGTGACCGCCTGCCCCTACAACTACCTGAGCACCGACGTGGGCAGC
TGCACCCTGGTGTGCCCCCTGCACAACCAGGAAGTGACCGCCGAGGACGGCACCCAGAGATGCGAGAAGTGCAGCAAG
CCTTGCGCCAGAGTGTGCTACGGCCTGGGCATGGAACACCTGAGAGAGGCCAGAGCCATCACCAGCGCCAACGTGCAG
GACTTCGTGGGCTGCAAGAAGATTTTCGGCTCCCTGGCCTTCCTGCCCGAGAGCTTCGACGGCGATCCTGCCTCTGGC
ACCGCCCCTCTGCAGCCTGAGCAGCTGCAGGTCTTCGAGACACTGGAAGAGATCACCGGCTACCTGTACATCAGCGCC
TGGCCCGACAGCTTCCCCAACCTGAGCGTGTTCCAGAACCTGAGAGTGATCCGGGGCAGAATCCTGCACAACGGCGCC
TACAGCCTGACCCTGCAGGGCCTGGGAATCAGCTGGCTGGGCCTGCGGAGCCTGCAGGAACTGGGATCTGGCCTGGCT
CTGGTGCACCGGAACGCCCGGCTGTGCTTCGTGCACACCGTGCCCTGGGACCAGCTGTTCAGAAACCCCCACCAGGCT
CTGCTGCACAGCGGCAACCGGCCCGAAGAGGATTGCGTGGGCGAGGGCTTCGTGTGCTACTCCCTGTGCGCCCACGGC
CACTGTTGGGGACCTGGCCCTACCCAGTGCGTGAACTGCAGCCACTTCCTGCGGGGCCAAGAATGCGTGGAAGAGTGC
CGGGTGCTGCAGGGACTGCCCCGGGAATACGTGAACGCCAGACACTGCCTGCCTTGCCACCCCGAGTGCCAGCCCCAG
AATGGCAGCGTGACCTGCTTCGGACCCGAGGCCGATCAGTGTGTGGCCTGCGCCCACTACAAGGACCCCCCATTCTGC
GTGGCCAGATGCCCCAGCGGCGTGAAGCCCGACCTGAGCTACATGCCCATCTGGAAGTTCCCCGACGAGGAAGGCGCC

TABLE 5-continued

Raw Sequence Listing
(Signal sequence underlined)

TGCCAGCCTTGCCCCATCAACTGCACCCACAGCTGCGTGGACCTGGACGACAAGGGCTGCCCTGCCGAGAACGAGGAC
CTGGGCCCCTCTAGCCCCATGGACAGCACCTTCTACCGGTCCCTGCTGGAAGATGAGGACATGGGCGAGCTGGTGGAC
GCCGAGGAATACCTGGTGCCTCAGCAGGGCTTCTTCTGCCCCGACCCTACCCCTGGCACCGGCTCTACCGCCCACAGA
CGGCACAGAAGCAGCAGCGCCAGAAACGGCGGAGGCGACCTGACCCTGGGAATGGAACCTAGCGGCGAGGGACCTCCC
AGAAGCCCTAGAGCCCCTAGCGAGGGCACCGGCAGCGACGTGTTCGATGGCGATCTGGCCGTGGGCGTGACCAAGGGA
CTGCAGAGCCTGAGCCCCCAGGACCTGTCCCCCCTGCAGAGATACAGCGAGGACCCCACCCTGCCCCTGCCCAGCGAG
ACAGATGGCAAGGTGGCCCCCCTGAGCTGCAGCCCTCAGCCCGAGTTCGTGAACCAGAGCGACGTGCAGCCCAAGTCC
CCCCTGACACCCGAGGGACCTCCAAGCCCTGCCAGACCTACCGGCGCCACCCTGGAAAGAGCCAAGACCCTGAGCCCC
GGCAAGAACGGCGTGGTGAAAGACGTGTTCACCTTCGGAGGCGCCGTGGAAAACCCCGAGTTCCTGGCCCCCAGAGAG
GGCACAGCCAGCCCTCCACACCCCAGCCCAGCCTTCTCCCCCGCCTTCGACAACCTGTTCTTCTGGGACCAGAACAGC
AGCGAGCAGGGCCCACCCCCCAGCAATTTCGAGGGCACCCCCACCGCCGAGAATCCTGAGTTCCTGGGCCTGGACGTG
CCCGTGTGA

SEQ ID NO: 20: Amino Acid Sequence of RaDHER2-2

<u>MASELAALCRWGLLLALLPPGAAS</u>TQVCTGTDMKLRLPASPETHLDMLRHLYQGCQVVQGNLELTYLPTNASLSFLQD
IQEVQGYVLIAHNQVRQVPLQRLRIVRGTQLFEDNYALAVLDNGDPLDSVAPAAGATPGGLQELQLRSLTEILKGGVL
IRRSPQLCHQDTVLWEDVFRKNNQLALVLMDTNRSRACHPCAPMCKANHCWGESSQDCQTLTRTICTSACARCKAPLP
TDCCHEQCAAGCTGPKHSDCLACLHFNHSGICELHCPALVTYNTDTFESMPNPEGRYTFGASCVTACPYNYLSTDVGS
CTLVCPLHNQEVTAEDGTQRCEKCSKPCARVCYGLGMEHLREARAITSANVQDFVGCKKIFGSLAFLPESFDGDPASG
TAPLQPEQLQVFETLEEITGYLYISAWPDSFPNLSVFQNLRVIRGRILHNGAYSLTLQGLGISWLGLRSLQELGSGLA
LVHRNARLCFVHTVPWDQLFRNPHQALLHSGNRPEEDCVGEGFVCYSLCAHGHCWGPGPTQCVNCSHFLRGQECVEEC
RVLQGLPREYVNARHCLPCHPECQPQNGSVTCFGPEADQCVACAHYKDPPFCVARCPSGVKPDLSYMPIWKFPDEEGA
CQPCPINCTHSCVDLDDKGCPAEQRASPLTSIISAVVGILLVVVLGVVFGILIKRRQQKIRKYTMRRNEDLGPSSPMD
STFYRSLLEDEDMGELVDAEEYLVPQQGFFCPDPTPGTGSTAHRRHRSSSARNGGGDLTLGMEPSGEGPPRSPRAPSE
GTGSDVFDGDLAVGVTKGLQSLSPQDLSPLQRYSEDPTLPLPSETDGKVAPLSCSPQPEFVNQSDVQPKSPLTPEGPP
SPARPTGATLERAKTLSPGKNGVVKDVFTFGGAVENPEFLAPREGTASPPHPSPAFSPAFDNLFFWDQNSSEQGPPPS
NFEGTPTAENPEFLGLDVPV

SEQ ID NO: 21: DNA Sequence Encoding the Amino Acid Sequence of
RaDHER2-2 of SEQ ID NO: 20

ATGGCTAGCGAGCTGGCCGCCCTGTGTAGATGGGGACTGCTGCTGGCTCTGCTGCCTCCTGGAGCCGCTTCTACACAG
GTCTGCACCGGCACCGACATGAAGCTGAGACTGCCCGCCAGCCCCGAGACACACCTGGACATGCTGCGGCACCTGTAC
CAGGGCTGCCAGGTGGTCCAGGGGAATCTGGAACTGACCTACCTGCCCACCAACGCCAGCCTGAGCTTCCTGCAGGAC
ATCCAGGAAGTGCAGGGCTACGTCCTGATCGCCCACAACCAGGTCCGCCAGGTGCCCCTGCAGCGGCTGAGAATCGTG
CGGGGCACCCAGCTGTTCGAGGACAACTACGCCCTGGCCGTGCTGGACAACGGCGACCCTCTGGATAGCGTGGCCCCT
GCTGCTGGGGCTACACCTGGCGGACTGCAGGAACTGCAGCTGCGGAGCCTGACCGAGATCCTGAAGGGCGGCGTGCTG
ATCAGGCGGAGCCCTCAGCTGTGCCACCAGGACACCGTGCTGTGGGAGGACGTGTTCCGGAAGAACAACCAGCTGGCC
CTCGTGCTGATGGACACCAACAGAAGCCGGGCCTGCCACCCCTGCGCCCCCATGTGCAAGGCCAATCACTGCTGGGGA
GAGAGCAGCCAGGACTGCCAGACCCTGACCCGGACCATCTGCACCAGCGCCTGCGCCAGATGCAAGGCCCCCCTGCCT
ACCGACTGCTGCCACGAACAGTGCGCCGCTGGCTGCACCGGCCCCAAGCACAGCGATTGCCTGGCCTGCCTGCACTTC
AACCACAGCGGCATCTGCGAGCTGCACTGCCCTGCCCTGGTGACATACAACACCGACACCTTCGAGAGCATGCCCAAC

TABLE 5-continued

Raw Sequence Listing
(Signal sequence underlined)

CCCGAGGGCCGGTACACCTTCGGCGCCAGCTGTGTGACCGCCTGCCCCTACAACTACCTGAGCACCGACGTGGGCAGC

TGCACCCTGGTGTGCCCCCTGCACAACCAGGAAGTGACCGCCGAGGACGGCACCCAGAGATGCGAGAAGTGCAGCAAG

CCTTGCGCCAGAGTGTGCTACGGCCTGGGCATGGAACACCTGAGAGAGGCCAGAGCCATCACCAGCGCCAACGTGCAG

GACTTCGTGGGCTGCAAGAAGATTTTCGGCTCCCTGGCCTTCCTGCCCGAGAGCTTCGACGGCGATCCTGCCTCTGGC

ACCGCCCCTCTGCAGCCTGAGCAGCTGCAGGTCTTCGAGACACTGGAAGAGATCACCGGCTACCTGTACATCAGCGCC

TGGCCCGACAGCTTCCCCAACCTGAGCGTGTTCCAGAACCTGAGAGTGATCCGGGGCAGAATCCTGCACAACGGCGCC

TACAGCCTGACCCTGCAGGGCCTGGGAATCAGCTGGCTGGGCCTGCGGAGCCTGCAGGAACTGGGATCTGGCCTGGCT

CTGGTGCACCGGAACGCCCGGCTGTGCTTCGTGCACACCGTGCCCTGGGACCAGCTGTTCAGAAACCCCCACCAGGCT

CTGCTGCACAGCGGCAACCGGCCCGAAGAGGATTGCGTGGGCGAGGGCTTCGTGTGCTACTCCCTGTGCGCCCACGGC

CACTGTTGGGGACCTGGCCCTACCCAGTGCGTGAACTGCAGCCACTTCCTGCGGGGCCAAGAATGCGTGGAAGAGTGC

CGGGTGCTGCAGGGACTGCCCCGGGAATACGTGAACGCCAGACACTGCCTGCCTTGCCACCCCGAGTGCCAGCCCCAG

AATGGCAGCGTGACCTGCTTCGGACCCGAGGCCGATCAGTGTGTGGCCTGCGCCCACTACAAGGACCCCCCATTCTGC

GTGGCCAGATGCCCCAGCGGCGTGAAGCCCGACCTGAGCTACATGCCCATCTGGAAGTTCCCCGACGAGGAAGGCGCC

TGCCAGCCTTGCCCCATCAACTGCACCCACAGCTGCGTGGACCTGGACGACAAGGGCTGCCCTGCCGAGCAGAGAGCC

AGCCCCCTGACCAGCATCATCAGCGCCGTGGTGGGAATCCTGCTGGTGGTGGTGCTGGGCGTGGTGTTCGGCATCCTG

ATCAAGCGGCGGCAGCAGAAGATCCGGAAGTACACCATGCGGCGGAACGAGGACCTGGGCCCCTCTAGCCCCATGGAC

AGCACCTTCTACCGGTCCCTGCTGGAAGATGAGGACATGGGCGAGCTGGTGGACGCCGAGGAATACCTGGTGCCTCAG

CAGGGCTTCTTCTGCCCCGACCCTACCCCTGGCACCGGCTCTACCGCCCACAGACGGCACAGAAGCAGCAGCGCCAGA

AACGGCGGAGGCGACCTGACCCTGGGAATGGAACCTAGCGGCGAGGGACCTCCCAGAAGCCCTAGAGCCCCTAGCGAG

GGCACCGGCAGCGACGTGTTCGATGGCGATCTGGCCGTGGGCGTGACCAAGGGACTGCAGAGCCTGAGCCCCCAGGAC

CTGTCCCCCTGCAGAGATACAGCGAGGACCCCACCCTGCCCCTGCCCAGCGAGACAGATGGCAAGGTGGCCCCCCTG

AGCTGCAGCCCTCAGCCCGAGTTCGTGAACCAGAGCGACGTGCAGCCCAAGTCCCCCCTGACACCCGAGGGACCTCCA

AGCCCTGCCAGACCTACCGGCGCCACCCTGGAAAGAGCCAAGACCCTGAGCCCCGGCAAGAACGGCGTGGTGAAAGAC

GTGTTCACCTTCGGAGGCGCCGTGGAAAACCCCGAGTTCCTGGCCCCAGAGAGGGCACAGCCAGCCCTCCACACCCC

AGCCCAGCCTTCTCCCCCGCCTTCGACAACCTGTTCTTCTGGGACCAGAACAGCAGCGAGCAGGGCCCACCCCCCAGC

AATTTCGAGGGCACCCCCACCGCCGAGAATCCTGAGTTCCTGGGCCTGGACGTGCCCGTGTGA

SEQ ID NO: 22: Amino Acid Sequence of CTD-derived Peptide 2 (CTD2)

NEDLGPSSPMDSTFYRSLLEDEDMGELVDAEEYLVPQQGFFCPDPTPGTGSTAHRRHRSSSARNGGGDLTLGMEPSGE

GPPRSPRAPSEGTGSDVFDGDLAVGVTKGLQSLSPQDLSPLQRYSEDPTLPLPSETDGKVAPLSCSPQPEFVNQSDVQ

PKSPLTPEGPPSPARPTGATLERAKTLSPGKNGVVKDVFTFGGAVENPEFLAPREGTASPPHPSPAFSPAFDNLFFWD

QNSSEQGPPPSNFEGTPTAENPEFLGLDVPV

SEQ ID NO: 23: DNA Sequence Encoding the Amino Acid Sequence of
CTD-derived Peptide 2 (CTD2) of SEQ ID NO: 22

AACGAGGACCTGGGCCCCTCTAGCCCCATGGACAGCACCTTCTACCGGTCCCTGCTGGAAGATGAGGACATGGGCGAG

CTGGTGGACGCCGAGGAATACCTGGTGCCTCAGCAGGGCTTCTTCTGCCCCGACCCTACCCCTGGCACCGGCTCTACC

GCCCACAGACGGCACAGAAGCAGCAGCGCCAGAAACGGCGGAGGCGACCTGACCCTGGGAATGGAACCTAGCGGCGAG

GGACCTCCCAGAAGCCCTAGAGCCCCTAGCGAGGGCACCGGCAGCGACGTGTTCGATGGCGATCTGGCCGTGGGCGTG

ACCAAGGGACTGCAGAGCCTGAGCCCCCAGGACCTGTCCCCCCTGCAGAGATACAGCGAGGACCCCACCCTGCCCCTG

CCCAGCGAGACAGATGGCAAGGTGGCCCCCCTGAGCTGCAGCCCTCAGCCCGAGTTCGTGAACCAGAGCGACGTGCAG

TABLE 5-continued

Raw Sequence Listing
(Signal sequence underlined)

CCCAAGTCCCCCCTGACACCCGAGGGACCTCCAAGCCCTGCCAGACCTACCGGCGCCACCCTGGAAAGAGCCAAGACC

CTGAGCCCCGGCAAGAACGGCGTGGTGAAAGACGTGTTCACCTTCGGAGGCGCCGTGGAAAACCCCGAGTTCCTGGCC

CCCAGAGAGGGCACAGCCAGCCCTCCACACCCCAGCCCAGCCTTCTCCCCCGCCTTCGACAACCTGTTCTTCTGGGAC

CAGAACAGCAGCGAGCAGGGCCCACCCCCCAGCAATTTCGAGGGCACCCCCACCGCCGAGAATCCTGAGTTCCTGGGC

CTGGACGTGCCCGTGTGA

SEQ ID NO: 24: DNA Sequence Encoding the Amino Acid Sequence of
TMD-derived Peptide 1 (TMD1) of SEQ ID NO: 11

CAGAGAGCCAGCCCCCTGACCAGCATCATCAGCGCCGTGGTGGGAATCCTGCTGGTGGTGGTGCTGGGCGTGGTGTTC

GGCATCCTGATC

G. Examples

The following examples are provided to illustrate certain embodiments of the invention. They should not be construed to limit the scope of the invention in any way. From the above discussion and these examples, one skilled in the art can ascertain the essential characteristics of this invention, and without departing from the spirit and scope thereof, can make various changes and modifications of the invention to adapt it to various usage and conditions.

Example 1

Design of Immunogenic HER-2 Peptides

1). RaDHER2-1

The Immunogenic HER-2 peptide RaDHER2-1 comprises an ECD-derived peptide joined to a CTD-derived peptide. The amino acid sequence of RaDHER2-1 is set forth in SEQ ID No: 3. SEQ ID NO:3 also includes the amino acid sequence of the signal sequence (amino acid residues 1-22). RaDHER2-1 was designed by aligning the human HER-2 protein sequence with the orthologous sequences of rhesus monkey, horse, dog, cat, rat, and mouse using ClustalW and introducing certain point mutations into human HER2 extracellular domain (ECD) and cytoplasmic domain (CTD) based on amino acid substitutions observed in the orthologs. One or more amino acids were selected from each of the six orthologous sequences indicated above. These substitutions were selected in positions outside of the conserved T cell epitope sequences identified in the application above and outside of the signal sequence. This resulted in 126 point mutations in the 645 amino acids of the ECD domain. Likewise, point substitutions were produced in the CT domain, along with several tyrosine to phenylalanine mutations (to avoid phosphorylation in the modified CT sequence due to safety consideration), resulting in 62 mutations out of 265 amino acid residues. The final designed HER-2 peptide, which is referred to as "RaDHER2-1" in this application, consists of the modified ECD domain containing 126 point mutations fused to the modified CT domain containing 62 point mutations. For expressing the full RaDHER2-1 sequence, the DNA sequences that encode the ECD-derived peptide and the CTD-derived peptide sequences described above were fused to form a single transcript and cloned into suitable vectors. In addition, codons for a restriction enzyme site (amino acid residues alanine and serine) were inserted into the RaD-HER2-1 DNA sequence between amino acid residues 1 (methionine) and 2 of the RaDHER2-1 peptide. The RaDHER2-1 DNA sequence containing the restriction enzyme site was used in the experiments described below.

2) RaDHER2-2

The Immunogenic HER-2 peptide RaDHER2-2 is a fusion protein that comprises an ECD-derived peptide, a TMD-derived peptide, and a CTD-derived peptide. The amino acid sequence of RaDHER2-1 is set forth in SEQ ID No: 20. In addition, SEQ ID NO: 20 includes the amino acid sequence of the signal sequence (amino acid residues 1-24). The signal sequence further includes a restriction enzyme site (amino acid residues alanine at position 2 and serine at position 3). In the design of RaDHER2-2, in addition to the HER-2 sequences of rhesus monkey, horse, dog, cat, rat, and mouse, the orthologous sequences of chimp, hamster, and opossum were also aligned with the human HER-2 protein, The ECD-derived peptide of contains 52 amino acid substitutions. The selection of amino acid substitutions is based on the same principle as for the design of RadHER2-1. The CTD-derived peptide includes one additional amino acid change from the CTD-derived peptide of RaDHER2-1.

Example 2

Cloning, Expression and PMED Formulations of RaDHER2-1 and RadHER2-2

2a. Cloning of RaDHER2-1 and RadHER2-2 into PJV7563 Vector:

The immunogenic HER-2 peptide amino acid sequence was codon optimized for optimal expression in mammalian cells and cloned into a vector (PJV7563) that was suitable for in vivo testing in animals (FIG. 1). Both strands of the RaDHER2 DNA in the PJV7563 vector were completely sequenced to confirm the designed sequence.

2b. Plasmid DNA Production:

A large scale plasmid DNA (Qiagen/CsCl) was produced from a sequence confirmed clone. The quality of the plasmid DNA was confirmed by high 260/280 ratio, high super coiled/nicked DNA ratio, low endotoxin levels (<10 U/mg DNA) and negative bio burden.

2c. Expression of the RaDHER2-1 and RadHER2-2 Construct in Mammalian Cells:

The protein expression of RaDHER2 was determined by Western blot analysis of cell extracts from 293FS cells expressing HER-2 peptide by Lipofectamine 2000 mediated transient transfection with PJV7563 vector containing the RaDHER2 as described by the manufacturer (Invitrogen). Five days after the transfection both the media and the cells were harvested for expression analysis by Western. Commercially available anti-HER2 antibody (Thermo Scientific, clone 3B5) was used for the detection of HER-2 peptide. The expression of HER-2 peptide was detected in both the media and the cell lysate, indicating that RaDHER2 protein was expressed.

2d. Formulations of RaDHER2-1 and RadHER2-2 (Gold Particles, and ND10):

Particle Mediated Epidermal Delivery technology (PMED), is a needle-free method of administering vaccines to animals or to patients. The PMED system involves the precipitation of DNA onto microscopic gold particles that are then propelled by helium gas into the epidermis. The DNA-coated gold particles are delivered into the antigen-presenting cells (APCs) of the epidermis, and once inside the nuclei of the APCs, the DNA elutes off the gold and becomes transcriptionally active, producing encoded protein. This protein is then presented by the APCs to the lymphocytes to induce a T-cell-mediated immune response. The ND10 delivery device uses pressurized helium from an internal cylinder to accelerate gold particles of 1-3 μm diameter coated with DNA into the epidermis. ND10 devices used in in vivo studies were formulated to contain 2 μg of the HER-2 NDA per 1 mg of gold particles. Control plasmids were also formulated similarly for PMED vaccination (Sharpe, M. Lynch, D. Topham, S. Major, D. Wood, J and Loudon, P. Protection of mice from H5N1 influenza challenge by prophylactic DNA vaccination using particle mediated epidermal delivery. Vaccine, 2007, 25(34): 6392-98: Roberts L K, Barr L J, Fuller D H, McMahon C W, Leese P T, Jones S. Clinical safety and efficacy of a powdered Hepatitis B nucleic acid vaccine delivered to the epidermis by a commercial prototype device. Vaccine, 2005; 23(40):4867-78.).

2e. PMED Vaccination:

Eight to ten weeks old mice were immunized with PMED control or HER2 containing antigen in a prime/boost format and the immune response was measured 7 days after the last boost in the splenocytes of mice unless otherwise indicated.

Example 3

Immunogenicity Studies with RaDHER2-1 and RadHER2-2

The immunogenicity of RaDHER2-1 and RadHER2-2 evaluated in different in vivo and in vitro models: (a) Balb/c mice for breaking T cell tolerance (b) HLA.A2 transgenic mice and (c) in vitro human PBMC assay for the processing and presentation of the HER-2 in the HLA-A2 context. Amino acid sequences of certain peptides that were used in the studies are provided below:

```
                           (SEQ ID NO: 25)
HBVc Kd/C, p87:      SYVNTNMGL (SEQ ID NO: 26)
Rat HER2, p66:       TYVPANASL (SEQ ID NO: 27)
Rat HER2, p169:      DMVLWKDVFRKNNQL (SEQ ID NO: 28)
MouseHER2, p63:      TYLPANASL (SEQ ID NO: 29)
hHBV, p18:           FLPSDFFPSV (SEQ ID NO: 30)
Human HER2, p5:      ALCRWGLL (SEQ ID NO: 31)
Human HER2, p48:     HLYQGCQVV (SEQ ID NO: 32)
Human HER2, p98:     RLRIVRGTQLFEDNYAL (SEQ ID NO: 33)
Human HER2, p106:    QLFEDNYAL (SEQ ID NO: 34)
Human HER2, p369:    KIFGSLAFL (SEQ ID NO: 35)
Human HER2, p435:    ILHNGAYSL
```

3a. Immunogenicity Studies in BALB/c Mice:

BALB/c mice were vaccinated twice in a two week interval with RaDHER2-1 DNA formulated (2 μg plasmid DNA/immunization) for PMED and the T cell immune response was measured 7 days after the last immunization by IFNγ ELISPOT assay. Human HER2 and rat HER2 vaccines were included as controls. The frequency of antigen specific IFN-γ secreting T cells in the spleen was assessed against H-2d restricted targets cells (P815) that were either pulsed with rat HER2 peptides or an irrelevant peptide (derived from HBVc antigen) and TUBO cells that endogenously express rat HER2 antigen. Specific T cell responses to rat and mouse HER2 peptide pulsed target cells and TUBO cells were observed in mice immunized with rat, RaDHER2 and human HER2 antigens but not to P815 cells pulsed with irrelevant HBVc peptide. Results are presented in Table 1. Data plot is normalized to the number of cells that secrete IFNγ in 1e6 splenocytes.

TABLE 1

Tolerance to self HER-2 antigen is broken in BALB/c mice vaccinated with xenogeneic HER2 vaccines.

| Peptide pulsed targets and | IFNγ SFC/1e6 splenocytes | | |
|---|---|---|---|
| rat HER-2+ tumor cells | Rat HER2 | Human HER2 | RaDHER2-1 |
| Splenocyte only | 1 (1) | 5 (6) | 2 (2) |
| HBVc Kd/C87-95 | 2 (2) | 2 (2) | 3 (1) |
| Rat HER-2 p66 | 829 (3) | 55 (4) | 831 (26) |
| Rat HER-2 p65 | 32 (8) | 5 (3) | 9 (1) |
| Rat HER-2 p169 | 106 (10) | 194 (26) | 11 (1) |
| Rat HER-2 p393 | 160 (15) | 14 (4) | 87 (11) |
| Rat HER-2 p624 | 449 (47) | 10 (2) | 439 (31) |
| Mouse HER-2 p63 | 243 (16) | 57 (12) | 133 (30) |
| TUBO | 291 (29) | 8 (6) | 389 (70) |

( ) = SD

All three xenogeneic vaccines, rat HER2, human HER2 and RaDHER2-1 vaccines induces specific T responses to both rat and mouse HER2 peptides. The results indicate that RaDHER2-1, as well as the rat and human HER2 antigens, broke immune tolerance to mouse HER2 as demonstrated by the recognition of target cells pulsed with mouse HER2 p63 peptide.

3b. Immunogenicity Studies in HLA A2/DR1 Mice:

A human HLA transgenic model was used to evaluate the processing and presentation of the RaDHER2-1 and RaDHER2-2 peptide. The model is the HLA A2/DR1 mice from the Pasteur Institute (Paris, France), HLA A2/DR mice are KO for murine β-2-microglobulin and do not express functional H-2b molecules; therefore this model would represent the processing and presentation of antigen in the human MHC I system (Pajot, A., M.-L. Michel, N. Faxilleau, V. Pancre, C. Auriault, D. M. Ojcius, F. A. Lemonnier, and Y.-C. Lone. A mouse model of human adaptive immune functions: HLA-A2.1-/HLA-DR1-transgenic H-2 class I-/class II-knockout mice. Eur. J. Immunol. 2004, 34:3060-69.). HLA A2/DR1 mice were immunized 3 times (two weeks apart) by PMED (gene gun) and the T cell response was measured 7 days after the last immunization by determining interferon-gamma (IFNγ) release by ELISPOT assay. Results for RaDHER2-1 are shown in Tables 2 and 3. Data plot is normalized to the number of cells that secrete IFNγ in 1e6 splenocytes.

TABLE 2

RaDHER2-1 vaccine induced T cell responses

| Peptide pulsed targets and | IFNγ SFC/1e6 splenocytes | |
|---|---|---|
| human HER-2+ tumor cells | Human HER2 | RaDHER2-1 |
| HBV p18 | 0 (0) | 5 (5) |
| HER-2 p5 | 38 (9) | 358 (23) |
| HER-2 p106 | 1148 (22) | 770 (11) |
| HER-2 p98 | 1176 (56) | 806 (10) |
| K562 A2Kb | 5 (3) | 4 (3) |
| K562 A2Kb HER-2+ | 366 (79) | 98 (8) |
| SKOV3 eGFP | 69 (7) | 1 (2) |
| SKOV3 A2+HER-2+ | 162 (12) | 114 (23) |

( ) = SD

TABLE 3

RaDHER2-1 vaccine induced T cell responses

| | IFNγ SFC/1e6 splenocytes RaDHER2-1 | | |
|---|---|---|---|
| Peptide pulsed target | 10 μg/ml | 1 μg/ml | 0.1 μg/ml |
| HER-2 p106 | 1156 (18) | 1133 (60) | 1112 (90) |

( ) = SD

As shown in Table 2, RaDHER2-1 vaccine induced T cell responses to 3 human HLA A2 HER2 epitopes p5, p98, p106 as well as tumor cells expressing the endogenously processed human HER2 antigen (K562 A2kb hHER2 and SKOV3 A2+).

The quality of the T cell responses was compared within three different concentrations of p106 epitope in the IFNγ ELISPOT assay, the result being presented in Table 3. As shown in Table 3, the T cell responses induced by RaDHER2-1 vaccine to human HER2 p106 epitope remained high at 0.1 μg/ml of peptide concentration. Together these data confirmed that the RaDHER2-1 antigen can be processed and presented in human MHC class I system, and induce high quality T cell responses to human HER2 antigen.

Results for RaDHER2-2 are shown in Table 4.

TABLE 4

RaDHER2-2 vaccine induced T cell responses

| Peptide pulsed targets and human HER-2+ tumor cells | IFNγ SFC/1e6 splenocytes |
|---|---|
| HBV p18 | 0 (0) |
| HER-2 p5 | 672 (15) |
| HER-2 p48 | 454 (110) |
| HER-2 p106 | 2000 (0) |

TABLE 4-continued

RaDHER2-2 vaccine induced T cell responses

| Peptide pulsed targets and human HER-2+ tumor cells | IFNγ SFC/1e6 splenocytes |
|---|---|
| HER-2 p435 | 2000 (0) |
| K562 A2Kb | 1 (2) |
| K562 A2Kb-HER2+ | 1590 (165) |

As shown in Table 4, RaD2HER2-2 vaccine induced T cell responses to 3 human HLA A2 HER2 epitopes p5, p48, p106, and p435, as well as tumor cells expressing the endogenously processed human HER2 antigen (K562 A2kb hHER2).

Figure 2A:
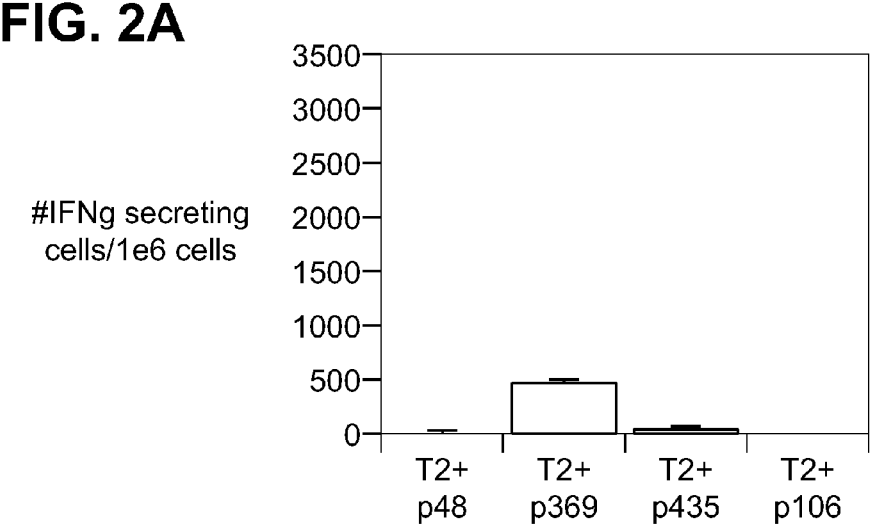
FIG. 2 shows results of a representative IFNγ ELISPOT assay to evaluate the ability of the RaDHER2 antigen to induce HER-2 specific CD8 T cells. The responses from two independent cultures showed specificity to HER2 p369 sequences (FIG. 2a) and p435 peptide sequence (FIG. 2b), respectively when compared to other HER-2 peptides tested.
Figure 2B:
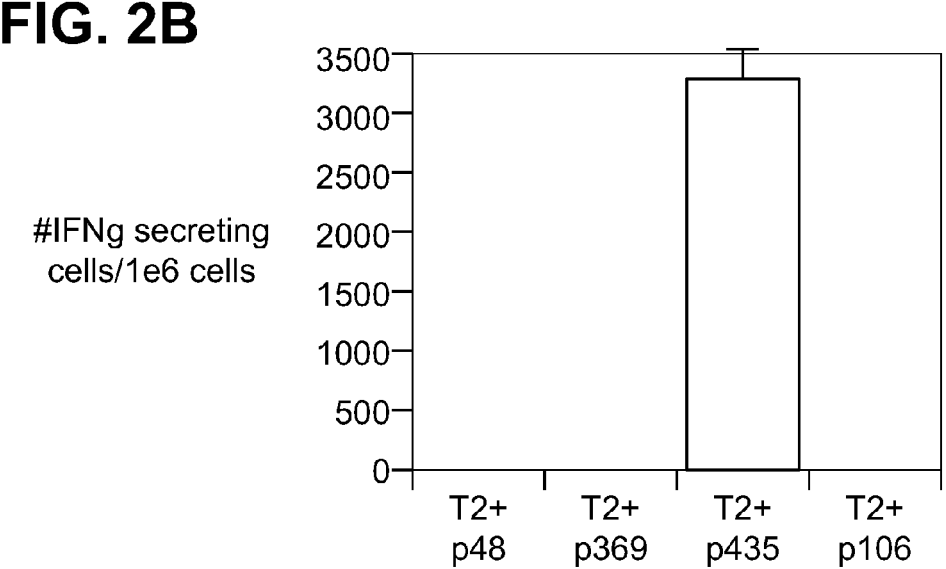

3c. Induction of HER2 Specific CD8 T Cells in In Vitro Human PBMC System:

The ability of RaDHER2-1 DNA when expressed, processed and presented in dendritic cells upon electroporation to induce HER2 specific CD8 T cells was analyzed in a fully human system using human PBMCs. Briefly, four day differentiated dendritic cells were generated from plastic adherent monocytes isolated from HLA A2 type donor PBMCs in the presence of GMCSF and IL-4. The differentiated dendritic cells were electroporated with RaDHER2-1 plasmid DNA in Nucleofector solution at 5 μg/100 μl containing 1e6 dendritic cells using Amaxa Nucleofector with program U002 and returned to the differentiation medium for another 24 hrs at 37° C. and 5% $CO_2$. Autologous CD8 T cells were co-cultured with RaDHER2-1 DNA electroporated dendritic cells at a 5:1 cell ratio supplemented with IL-7 at 10 ng/ml and subsequently with IL-10 at 10 ng/ml 24 hrs later. The CD8 T cells were stimulated again with irradiated and RaDHER2 electroporated dendritic cells as above on day 7 at a CD8: dendritic cell ratio of 10:1. IFNγ ELISPOT was performed seven days after stimulation to confirm the induction of HER2 specific T cells by RaDHER2-1 (data not shown). The epitope specificity of the response was determined after another week of stimulation with adherent autologous monocytes that were irradiated and pulsed with a pool of human HER2 specific peptides (HER2 p48, p106, p369 and p435) and β-2-microglobulin. Approximately 1e5 stimulated CD8 cells from each well were cultured with irradiated T2 cells loaded with corresponding peptide at 10 μg/ml for 20 hrs at 37° C. and 5% $CO_2$ in IFNγ ELISPOT plates. Plot is normalized to the number of cells that secrete IFNγ from 1e6 CD8 cells. Two independent wells from the same experiment that elicited T cell responses to HER2 peptides are shown. The cultures showed specificity to HER2 p369 (FIG. 2a) and p435 peptide sequence (FIG. 2b), respectively.

Figure 3:
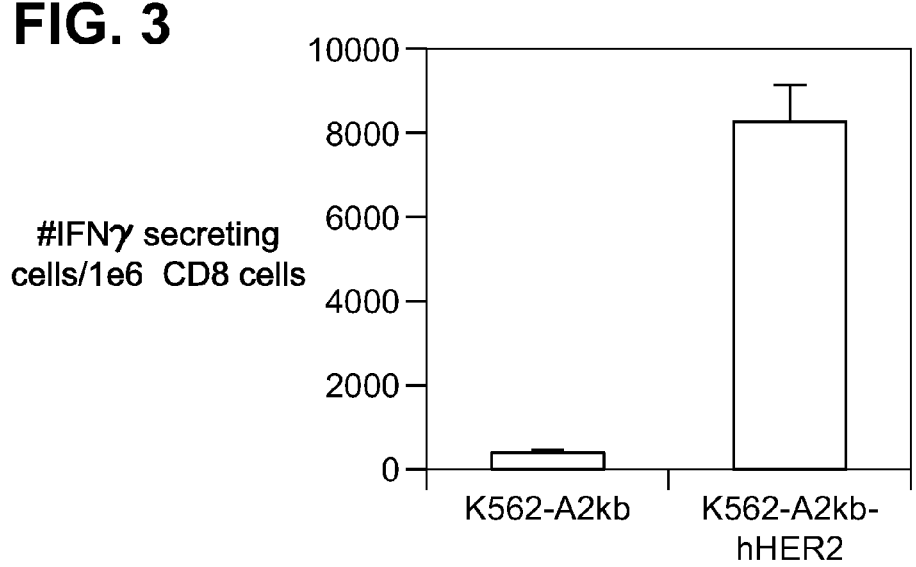
FIG. 3 shows results from a representative assay to further characterize the ability of the p435-specific-CD8 T cells induced by the RaDHER2 antigen to recognize tumor cells expressing native HER-2 in an IFNγ ELISPOT assay. Plot is normalized to the number of cells that secrete IFNγ in 1e6 CD8 cells.

The p435-specific-CD8 culture was further characterized for the ability to recognize HER-2 epitopes presented by cells (K562-A2kb-hHER2) that endogenously express and present HER2 in an HLA A2 restricted manner in an IFNγ ELISPOT assay. Briefly, the p435-specific-CD8 cells were expanded by co-culturing the cells with 2.5e6 partially allogeneic (only HLA A2 matched) and irradiated human PBMCs that have been pulsed with human p435 peptides at a concentration of 10 μg/ml for 2 hours. The cultures were then supplemented with 0.1 μg of anti-CD3 antibodies in complete media and incubated at 37° C. and 5% $CO_2$. The cultures were further supplemented with IL-2 at 100 IU/ml the next day and at 25 IU/ml every 3 days for 14 days prior to the IFNγ ELISOT assay. In the ELISPOT plates, the expanded CD8 cells were incubated with 48 hour IFNγ pretreated K562-A2kb-hHER2 or K562-A2kb cells for 20 hours (FIG. 3). Plot is normalized to the number of cells that secrete IFNγ in 1e6 CD8 cells. The p435-specific-CD8 cells elicited IFNγ—response to human HER-2 epitopes presented on the cells (K562-A2kb-hHER2) when compared to the response to the parental K562-A2kb cells that do not express human HER-2.

Together these data show that the RaDHER2-1 antigen can be processed and presented in human MHC class I system, and induce CD8 cell responses to human HER2 antigen.

The invention claimed is:

1. An isolated immunogenic HER-2 peptide which comprises an ECD-derived peptide, wherein the ECD-derived peptide comprises an amino acid sequence that (i) is 90% to 100% identical to amino acids 23-645 of SEQ ID NO: 5 or 95% to 100% identical to amino acids 25-647 of SEQ ID NO: 14, (ii) comprises amino acid sequences of at least four of the conserved T cell epitopes in the ECD of human HER-2 protein, and (iii) is 70% to 95% identical to the amino acid sequence of the ECD of human HER-2 protein, and wherein the amino acid sequence of the human HER-2 protein is set forth in SEQ ID NO: 1.

2. The isolated immunogenic HER-2 peptide according to claim 1, wherein the ECD-derived peptide comprises amino acids 23-645 of SEQ ID NO:5.

3. The isolated immunogenic HER-2 peptide according to claim 1, which comprises amino acids 23-910 of SEQ ID NO:3.

4. The isolated immunogenic HER-2 peptide according to claim 1, which comprises amino acids 23-940 of SEQ ID NO:9.

5. The isolated immunogenic HER-2 peptide according to claim 1, wherein the ECD-derived peptide comprises amino acids 25-647 of SEQ ID NO:14.

6. The isolated immunogenic HER-2 peptide according to claim 1, which comprises amino acids 25-912 of SEQ ID NO:18.

7. The isolated immunogenic HER-2 peptide according to claim 1, which comprises amino acids 25-956 of SEQ ID NO:20.

* * * * *